(12) United States Patent
Arora et al.

(10) Patent No.: US 7,452,880 B2
(45) Date of Patent: Nov. 18, 2008

(54) SUBSTITUTED PYRAZOLO [3,4-D] PYRIMIDINES AND METHODS OF USING THE SAME

(76) Inventors: Nidhi Arora, 10094 Randy La., Cupertino, CA (US) 95014; Roland Joseph Billedeau, 3491 Butcher Dr., Santa Clara, CA (US) 95051; Nolan James Dewdney, 1770 Fumia Ct., San Jose, CA (US) 95131; Tobias Gabriel, 700 Steiner St., No. 505, San Francisco, CA (US) 94117; David Michael Goldstein, 7045 Huntsfield Ct., San Jose, CA (US) 95120; Teresa Alejandra Trejo-Martin, 32772 S. Artistry Loop, Union City, CA (US) 94587

( * ) Notice: Subject to any disclaimer, the term of this patent is extended or adjusted under 35 U.S.C. 154(b) by 173 days.

(21) Appl. No.: 11/065,890

(22) Filed: Feb. 25, 2005

(65) Prior Publication Data
US 2005/0203091 A1    Sep. 15, 2005

Related U.S. Application Data

(60) Provisional application No. 60/548,642, filed on Feb. 27, 2004.

(51) Int. Cl.
| | |
|---|---|
| C07D 487/04 | (2006.01) |
| C07D 413/04 | (2006.01) |
| A61K 31/519 | (2006.01) |
| A61K 31/5355 | (2006.01) |
| A61K 31/497 | (2006.01) |
| A61P 19/02 | (2006.01) |
| A61P 11/04 | (2006.01) |
| C07D 471/02 | (2006.01) |
| A61K 31/4985 | (2006.01) |
| A61K 31/437 | (2006.01) |

(52) U.S. Cl. .................. 514/234.2; 544/262; 544/118; 544/350; 544/236; 514/262.1; 514/252.16; 514/248; 514/300; 546/119

(58) Field of Classification Search ................. 544/262, 544/118; 514/262.1, 234.2
See application file for complete search history.

(56) References Cited

U.S. PATENT DOCUMENTS

| | | | | |
|---|---|---|---|---|
| 3,821,382 | A * | 6/1974 | Hoyle et al. ............. | 514/262.1 |
| 3,948,913 | A | 4/1976 | Howarth et al. | |
| 4,020,072 | A | 4/1977 | Hoehn | |
| 4,044,130 | A | 8/1977 | Howarth et al. | |
| 7,217,710 | B2 * | 5/2007 | Adams et al. ............. | 514/234.2 |
| 2002/0193610 | A1 | 12/2002 | Woltering et al. | |
| 2003/0207900 | A1 | 11/2003 | Chen et al. | |
| 2004/0176325 | A1 | 9/2004 | Munson et al. | |
| 2004/0180896 | A1 | 9/2004 | Munson et al. | |
| 2005/0197340 | A1 * | 9/2005 | Arora et al. ............... | 514/249 |
| 2005/0203091 | A1 | 9/2005 | Arora et al. | |
| 2005/0277655 | A1 * | 12/2005 | Ding et al. ............... | 514/262.1 |

FOREIGN PATENT DOCUMENTS

| | | |
|---|---|---|
| DE | 2052719 | 9/1971 |
| EP | 0 104 522 B1 | 5/1991 |
| EP | 1 148 054 A1 | 10/2001 |
| GB | 937.725 | 9/1963 |
| WO | WO 98/09961 A1 | 3/1998 |
| WO | WO 98/40384 A1 | 9/1998 |
| WO | WO 99/23077 A1 | 5/1999 |
| WO | WO 00/27627 A1 | 5/2000 |
| WO | WO 01/98301 A1 | 12/2001 |
| WO | WO 02/22586 A1 | 3/2002 |
| WO | WO 02/051837 A2 | 7/2002 |
| WO | WO 02/059088 A1 | 8/2002 |
| WO | WO 03/000187 A2 | 1/2003 |
| WO | WO 03/009852 A1 | 2/2003 |
| WO | WO 03/029209 A2 | 4/2003 |
| WO | WO 03/062392 A2 | 7/2003 |
| WO | WO 03/068754 A1 | 8/2003 |
| WO | WO 03/099820 A1 | 12/2003 |
| WO | WO 2004/078116 A2 | 9/2004 |
| WO | WO 2005/085248 A1 | 9/2005 |
| WO | WO 2005085248 | * 9/2005 |

OTHER PUBLICATIONS

Fijen (Clinical & Experimental Immunology, 2001, 124, 2-20).*
Gong et. al. (Chinese Chemical Letters, 2002, 13(7), 613-616).*
Hashimoto (J Pharmacol Exp Ther., 2000, 293(2), 370-375).*
Esper et. al. (Expert. Opin. Investig. Drugs, 2005, 14(5), 633-645).*
Jones et al; "British Society of Gastroenterology guidelines for the management of the irritable bowel syndrome." Gut 2000, (Suppl II)47:ii1-ii19.*
Badger, A. M., et al. "Pharmacological Profile of SB 203580, a Selective Inhibitor of Cytokine Suppressive Binding Protein/p38 Kinase, in Animal Models of Arthritis, Bone Resorption, Endotoxin shock and Immune Function," *J. Pharm. Exp. Therap.* (1996) vol. 279 (1) pp. 1453-1461.

(Continued)

*Primary Examiner*—Brenda Coleman
*Assistant Examiner*—Susanna Moore
(74) *Attorney, Agent, or Firm*—Robert C. Hall

(57) ABSTRACT

Compounds of the formula I:

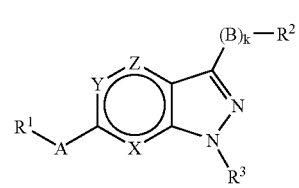

where A, B, X, Y, Z, k, $R^1$, $R^2$ and $R^3$ are those defined herein, and compositions comprising the same. The present invention also provides methods for preparing compounds of formula I and using the same in treating p38 mediated disorders in a patient.

12 Claims, No Drawings

OTHER PUBLICATIONS

Badger, A. M., et al, "SB 203580 Inhibitors p38 Mitogen-Activated Protein Kinase, Nitric Oxide Production, and Inducible Nitric Oxide Synthase in Bovine Cartilage-Derived Chondrocytes," *J. Immunol.* (1998) vol. 161, pp. 467-473.

Badger, A. M., et al. "Disease-Modifying Activity of SB242235, A Selective Inhibitor of p38 Mitogen-Activated Protein Kinase, in Rat Adjuvant-induced Arthritis," *Arthritis & Rheumatism* (2000) vol. 43 (1) pp. 175-183.

Jackson, J.R., et. al., "Pharmacological Effects of SB 220025, a Selective Inhibitor of P38 Mitogen-Activated Protein Kinase, in Angiogenesis and Chronic Inflammatory Disease Models," *J. Pharma. Exp. Therap.* (1998) vol. 284 (2) pp. 687-692.

Parasrampuria, D. A., et al., "Single-Dose Pharmacokinetics and Pharmacodynamics of RWJ 67657, a Specific p38 Mitogen-Activated Protein Kinase Inhibitors: A First-in-Human Study," *J. Clin. Pharmacol.* (2005) vol. 43, pp. 406-413.

Pargellis, C. et. al., "Inhibitors of p38 Mitogen-Activated Protein Kinase for the Treatment of Rheumatoid Arthritis," *Current Opin. Investigational Drugs* (2003) vol. 4 (5) pp. 566-571.

Studer, R. K., et al., "Chrondrocyte Response to Growth Factors is Modulated by p38 Mitogen-Activated protein Kinase Inhibitors," *Arthritis Research Ther.* (2004) vol. 6, R56-64.

Wada, Y., et. al., "R-130823, a Novel Inhibitor of p38 MAPK, Ameliorates Hyperalgesia and Swelling in Arthritis Models," *Europ, J. Pharmacol.* (2005) vol. 506, pp. 285-295.

Wadsworth, S. A., et. al., "RWJ 67657, a Potent, Orally Active Inhibitor of p38 Mitogen-Activated Protein Kinase," *J. Pharm. Exp. Therapeutics* (1999) vol. 291 (2) pp. 680-687.

\* cited by examiner

SUBSTITUTED PYRAZOLO [3,4-D] PYRIMIDINES AND METHODS OF USING THE SAME

CROSS REFERENCE TO RELATED APPLICATIONS

This application claims benefit under 35 U.S.C. 119(e) of U.S. Provisional Application No. 60/548,642 filed Feb. 27, 2004, which is hereby incorporated by reference in its entirety.

FIELD OF THE INVENTION

The present invention relates to azaindazoles, derivatives thereof, a process for their manufacture, pharmaceutical preparations comprising the same, and methods for using the same.

BACKGROUND OF THE INVENTION

Mitogen-activated protein kinases (MAP) is a family of proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases is the p38 kinase group that includes various isoforms (e.g., p38α, p39β, p38γ and p38δ). The p38 kinases are responsible for phosphorylating and activating transcription factors as well as other kinases, and are activated by physical and chemical stress, pro-inflammatory cytokines and bacterial lipopolysaccharide.

More importantly, the products of the p38 phosphorylation have been shown to mediate the production of inflammatory cytokines, including TNF and IL-1, and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV-7), human herpesvirus-8 (HHV-8), pseudorabies and rhinotracheitis, among others.

Similarly, IL-1 is produced by activated monocytes and macrophages, and plays a role in many pathophysiological responses including rheumatoid arthritis, fever and reduction of bone resorption.

Additionally, the involvement of p38 has been implicated in stroke, Alzheimer's disease, osteoarthritis, lung injury, septic shock, angiogenesis, dermatitis, psoriasis and atopic dermatitis. *J. Exp. Opin. Ther. Patents,* 2000, 10(1).

The inhibition of these cytokines by inhibition of the p38 kinase is of benefit in controlling, reducing and alleviating many of these disease states.

SUMMARY

The invention provides compounds of the formula I:

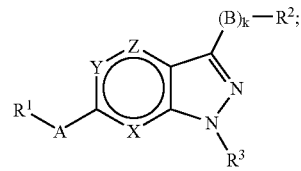

or pharmaceutically acceptable salts, solvates or prodrugs thereof, wherein:
$R^1$ is optionally substituted aryl, optionally substituted heteroaryl, or cycloalkyl;
$R^2$ is optionally substituted aryl, optionally substituted heteroaryl, cycloalkyl, branched alkyl, iodo or heterocyclyl;
$R^3$ is hydrogen or alkyl;
one or two of X, Y and Z is N, and the other is $CR^4$;
$R^4$ in each independent occurrence is hydrogen, alkyl, halo, amino, alkoxy, hydroxy, cyano, heteroalkyl, heterocyclyl, hydroxycycloalkyl or $-C(=O)-R^5$
wherein
$R^5$ is alkyl, hydroxy, alkoxy, amino, heteroalkyl, aryl, aralkyl, heteroaryl or heterocyclyl;
A is O, $CH_2$, $S(O)_n$, $C(=O)$, $CH_2(OR^6)$ or $NR^7$, $CH_2NR^7$, or $R^1$ and $R^7$ may together form a heterocyclyl,
wherein n is 0, 1 or 2;
$R^6$ and $R^7$ are hydrogen or alkyl;
k is 0 or 1;
B is O, $NR^8$, $S(O)_j$, $CH(OR^9)$, $CH=CH$, or $C(=O)$,
wherein
j is 0, 1 or 2; and
$R^8$ is hydrogen, alkyl, $-C(=O)-R^{10}$, or $-SO_2R^{11}$,
wherein
$R^{10}$ is alkyl, hydroxy, alkoxy, amino, heteroalkyl, aryl, aralkyl, heteroaryl or heterocyclyl; and
$R^{11}$ is alkyl; and
$R^9$ is hydrogen or alkyl;
provided that when A is $NR^6$, $R^1$ is not 5-methanesulfonyl-2-methoxyphenyl.

Another aspect of the present invention provides a pharmaceutical formulation comprising one or more compounds of formula I and a pharmaceutically acceptable carrier, diluent, and/or excipient therefor.

The invention also provides a method of preparing a compound of formula qq:

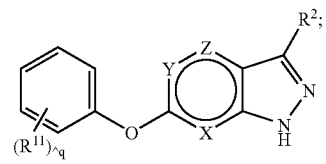

the method comprising:
reacting a compound of formula pp;

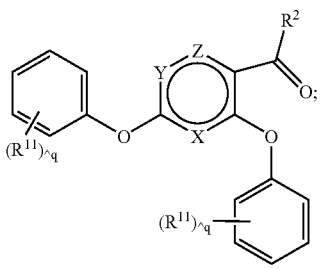

wherein q is from 1 to 4, $R^{11}$ is and X, Y, Z and R2 are as defined herein;
with hydrazine, to form the compound of formula qq.
The method may further comprise:
reacting a compound of formula mm:

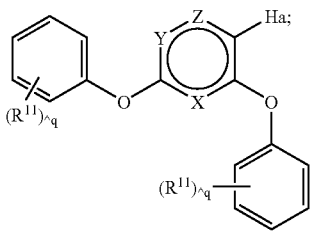

wherein Ha is halo and q, X, Y, Z, R2 and $R^{11}$ are as defined herein,
with Grignard reagent nn:

$$R^2\text{—MgHa} \qquad \qquad \text{nn;}$$

and acyl compound oo:

$$R^2\text{—C(O)Ha} \qquad \qquad \text{oo;}$$

to form compound pp.

Compounds of the invention are inhibitors of protein kinases, and exhibit effective activity against p38 in vivo. They are selective for p38 kinase relative to cyclin-dependent kinases and tyrosine kinases. Therefore, compounds of the present invention can be used for the treatment of diseases mediated by the pro-inflammatory cytokines such as TNF and IL-1. Thus, another aspect of the present invention provides a method for treating p38 mediated diseases or conditions in which a therapeutically effective amount of one or more compounds of formula I is administered to a patient.

DETAILED DESCRIPTION OF THE INVENTION

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means a linear saturated monovalent hydrocarbon moiety of one to six carbon atoms or a branched saturated monovalent hydrocarbon moiety of three to six carbon atoms, e.g., methyl, ethyl, propyl, 2-propyl, n-butyl, iso-butyl, tert-butyl, pentyl, and the like.

"Alkylene" means a linear saturated divalent hydrocarbon moiety of one to six carbon atoms or a branched saturated divalent hydrocarbon moiety of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—(O)—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxy-ethyl, 1-(2-methoxyethyl)-3-methoxypropyl, and 1-(2-methoxyethyl)-3-methoxypropyl.

"Alkylamino" means a moiety of the formula —NR—R' wherein R is hyrdogen or alkyl and R' is alkyl as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Alkylsulfonylalkyl" means a moiety of the formula $R^a$—$SO_2$—$R^b$—, where $R^a$ is alkyl and $R^b$ is alkylene as defined herein. Exemplary alkylsulfonylalkyl groups include, by way of example, 3-methanesulfonylpropyl, 2-methanesulfonylethyl, 2-methanesulfonylpropy, and the like.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Aryl" means a monovalent monocyclic or bicyclic aromatic hydrocarbon moiety which is optionally substituted with one or more, preferably one, two or three, substituents, each of which is preferably selected from the group consisting of alkyl, hydroxy, alkoxy, haloalkyl, haloalkoxy, halo, nitro, cyano, amino, mono- and dialkylamino, methylenedioxy, ethylenedioxy, acyl, heteroalkyl, optionally substituted aryl, optionally substituted heteroaryl, optionally substituted aralkyl, and optionally substituted heteroaralkyl. A particularly preferred aryl substituent is halide. More specifically the term aryl includes, but is not limited to, phenyl, 1-naphthyl, 2-naphthyl, and the like, each of which can be substituted or unsubstituted.

"Aralkyl" refers to a moiety of the formula —RR', where R' is optionally substituted aryl and R is alkylene as defined herein.

"Aralkyloxy" refers to a moiety of the formula —ORR', where R' is optionally substituted aryl and R is alkylene as defined herein.

"Substituted aralkyl" or "optionally substituted aralkyl" refers to aralkyl in which the aryl moiety is substituted or optionally substituted, respectively.

"Cycloalkyl" refers to a saturated monovalent cyclic hydrocarbon moiety of three to seven ring carbons e.g., cyclopropyl, cyclobutyl, cyclohexyl, 4-methyl-cyclohexyl, and the like. Cycloalkyl may optionally be substituted with one or more substituents, preferably one, two or three, substituents. Preferably, cycloalkyl substituent is selected from the group consisting of alkyl, hydroxy, alkoxy, haloalkyl, haloalkoxy, halo, amino, mono- and dialkylamino, heteroalkyl, acyl, aryl and heteroaryl.

"Cycloalkylalkyl" refers to a moiety of the formula $R^c$—$R^d$—, where $R^c$ is cycloalkyl and $R^d$ is alkylene as defined herein.

"Halo", "halogen" and "halide" are used interchangeably herein and refer to fluoro, chloro, bromo, or iodo. Preferred halides are fluoro and chloro with fluoro being a particularly preferred halide.

"Haloalkyl" means alkyl substituted with one or more same or different halo atoms, e.g., —$CH_2Cl$, —$CF_3$, —$CH_2CF_3$, —$CH_2CCl_3$, and the like.

"Heteroalkyl" means an alkyl moiety as defined herein wherein one or more, preferably one, two or three, hydrogen atoms have been replaced with a substituent independently selected from the group consisting of —$OR^a$, —$NR^bR^c$ (where n is 0 or 1 if $R^b$ and $R^c$ are both independently alkyl, cycloalkyl or cycloalkylalkyl, and 0 if not) and —$S(O)_nR^d$ (where n is an integer from 0 to 2), with the understanding that the point of attachment of the heteroalkyl moiety is through a carbon atom, wherein $R^a$ is hydrogen, acyl, alkoxycarbonyl, alkyl, cycloalkyl, or cycloalkylalkyl; $R^b$ and $R^c$ are independently of each other hydrogen, acyl, alkoxycarbonyl, alkyl, cycloalkyl, cycloalkylalkyl, alkylsulfonyl, aminosulfonyl, mono- or di-alkylaminosulfonyl, aminoalkyl, mono- or di-alkylaminoalkyl, hydroxyalkyl, alkoxyalkyl, hydroxyalkylsulfonyl or alkoxyalkylsulfonyl; and when n is 0, $R^d$ is hydrogen, alkyl, cycloalkyl, cycloalkylalkyl, or aryl, and when n is 1 or 2, $R^d$ is alkyl, cycloalkyl, cycloalkylalkyl, or optionally substituted phenyl. Representative examples include, but are not limited to, 2-hydroxyethyl, 3-hydroxypropyl, 2-hydroxy-1-hydroxymethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like. Accordingly, hydroxyalkyl and alkoxyalkyl are subset of heteroalkyl.

"Heteroaryl" means a monovalent monocyclic or bicyclic moiety of 5 to 12 ring atoms having at least one aromatic ring containing one, two, or three ring heteroatoms selected from N, O, or S (preferably N or O), the remaining ring atoms being C, with the understanding that the attachment point of the heteroaryl moiety will be on an aromatic ring. The heteroaryl ring is optionally substituted independently with one or more substituents, preferably one, two or three substituents, each of which is independently selected from alkyl, haloalkyl, hydroxy, alkoxy, halo, nitro and cyano. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof.

"Heteroarylalkyl" refers to a moiety of the formula $Ar^z$—$R^y$—, where $Ar^z$ is heteroaryl and $R^y$ is alkylene as defined herein.

"Heterocyclyl" means a saturated or unsaturated non-aromatic cyclic moiety of 3 to 8 ring atoms in which one or two ring atoms are heteroatoms selected from N, O, or $S(O)_n$ (where n is an integer from 0 to 2), preferably N or O, the remaining ring atoms being C, where one or two C atoms may optionally be replaced by a carbonyl group. The heterocyclyl ring may be optionally substituted independently with one or more, preferably one, two, or three, substituents, each of which is independently selected from alkyl, haloalkyl, hydroxyalkyl, halo, nitro, cyano, cyanoalkyl, hydroxy, alkoxy, amino, mono- and dialkylamino, aralkyl, —$(X)_n$—C(O)$R^e$ (where X is O or $NR^f$, n is 0 or 1, $R^e$ is hydrogen, alkyl, haloalkyl, hydroxy (when n is 0), alkoxy, amino, mono- and dialkylamino, or optionally substituted phenyl, and $R^f$ is H or alkyl), -alkylene-C(O)$R^g$ (where $R^g$ is alkyl, —$OR^h$ or $NR^iR^j$ and $R^h$ is hydrogen, alkyl or haloalkyl, and $R^i$ and $R^j$ are independently hydrogen or alkyl), and —$S(O)_nR^k$ (where n is an integer from 0 to 2) such that when n is 0, $R^k$ is hydrogen, alkyl, cycloalkyl, or cycloalkylalkyl, and when n is 1 or 2, $R^k$ is alkyl, cycloalkyl, cycloalkylalkyl, amino, acylamino, monoalkylamino, or dialkylamino. A particularly preferred group of heterocyclyl substituents include alkyl, haloalkyl, hydroxyalkyl, halo, hydroxy, alkoxy, amino, mono- and dialkylamino, aralkyl, and —$S(O)_nR^k$. In particular, the term heterocyclyl includes, but is not limited to, tetrahydrofuranyl, pyridinyl, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxo-tetrahydro-2H-thiopyranyl), pyrrolinyl, imidazolinyl, N-methanesulfonyl-piperidin-4-yl, and the derivatives thereof, each of which may be optionally substituted.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycycloalkyl" refers to a subset of cycloalkyl moiety as defined herein and specifically refers to a cycloalkyl moiety as defined herein where one or more, preferably one, two or three, hydrogen atoms in the cycloalkyl moiety have been replaced with a hydroxy substituent. Representative examples include, but are not limited to, 2-, 3-, or 4-hydroxycyclohexyl, and the like.

"Pyridylalkyloxy" means a moiety of the formula —OR—R' wherein R is alkylene as defined herein and R' is pyridyl.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optionally substituted phenyl" means a phenyl ring which is optionally substituted independently with one or more substituents, preferably one or two substituents selected from the group consisting of alkyl, hydroxy, alkoxy, haloalkyl, haloalkoxy, halo, nitro, cyano, amino, methylenedioxy, ethylenedioxy, and acyl.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that may be cleaved in vivo to regenerate the free hydroxyl, amino, or sulfhydryl group, respectively. Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p 1-92, Elesevier, New York-Oxford (1985).

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, $2^{nd}$ ed. 1991) and Harrison and Harrison et al., *Compendium of Synthetic Organic Methods*, Vols. 1-8 (John Wiley and Sons, 1971-1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) inhibiting the disease, i.e., arresting or reducing the development of the disease or its clinical symptoms; or (2) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

As used herein, the terms "those defined above" and "those defined herein" are used interchangeably herein and, when referring to a variable, incorporates by reference the broad definition of the variable as well as preferred, more preferred and most preferred definitions, if any.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The terms "those defined above" and "those defined herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature. Numbering of the ring system of the subject compounds as described herein is shown by the formula below.

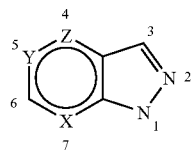

Chemical structures shown herein were prepared using ISIS® version 2.2. Any open valency appearing on a carbon, oxygen or nitrogen atom in the structures herein indicates the presence of a hydrogen.

Compounds of the Invention

The invention provides compounds of the formula I:

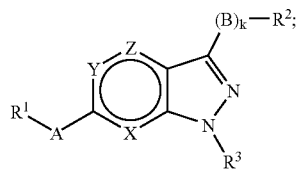

or a pharmaceutically acceptable salt thereof, wherein:

$R^1$ is optionally substituted aryl, optionally substituted heteroaryl, or cycloalkyl;

$R^2$ is optionally substituted aryl, optionally substituted heteroaryl, cycloalkyl, branched alkyl, iodo or heterocyclyl;

$R^3$ is hydrogen or alkyl;

one or two of X, Y and Z is N, and the other is $CR^4$;

$R^4$ in each independent occurrence is hydrogen, alkyl, halo, amino, alkoxy, hydroxy, cyano, heteroalkyl, heterocyclyl, hydroxycycloalkyl or $—C(=O)—R^5$ wherein $R^5$ is alkyl, hydroxy, alkoxy, amino, heteroalkyl, aryl, aralkyl, heteroaryl or heterocyclyl;

A is O, $CH_2$, $S(O)_n$, $C(=O)$, $CH_2(OR^6)$ or $NR^7$, $CH_2NR^7$, or $R^1$ and $R^7$ may together form a heterocyclyl, wherein n is 0, 1 or 2;

$R^6$ and $R^7$ are hydrogen or alkyl;

k is 0 or 1;

B is O, $NR^8$, $S(O)_j$, $CH(OR^9)$, $CH=CH$, or $C(=O)$, wherein j is 0, 1 or 2; and $R^8$ is hydrogen, alkyl, $—C(=O)—R^{10}$, or $—SO_2R^{11}$, wherein $R^{10}$ is alkyl, hydroxy, alkoxy, amino, heteroalkyl, aryl, aralkyl, heteroaryl or heterocyclyl; and $R^{11}$ is alkyl; and $R^9$ is hydrogen or alkyl;

provided that when A is $NR^6$, $R^1$ is not 5-methanesulfonyl-2-methoxyphenyl.

In many embodiments of formula I, k is 0. In certain embodiments of formula I, $R^3$ is hydrogen.

In many embodiments of the invention the subject compounds are of formula II:

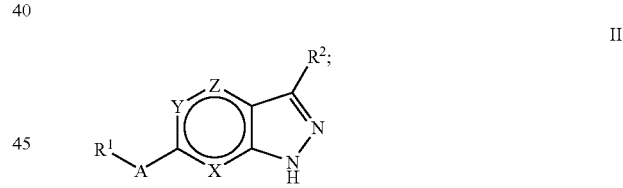

wherein X, Y, Z, A, $R^1$ and $R^2$ are as defined herein.

In certain embodiments of formula I or formula II, A may be O, $CH_2$, $S(O)_n$, $C(=O)$, $CH_2(OR^6)$ or $NR^7$, or $CH_2NR^7$. Preferably A is O.

In certain embodiments of formula I or formula II, X and Y are nitrogen and Z is $CR^4$.

In other embodiments of formula I or formula II, X and Z are nitrogen and Z is $CR^4$.

In still other embodiments of formula I or formula II, X is nitrogen and Y and Z are $CR^4$.

In yet other embodiments of formula I or formula II, Y is nitrogen and X and Z are $CR^4$.

In certain embodiments of formula I or formula II, Y and Z are nitrogen and X is $CR^4$.

In many such embodiments of formula I or formula II $R^4$ is preferably hydrogen.

In certain embodiments the compounds of the invention are of formula III:

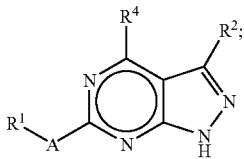

III wherein A, R$^1$, R$^2$ and R$^4$ are as defined herein.

In other embodiments the subject compounds may be of the formula IV:

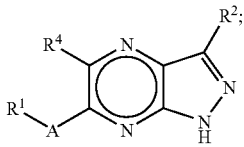

IV wherein A, R$^1$, R$^2$ and R$^4$ are as defined herein.

In still other embodiments the compounds may be of the formula V:

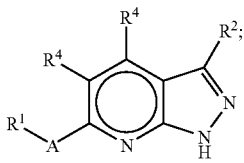

V wherein A, R$^1$, R$^2$ and R$^4$ are as defined herein.

In yet other embodiments the compounds may be of the formula VI:

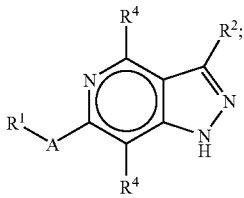

VI wherein A, R$^1$, R$^2$ and R$^4$ are as defined herein.

In further embodiments the compounds may be of the formula VII:

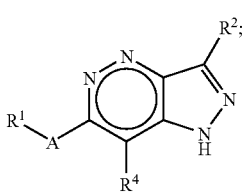

VII wherein A, R$^1$, R$^2$ and R$^4$ are as defined herein.

In still further embodiments the compounds may be of the formula VIII:

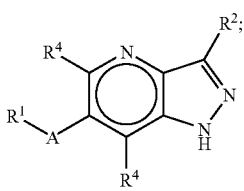

VIII wherein A, R$^1$, R$^2$ and R$^4$ are as defined herein.

In any of the embodiments of formulas I through VIII, A may be O, CH$_2$, S(O)$_n$, C(=O), CH$_2$(OR$^6$), NR$^7$, or CH$_2$NR$^7$. Preferably A is O. In some preferred embodiments of formula VII, A may be NR$^7$.

In any of the embodiments of formulas I through VIII, R$^1$ is preferably optionally substituted phenyl.

In any of the embodiments of formulas formulas I through VIII, R$^1$ may be 2-halophenyl or 2,4-dihalophenyl. More preferably, R$^1$ is 2,4-difluorophenyl.

In any of the embodiments of formulas I through VIII, R$^1$ may be 2,4-difluorophenyl, 4-fluorophenyl, 3-fluorophenyl, 2-fluorophenyl, phenyl, 2-chlorophenyl, 3,4-difluorophenyl, 4-trifluoromethylphenyl, 3-trifluoromethylphenyl, 2-trifluoromethylphenyl, 4-methylphenyl, 4-methoxyphenyl, 3,4-dichlorophenyl, or 1,3-benzodioxol-5-yl.

In any of the embodiments of formulas I through VIII, R$^2$ may be optionally substituted phenyl, optionally substituted thienyl, or optionally substituted pyridyl. Preferably R$^2$ is optionally substituted phenyl.

In any of the embodiments of formulas I through VIII, R$^2$ may be phenyl optionally substituted with halo, alkyl, amino, alkoxy, haloalkyl, hydroxy, hydroxyalkoxy, alkylsulfanyl, alkoxyamino, heteroaryl, heterocyclyl, heterocyclylalkyl, heterocyclyloxy, heterocyclylalkoxy, thienyl, aminoalkoxy, hydroxyalkylamino, hydroxyalkylaminoalkyl, aralkyloxy, or pyridylalkyloxy. In certain embodiments R$^2$ is 2-halophenyl, and more preferably 2-chlorophenyl. In specific embodiments R$^2$ is phenyl with chloro at the 2-position and with hydroxy, methoxy, 4-methylpiperidinyl, 2-methoxyethylmethylamino, isopropoxy, pyridin-2-ylethoxy, amino, methylsulfanyl, 2,3-dihydroxypropoxy, 2-hydroxyethoxy, 2-(morpholin-4-yl)-ethoxy, 2-(dimethylamino)-ethoxy, 3,4-dihydroxybutyloxy, morpholin-4-ylmethyl, (2-hydroxypropyl)-aminomethyl, hydroxymethyl, ethoxy, piperidin-4-yloxy, or pyran-4-yloxy at the 4- or 5-position.

In any of the embodiments of formulas I through VIII, R$^2$ may be phenyl optionally substituted with chloro, fluoro, bromo, methyl, methoxy, trifluoromethyl, pyridyl, morpholino, benzyloxy, 4-methylpiperidinyl, 2-methoxyethylmethylamino, isopropoxy, pyridin-2-ylethoxy, amino, methylsulfanyl, 2,3-dihydroxypropoxy, 2-hydroxyethoxy, 2-(morpholin-4-yl)-ethoxy, 2-(dimethylamino)-ethoxy, 3,4-dihydroxybutyloxy, morpholin-4-ylmethyl, (2-hydroxypropyl)-aminomethyl, hydroxymethyl, ethoxy, piperidin-4-yloxy, or pyran-4-yloxy.

In any of the embodiments of formulas I through VIII, R$^2$ may be 2-chlorophenyl, 4-fluorophenyl, 4-methoxyphenyl, 3-trifluormethylphenyl, pyridin-2-yl, pyridin-3-yl, thien-2-yl, 3-(morpholin-4-yl)-phenyl, 4-hydroxyphenyl, 4-benzyloxyphenyl, 3-(4-methyl-piperazin-1-yl)-phenyl, 4-(morpholin-4-yl)-phenyl, 3-(2-methoxyethyl-methylamino)-phenyl, 4-isopropoxyphenyl, 3-(2-pyridin-2-yl-ethoxy)-phenyl, 4-aminophenyl, 4-(4-methyl-piperazin-1-yl)-phenyl, 4-bromophenyl, 2-fluorophenyl, 3-benzyloxyphenyl, 2-methylsulfanyl, 4-methoxy-2-methylphenyl, 4-(2,3-dihydroxypropoxy)-2-methyl-phenyl, 2-chloro-4-methoxyphenyl, 3-methylpyridin-2-yl, 2-fluoro-5-methoxyphenyl, 4-fluoro-2-methylphenyl, 2,4-dimethylphenyl, 2-fluoro-4-(morpholin-4-yl)-phenyl, 4-bromo-2-fluorophenyl, 2-chloro-4-methylphenyl, 2-fluoro-6-methoxyphenyl, 4-hydroxy-2-methylphenyl, 4-(2-hydroxyethoxy)-2-methylphenyl, 2-chloro-4-(2,3-dihydroxypropoxy)-phenyl, 2-chloro-4-hydroxyphenyl, 2-chloro-4-(2-hydroxyethoxy)-phenyl, 2-chloro-4-(2-[morpholin-4-yl]-ethoxy)-phenyl, 2-chloro-4-(2-dimethylamino)-ethoxy-phenyl, 2-chloro-4-2,3-dihydroxypropoxyphenyl, 2-chloro-4-(morpholin-4-ylmethyl)-phenyl, 2-chloro-4-(2-hydroxypropyl)aminomethyl-phenyl, 2-chloro-5-2,3-dihydroxypropoxyphenyl, 2-chloro-5-hydroxyphenyl, 2-chloro-5-(2-hydroxyethyoxy)-phenyl, 2-chloro-4-hydroxymethylphenyl, 2-ethoxyphenyl, 2-ethoxypyridin-3-yl-phenyl, 2-chloro-5-(2-dimethylaminoethoxy)-phenyl, 2-chloro-5-piperidin-4-yloxy-phenyl, 2-chloro-5-pyran-4-yloxy-phenyl, or 2-methylpyridin-3-yl-phenyl.

In any of the embodiments of formulas I through VIII, $R^4$ is preferably hydrogen.

In many embodiments of the invention, the subject compounds may be represented by formula IX:

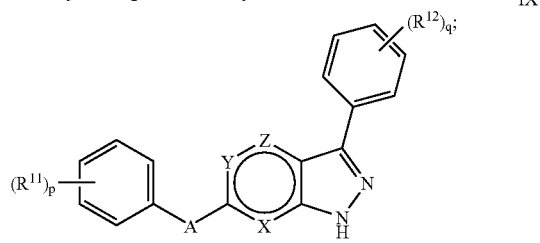

wherein:
each of p and q is independently from 0 to 4;
each $R^{11}$ is independently halo, alkyl, alkoxy, haloalkyl, or cyano;
each $R^{12}$ is independently halo, alkyl, amino, alkoxy, haloalkyl, hydroxy, hydroxyalkoxy, alkylsulfanyl, alkoxyamino, heteroaryl, heterocyclyl, heterocyclylalkyl, heterocyclyloxy, heterocyclylalkoxy, aminoalkoxy, hydroxyalkylamino, hydroxyalkylaminoalkyl, aralkyloxy, or pyridylalkyloxy; and
X, Y, Z, A, $R^1$, $R^2$ and $R^5$ are as defined herein.

In certain embodiments of formula IX, A may be O, $CH_2$, $S(O)_n$, $C(=O)$, $CH_2(OR^6)$ or $NR^7$, or $CH_2NR^7$. Preferably A is O.

In certain embodiments, compounds of the invention may be of formula X:

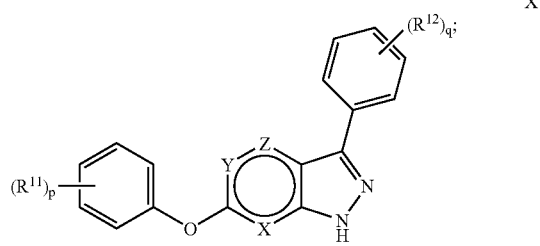

wherein X, Y, Z, p, q, $R^{11}$ and $R^{12}$ are as defined herein.

In certain embodiments of formula IX or formula X, X and Y are nitrogen and Z is $CR^4$.

In other embodiments of formula IX or formula X, X and Z are nitrogen and Z is $CR^4$.

In still other embodiments of formula IX or formula X, X is nitrogen and Y and Z are $CR^4$.

In yet other embodiments of formula IX or formula X, Y is nitrogen and X and Z are $CR^4$.

In certain embodiments of fformula IX or formula X, Y and Z are nitrogen and X is $CR^4$.

In many such embodiments of formula IX or formula X, $R^4$ is preferably hydrogen.

In certain embodiments, compounds of the invention may be of formula XI:

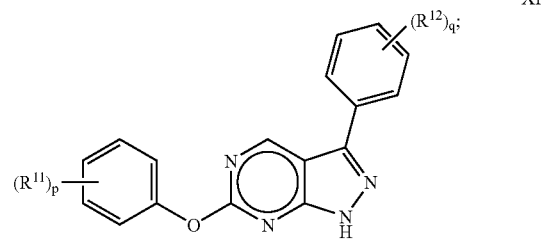

wherein p, q, $R^{11}$ and $R^{12}$ are as defined herein.

In certain embodiments, compounds of the invention may be of formula XII:

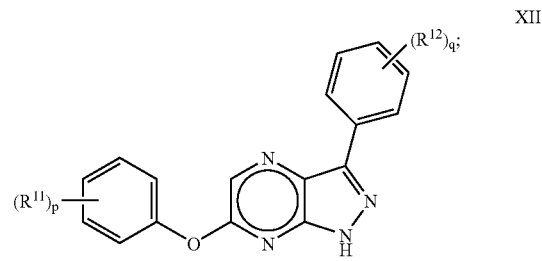

wherein p, q, $R^{11}$ and $R^{12}$ are as defined herein.

In certain embodiments, compounds of the invention may be of formula XIII:

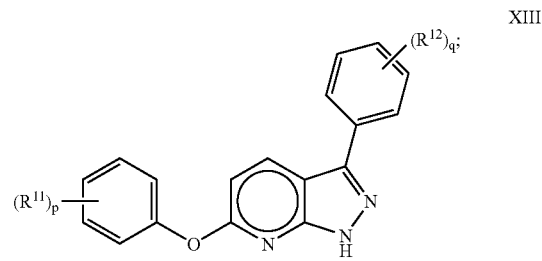

wherein p, q, $R^{11}$ and $R^{12}$ are as defined herein.

In certain embodiments, compounds of the invention may be of formula XIV:

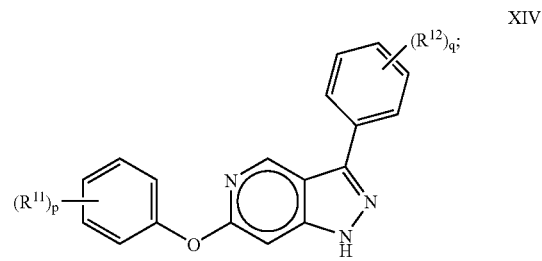

wherein p, q, $R^{11}$ and $R^{12}$ are as defined herein.

In certain embodiments, compounds of the invention may be of formula XV:

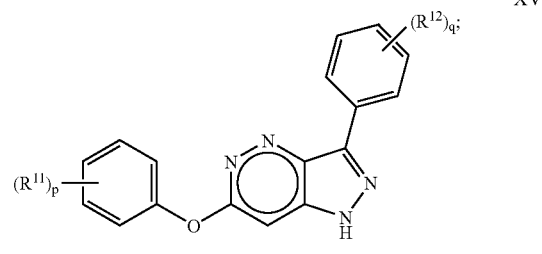

wherein p, q, $R^{11}$ and $R^{12}$ are as defined herein.

In certain embodiments, compounds of the invention may be of formula XVI:

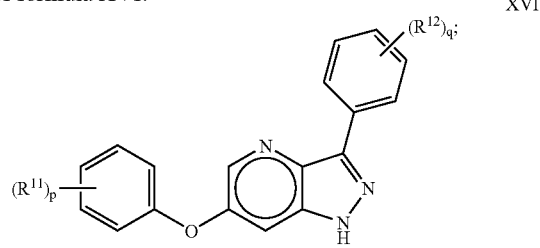

XVI wherein p, q, $R^{11}$ and $R^{12}$ are as defined herein.

In any of the embodiments of formulas IX through XVI, p is preferably 1 or 2, and $R^{11}$ is preferably halo.

In any of the embodiments of formulas IX through XVI, q may be 1 or 2, and $R^{12}$ may be halo, alkyl, amino, alkoxy, haloalkyl, hydroxy, hydroxyalkoxy, alkylsulfanyl, alkoxyamino, heteroaryl, heterocyclyl, heterocyclylalkyl, heterocyclyloxy, heterocyclylalkoxy, aminoalkoxy, hydroxyalkylamino, hydroxyalkylaminoalkyl, aralkyloxy, or pyridylalkyloxy.

In any of the embodiments of formulas IX through XVI, q may be 1 or 2, and $R^{12}$ may be chloro, fluoro, bromo, methyl, methoxy, trifluoromethyl, pyridyl, morpholino, benzyloxy, 4-methylpiperidinyl, 2-methoxyethyl-methylamino, isopropoxy, pyridin-2-ylethoxy, amino, methylsulfanyl, 2,3-dihydroxypropoxy, 2-hydroxyethoxy, 2-(morpholin-4-yl)-ethoxy, 2-(dimethylamino)-ethoxy, 3,4-dihydroxybutyloxy, morpholin-4-ylmethyl, (2-hydroxypropyl)-aminomethyl, hydroxymethyl, ethoxy, piperidin-4-yloxy, or pyran-4-yloxy. In certain embodiments, q is 1 and $R^{12}$ is 2-halo, preferably 2-chloro. In specific embodiments q is 2, and $R^{12}$ is halo at the 2-position and $R^{12}$ is hydroxy, alkoxy, hydroxyalkoxy, alkoxyamino, heterocyclyl, heterocyclylalkyl, heterocyclyloxy, heterocyclylalkoxy, aminoalkoxy, hydroxyalkylamino, hydroxyalkylaminoalkyl, aralkyloxy, or pyridylalkyloxy at the 4- or 5-position.

In embodiments wherein $R^2$ or $R^4$ is heterocyclyl, such heterocyclyl may be piperidinyl, piperazinyl or morpholinyl, each of which may be optionally substituted.

Where any of $R^1$, $R^2$, $R^3$, $R^4$, $R^5$, $R^6$, $R^7$, $R^8$, $R^9$, $R^{10}$ and $R^{11}$ are alkyl or contain an alkyl moiety, such alkyl is preferably lower alkyl, i.e. $C_1$-$C_6$alkyl, and more preferably $C_1$-$C_4$alkyl.

The compounds of the invention can exist in unsolvated forms as well as solvated forms, including hydrated forms. In general, the solvated forms, including hydrated forms, are equivalent to unsolvated forms and are intended to be encompassed within the scope of the present invention. In addition to the compounds described above, the compounds of the present invention include all tautomeric forms. Furthermore, the present invention also includes all pharmaceutically acceptable salts of those compounds along with prodrug forms of the compounds and all stereoisomers whether in a pure chiral form or a racemic mixture or other form of mixture.

The compounds of formula I are capable of further forming pharmaceutically acceptable acid addition salts. All of these forms are within the scope of the present invention.

Pharmaceutically acceptable acid addition salts of the compounds of Formula I include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharmaceutical Science*, 1977, 66, 1-19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Representative compounds in accordance with the invention are shown in Table 1 below.

TABLE 1

| # | Structure | Name (Autonom ™) | MP ° C. or M + H | Example |
|---|---|---|---|---|
| 1 | 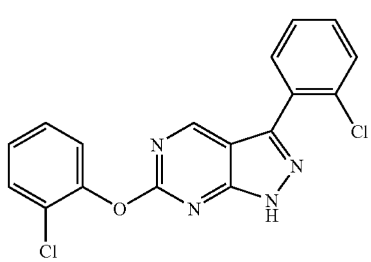 | 6-(2-Chloro-phenoxy)-3-(2-chloro-phenyl)-pyrazolo[3,4-d]pyrimidine | 358 | 1, 4 |

TABLE 1-continued

| # | Structure | Name (Autonom ™) | MP ° C. or M + H | Example |
|---|---|---|---|---|
| 2 | 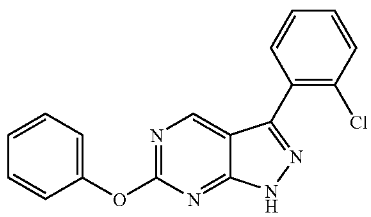 | 3-(2-Chloro-phenyl)-6-phenoxy-1H-pyrazolo[3,4-d]pyrimidine | 324 | 1 |
| 3 | 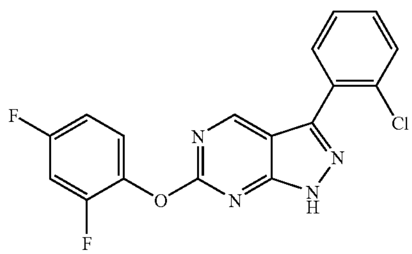 | 3-(2-Chloro-phenyl)-6-(2,4-difluoro-phenoxy)-1H-pyrazolo[3,4-d]pyrimidine | 173.4-176.4° C. | 1 |
| 4 | 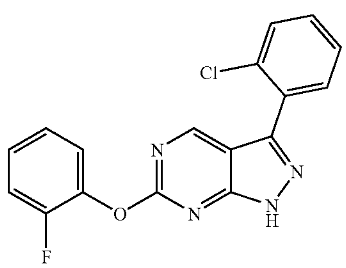 | 3-(2-Chloro-phenyl)-6-(2-fluoro-phenoxy)-1H-pyrazolo[3,4-d]pyrimidine | 186.1-188.5° C. | 1 |
| 5 | 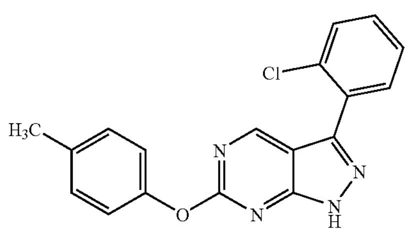 | 3-(2-Chloro-phenyl)-6-p-tolyloxy-1H-pyrazolo[3,4-d]pyrimidine | 177.1-177.8° C. | 1 |
| 6 | 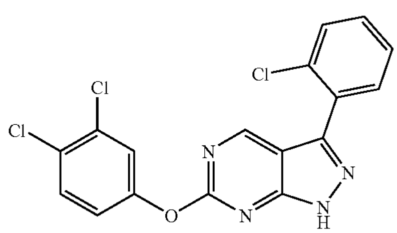 | 3-(2-Chloro-phenyl)-6-(3,4-dichloro-phenoxy)-1H-pyrazolo[3,4-d]pyrimidine | >300° C. | 1 |
| 7 | 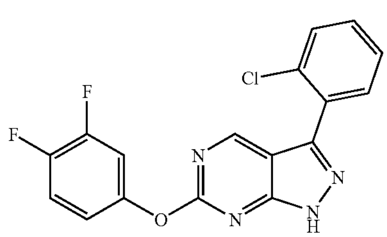 | 3-(2-Chloro-phenyl)-6-(3,4-difluoro-phenoxy)-1H-pyrazolo[3,4-d]pyrimidine | 360 | 1 |

TABLE 1-continued

| # | Structure | Name (Autonom ™) | MP ° C. or M + H | Example |
|---|-----------|------------------|------------------|---------|
| 8 | 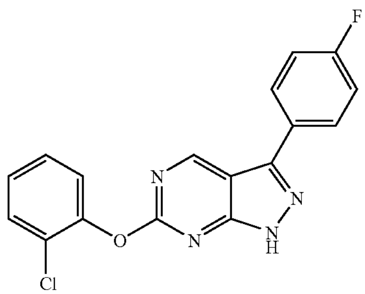 | 6-(2-Fluoro-phenoxy)-3-(4-fluoro-phenyl)-1H-pyrazolo[3,4-d]pyrimidine | 325 | 1 |
| 9 | 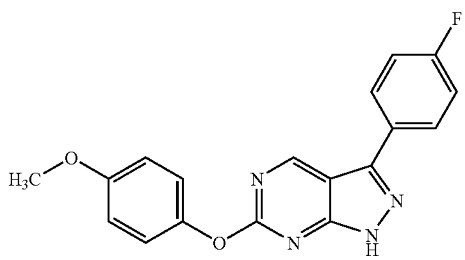 | 3-(4-Fluoro-phenyl)-6-(4-methoxy-phenoxy)-1H-pyrazolo[3,4-d]pyrimidine | 337 | 1 |
| 10 | 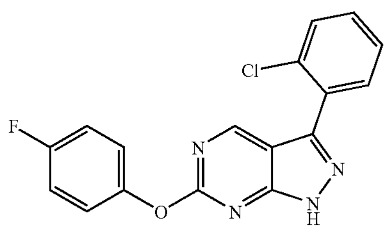 | 3-(2-Chloro-phenyl)-6-(4-fluoro-phenoxy)-1H-pyrazolo[3,4-d]pyrimidine | 200.4-205.9° C. | 1 |
| 11 | 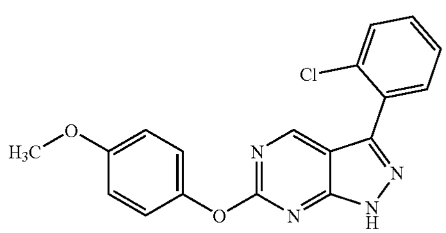 | 3-(2-Chloro-phenyl)-6-(4-methoxy-phenoxy)-1H-pyrazolo[3,4-d]pyrimidine | 145.7-153.4° C. | 1 |
| 12 | 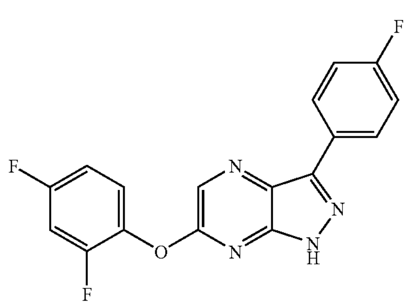 | 6-(2,4-Difluoro-phenoxy)-3-(4-fluoro-phenyl)-1H-pyrazolo[3,4-b]pyrazine | 343 | 5 |

TABLE 1-continued
| # | Structure | Name (Autonom ™) | MP ° C. or M + H | Example |
|---|---|---|---|---|
| 13 | 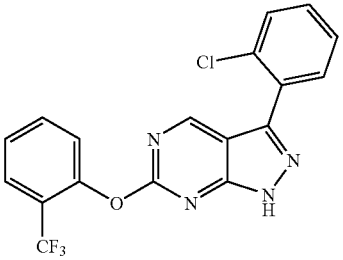 | 3-(2-Chloro-phenyl)-6-(2-trifluoromethyl-phenoxy)-1H-pyrazolo[3,4-d]pyrimidine | 55.3-56.1° C. | 1 |
| 14 | 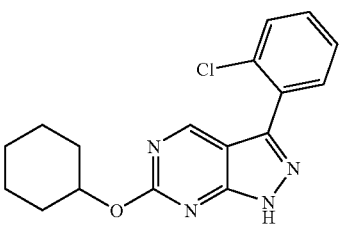 | 3-(2-Chloro-phenyl)-6-cyclohexyloxy-1H-pyrazolo[3,4-d]pyrimidine | 161.4-162.4° C. | 1 |
| 15 | 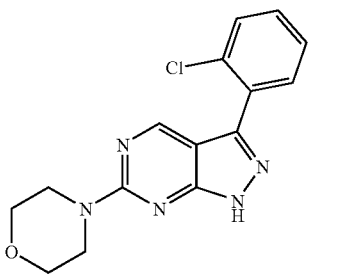 | 3-(2-Chloro-phenyl)-6-morpholin-4-yl-1H-pyrazolo[3,4-d]pyrimidine | 317 | 1 |
| 16 | 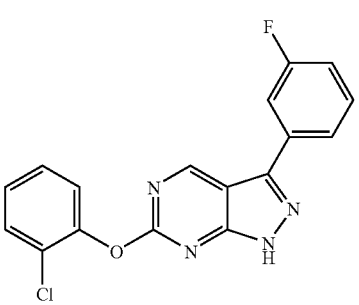 | 6-(2-Chloro-phenoxy)-3-(3-fluoro-phenyl)-1H-pyrazolo[3,4-d]pyrimidine | 209.1-209.5° C. | 15 |
| 17 | 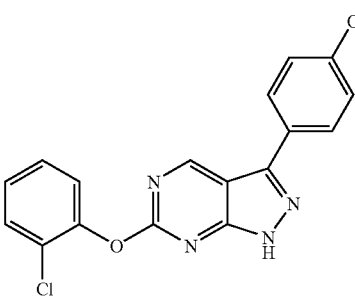 | 6-(2-Chloro-phenoxy)-3-(4-methoxy-phenyl)-1H-pyrazolo[3,4-d]pyrimidine | 215.0-216.5° C. | 15 |

TABLE 1-continued

| # | Structure | Name (Autonom ™) | MP ° C. or M + H | Example |
|---|---|---|---|---|
| 18 | 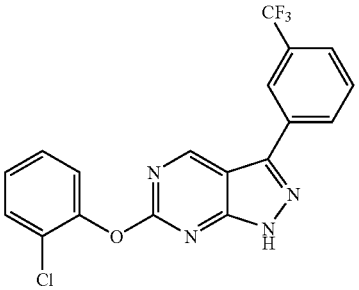 | 6-(2-Chloro-phenoxy)-3-(3-trifluoromethyl-phenyl)-1H-pyrazolo[3,4-d]pyrimidine | 202.3-203.0° C. | 15 |
| 19 | 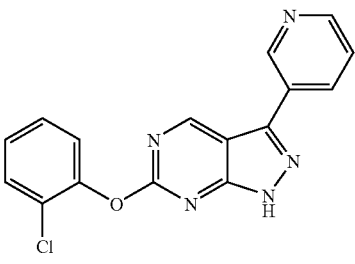 | 6-(2-Chloro-phenoxy)-3-pyridin-3-yl-1H-pyrazolo[3,4-d]pyrimidine | 325 | 15 |
| 20 | 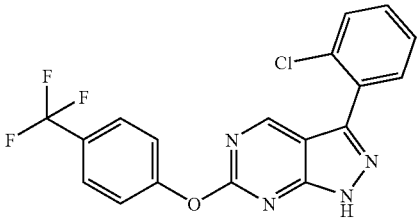 | 3-(2-Chloro-phenyl)-6-(4-trifluoromethyl-phenoxy)-1H-pyrazolo[3,4-d]pyrimidine | 204.8-210.3° C. | 1 |
| 21 | 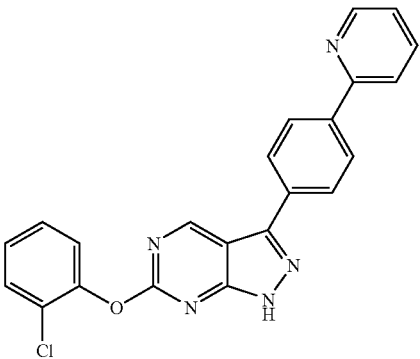 | 6-(2-Chloro-phenoxy)-3-(4-pyridin-2-yl-phenyl)-1H-pyrazolo[3,4-d]pyrimidine | 197.1-217.5° C. | 15 |
| 22 | 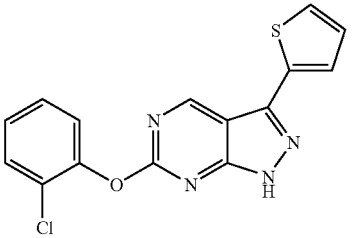 | 6-(2-Chloro-phenoxy)-3-thiophen-2-yl-1H-pyrazolo[3,4-d]pyrimidine | 221.3-223.1° C. | 15 |

TABLE 1-continued

| # | Structure | Name (Autonom ™) | MP ° C. or M + H | Example |
|---|---|---|---|---|
| 23 | 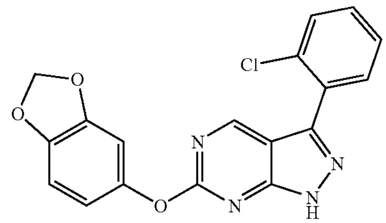 | 6-(Benzo[1,3]dioxol-5-yloxy)-3-(2-chloro-phenyl)-1H-pyrazolo[3,4-d]pyrimidine | 368 | 1 |
| 24 | 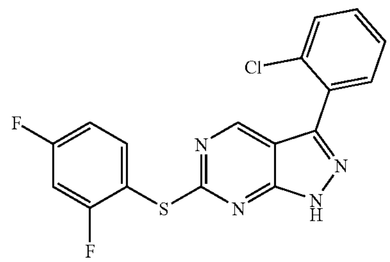 | 3-(2-Chloro-phenyl)-6-(2,4-difluoro-phenylsulfanyl)-1H-pyrazolo[3,4-d]pyrimidine | 177.7-183.2° C. | 3 |
| 25 | 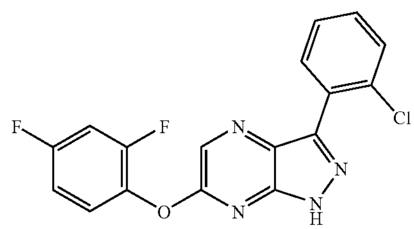 | 3-(2-Chloro-phenyl)-6-(2,4-difluoro-phenoxy)-1H-pyrazolo[3,4-b]pyrazine | 360 | 5 |
| 26 | 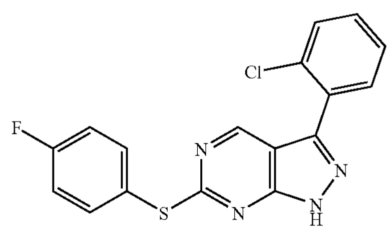 | 3-(2-Chloro-phenyl)-6-(4-fluoro-phenylsulfanyl)-1H-pyrazolo[3,4-d]pyrimidine | 185.6-186.6° C. | 3 |
| 27 | 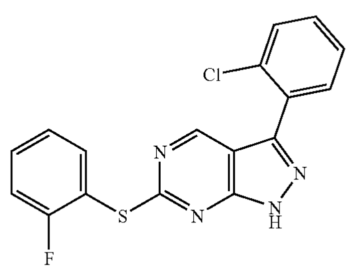 | 3-(2-Chloro-phenyl)-6-(2-fluoro-phenylsulfanyl)-1H-pyrazolo[3,4-d]pyrimidine | 358 | 3 |
| 28 | 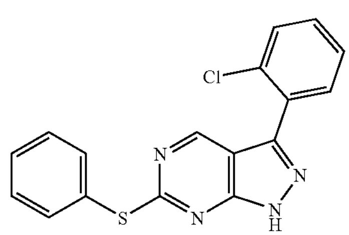 | 3-(2-Chloro-phenyl)-6-phenylsulfanyl-1H-pyrazolo[3,4-d]pyrimidine | 68.1-76.8° C. | 3 |

TABLE 1-continued

| # | Structure | Name (Autonom ™) | MP ° C. or M + H | Example |
|---|---|---|---|---|
| 29 | 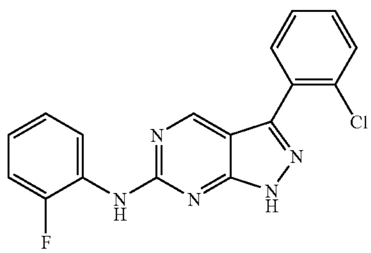 | [3-(2-Chloro-phenyl)-1H-pyrazolo[3,4-d]pyrimidin-6-yl]-(2-fluoro-phenyl)-amine | 230.2-232.4° C. | 2 |
| 30 | 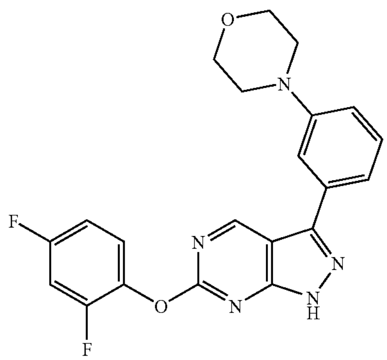 | 6-(2,4-Difluoro-phenoxy)-3-(3-morpholin-4-yl-phenyl)-1H-pyrazolo[3,4-d]pyrimidine | 237.8-238.9° C. | 1 |
| 31 | 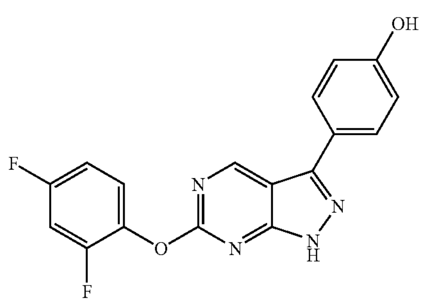 | 4-[6-(2,4-Difluoro-phenoxy)-1H-pyrazolo[3,4-d]pyrimidin-3-yl]-phenol | 341 | 1 |
| 32 | 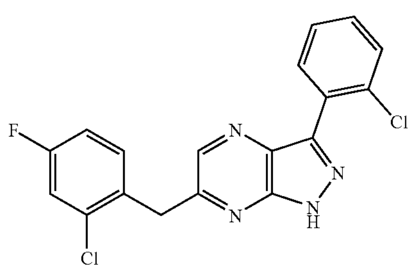 | 6-(2-Chloro-4-fluoro-benzyl)-3-(2-chloro-phenyl)-1H-pyrazolo[3,4-b]pyrazine | 178.3-182.9° C. | 16 |
| 33 | 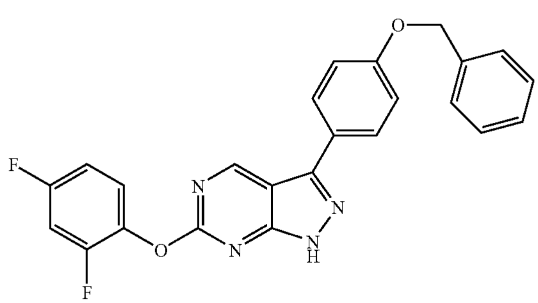 | 3-(4-Benzyloxy-phenyl)-6-(2,4-difluoro-phenoxy)-1H-pyrazolo[3,4-d]pyrimidine | 431 | 1 |

TABLE 1-continued

| # | Structure | Name (Autonom™) | MP °C. or M + H | Example |
|---|---|---|---|---|
| 34 | 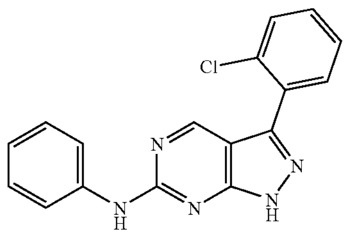 | [3-(2-Chloro-phenyl)-1H-pyrazolo[3,4-d]pyrimidin-6-yl]-phenyl-amine | 323 | 2 |
| 35 | 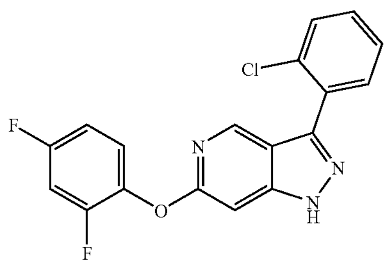 | 3-(2-Chloro-phenyl)-6-(2,4-difluoro-phenoxy)-1H-pyrazolo[4,3-c]pyridine | 359 | 6 |
| 36 | 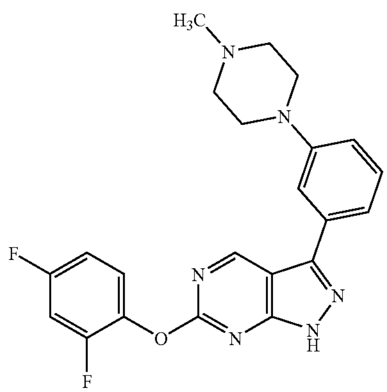 | 6-(2,4-Difluoro-phenoxy)-3-[3-(4-methyl-piperazin-1-yl)-phenyl]-1H-pyrazolo[3,4-d]pyrimidine | 423 | 1 |
| 37 | 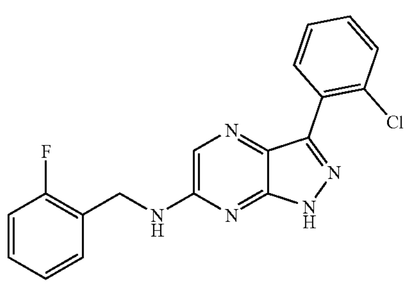 | [3-(2-Chloro-phenyl)-1H-pyrazolo[3,4-b]pyrazin-6-yl]-(2-fluoro-benzyl)-amine | 355 | 5 |
| 38 | 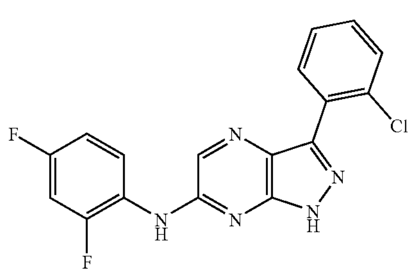 | [3-(2-Chloro-phenyl)-1H-pyrazolo[3,4-b]pyrazin-6-yl]-(2,4-difluoro-phenyl)-amine | 358 | 5 |

TABLE 1-continued

| # | Structure | Name (Autonom ™) | MP ° C. or M + H | Example |
|---|---|---|---|---|
| 39 | 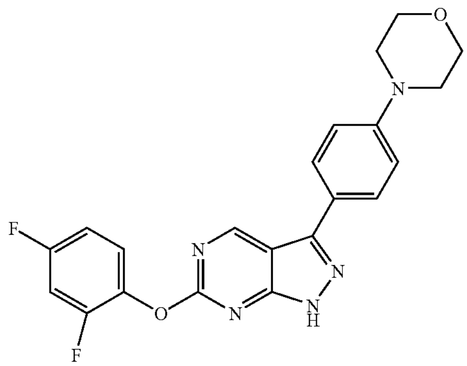 | 6-(2,4-Difluoro-phenoxy)-3-(4-morpholin-4-yl-phenyl)-1H-pyrazolo[3,4-d]pyrimidine | 410 | |
| 40 | 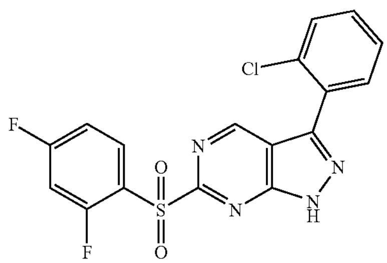 | 3-(2-Chloro-phenyl)-6-(2,4-difluoro-benzenesulfonyl)-1H-pyrazolo[3,4-d]pyrimidine | 408 | 16 |
| 41 | 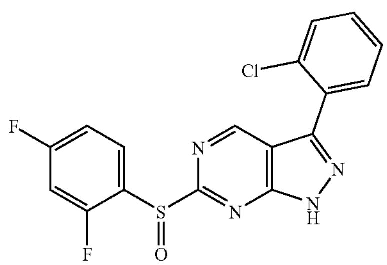 | 3-(2-Chloro-phenyl)-6-(2,4-difluoro-benzenesulfinyl)-1H-pyrazolo[3,4-d]pyrimidine | 392 | 3 |
| 42 | 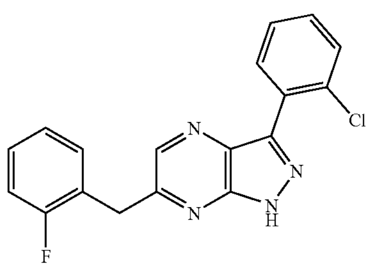 | 3-(2-Chloro-phenyl)-6-(2-fluoro-benzyl)-1H-pyrazolo[3,4-b]pyrazine | 340 | 16 |
| 43 | 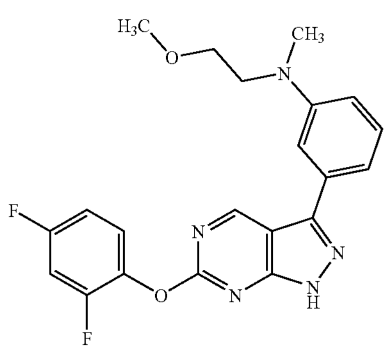 | {3-[6-(2,4-Difluoro-phenoxy)-1H-pyrazolo[3,4-d]pyrimidin-3-yl]-phenyl}-(2-methoxy-ethyl)-methyl-amine | 412 | 1 |

TABLE 1-continued
| # | Structure | Name (Autonom ™) | MP ° C. or M + H | Example |
|---|---|---|---|---|
| 44 | 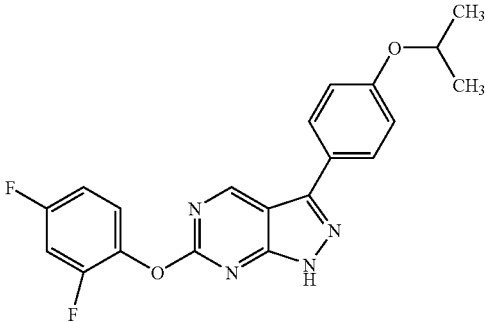 | 6-(2,4-Difluoro-phenoxy)-3-(4-isopropoxy-phenyl)-1H-pyrazolo[3,4-d]pyrimidine | 383 | 1 |
| 45 | 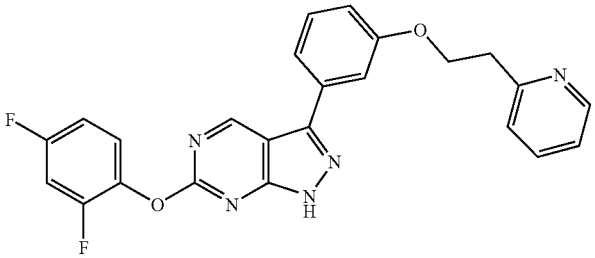 | 6-(2,4-Difluoro-phenoxy)-3-[3-(2-pyridin-2-yl-ethoxy)-phenyl]-1H-pyrazolo[3,4-d]pyrimidine | 446 | 1 |
| 46 | 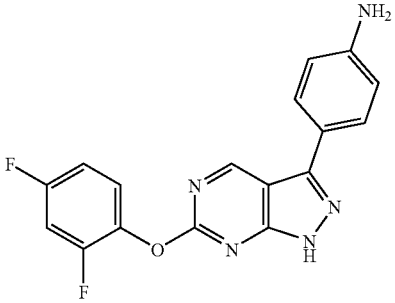 | 4-[6-(2,4-Difluoro-phenoxy)-1H-pyrazolo[3,4-d]pyrimidin-3-yl]-phenylamine | 341 | 1 |
| 47 | 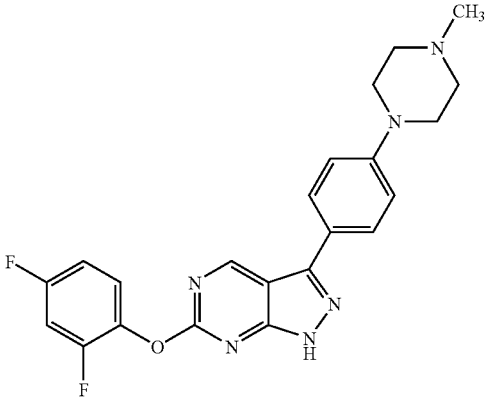 | 6-(2,4-Difluoro-phenoxy)-3-[4-(4-methyl-piperazin-1-yl)-phenyl]-1H-pyrazolo[3,4-d]pyrimidine | 213.3-214.5° C. | 1 |

TABLE 1-continued

| # | Structure | Name (Autonom ™) | MP ° C. or M + H | Example |
|---|---|---|---|---|
| 48 | 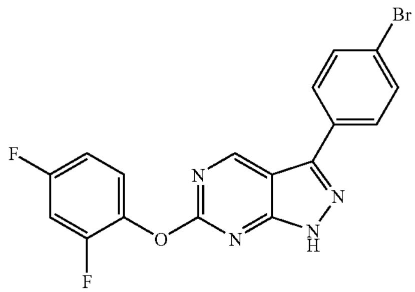 | 3-(4-Bromo-phenyl)-6-(2,4-difluoro-phenoxy)-1H-pyrazolo[3,4-d]pyrimidine | 404 | 1 |
| 49 | 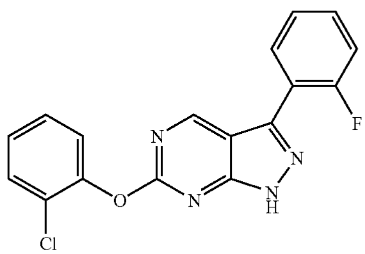 | 6-(2-Chloro-phenoxy)-3-(2-fluoro-phenyl)-1H-pyrazolo[3,4-d]pyrimidine | 192.7-193.4° C. | 1 |
| 50 | 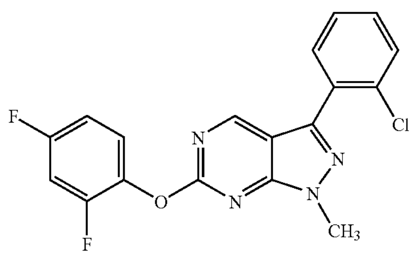 | 3-(2-Chloro-phenyl)-6-(2,4-difluoro-phenoxy)-1-methyl-1H-pyrazolo[3,4-d]pyrimidine | 142.9-146.4° C. | 1 |
| 51 | 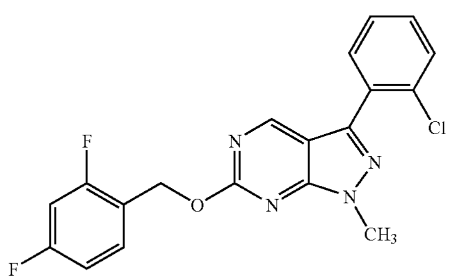 | 3-(2-Chloro-phenyl)-6-(2,4-difluoro-benzyloxy)-1H-pyrazolo[3,4-d]pyrimidine | 201.1-207.3° C. | 1 |
| 52 | 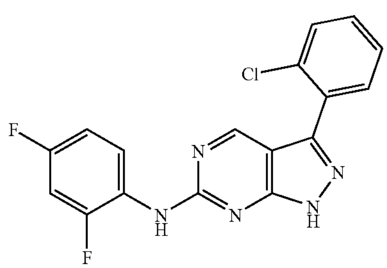 | [3-(2-Chloro-phenyl)-1H-pyrazolo[3,4-d]pyrimidin-6-yl]-(2,4-difluoro-phenyl)-amine | 285.0-285.7° C. | 2 |

TABLE 1-continued

| # | Structure | Name (Autonom ™) | MP ° C. or M + H | Example |
|---|---|---|---|---|
| 53 | 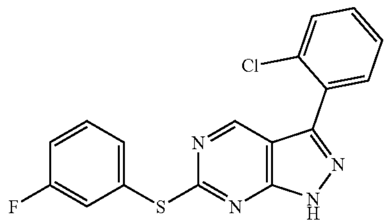 | 3-(2-Chloro-phenyl)-6-(3-fluoro-phenylsulfanyl)-1H-pyrazolo[3,4-d]pyrimidine | 167.7-168.7° C. | 3 |
| 54 | 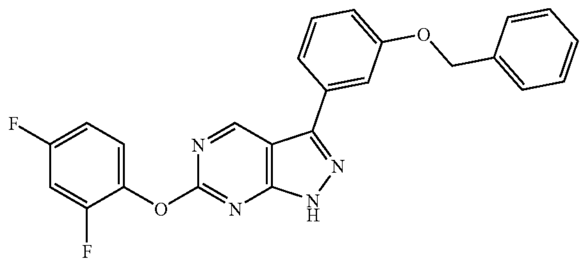 | 3-(3-Benzyloxy-phenyl)-6-(2,4-difluoro-phenoxy)-1H-pyrazolo[3,4-d]pyrimidine | 197.0-197.8° C. | 1 |
| 55 | 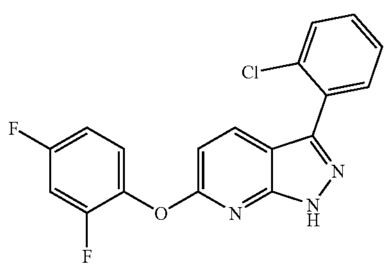 | 3-(2-Chloro-phenyl)-6-(2,4-difluoro-phenoxy)-1H-pyrazolo[3,4-b]pyridine | 359 | 7 |
| 56 | 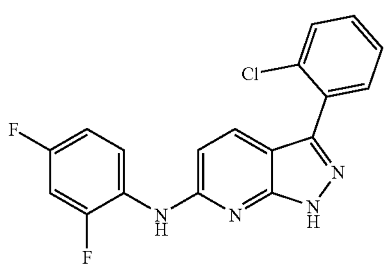 | [3-(2-Chloro-phenyl)-1H-pyrazolo[3,4-b]pyridin-6-yl]-(2,4-difluoro-phenyl)-amine | 358 | 7 |
| 57 | 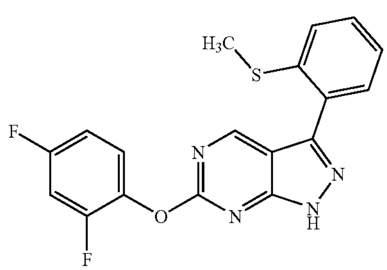 | 6-(2,4-Difluoro-phenoxy)-3-(2-methylsulfanyl-phenyl)-1H-pyrazolo[3,4-d]pyrimidine | 371 | 12 |
| 58 | 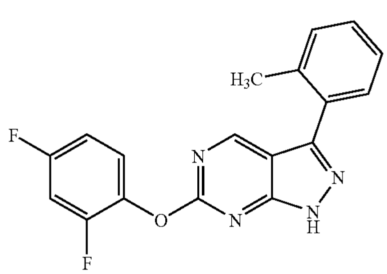 | 6-(2,4-Difluoro-phenoxy)-3-o-tolyl-1H-pyrazolo[3,4-d]pyrimidine | 339 | 12 |

TABLE 1-continued

| # | Structure | Name (Autonom ™) | MP ° C. or M + H | Example |
|---|---|---|---|---|
| 59 | 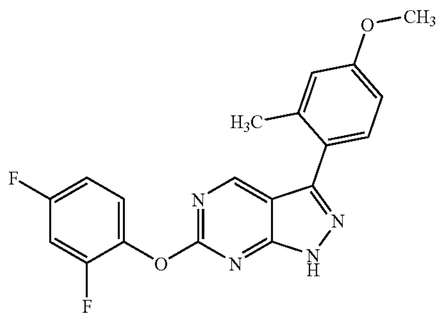 | 6-(2,4-Difluoro-phenoxy)-3-(4-methoxy-2-methyl-phenyl)-1H-pyrazolo[3,4-d]pyrimidine | 369 | 12 |
| 60 | 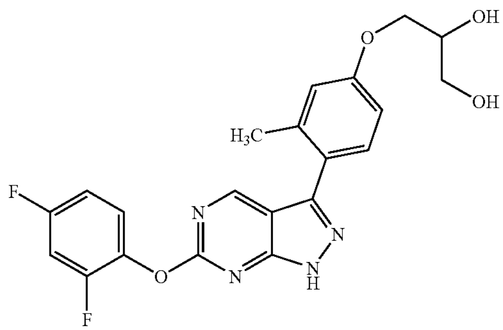 | 3-{4-[6-(2,4-Difluoro-phenoxy)-1H-pyrazolo[3,4-d]pyrimidin-3-yl]-3-methyl-phenoxy}-propane 1,2-diol | 429 | 12 |
| 61 | 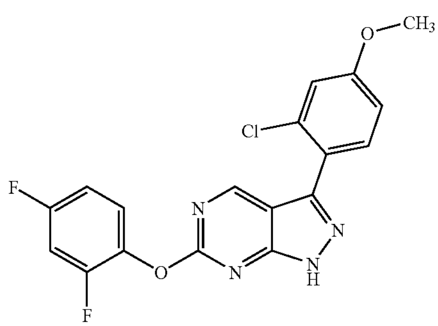 | 3-(2-Chloro-4-methoxy-phenyl)-6-(2,4-difluoro-phenoxy)-1H-pyrazolo[3,4-d]pyrimidine | 390 | 12 |
| 62 | 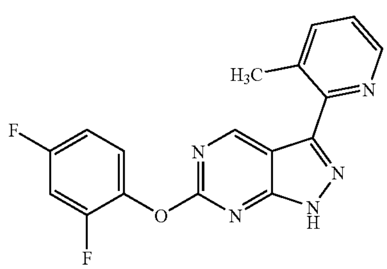 | 6-(2,4-Difluoro-phenoxy)-3-(3-methyl-pyridin-2-yl)-1H-pyrazolo[3,4-d]pyrimidine | 340 | 12 |
| 63 | 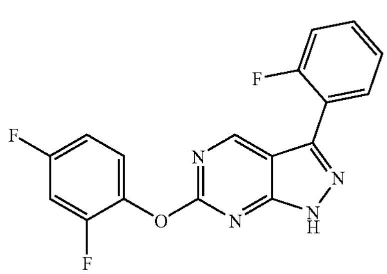 | 6-(2,4-Difluoro-phenoxy)-3-(2-fluoro-phenyl)-1H-pyrazolo[3,4-d]pyrimidine | 343 | 12 |

TABLE 1-continued
| # | Structure | Name (Autonom ™) | MP ° C. or M + H | Example |
|---|---|---|---|---|
| 64 | 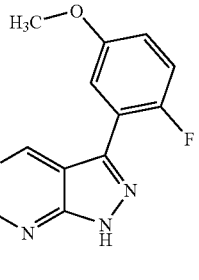 | 6-(2,4-Difluoro-phenoxy)-3-(2-fluoro-5-methoxy-phenyl)-1H-pyrazolo[3,4-d]pyrimidine | 373 | 12 |
| 65 | 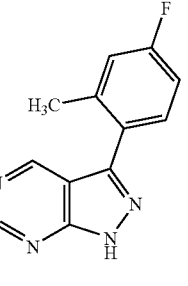 | 6-(2,4-Difluoro-phenoxy)-3-(4-fluoro-2-methyl-phenyl)-1H-pyrazolo[3,4-d]pyrimidine | 357 | 12 |
| 66 | 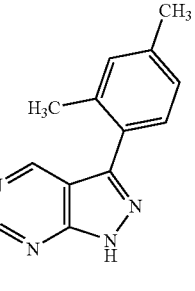 | 6-(2,4-Difluoro-phenoxy)-3-(2,4-dimethyl-phenyl)-1H-pyrazolo[3,4-d]pyrimidine | 353 | 12 |
| 67 | 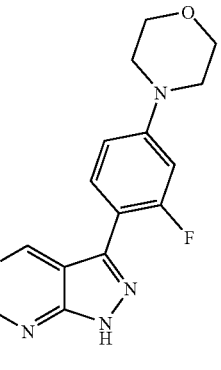 | 6-(2,4-Difluoro-phenoxy)-3-(2-fluoro-4-morpholin-4-yl-phenyl)-1H-pyrazolo[3,4-d]pyrimidine | 428 | 12 |

TABLE 1-continued

| # | Structure | Name (Autonom ™) | MP ° C. or M + H | Example |
|---|---|---|---|---|
| 68 | 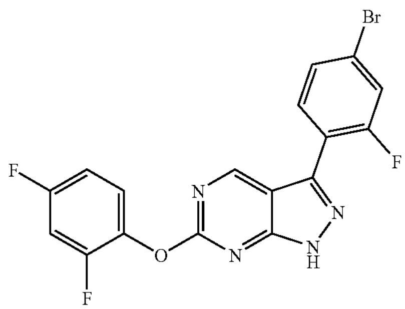 | 3-(4-Bromo-2-fluoro-phenyl)-6-(2,4-difluoro-phenoxy)-1H-pyrazolo[3,4-d]pyrimidine | 422 | 12 |
| 69 | 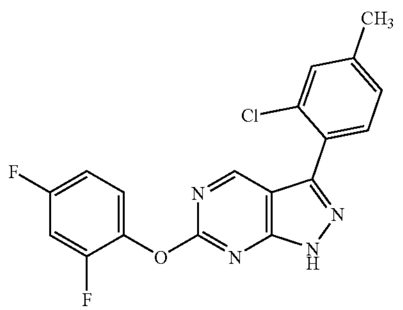 | 3-(2-Chloro-4-methyl-phenyl)-6-(2,4-difluoro-phenoxy)-1H-pyrazolo[3,4-d]pyrimidine | 374 | 12 |
| 70 | 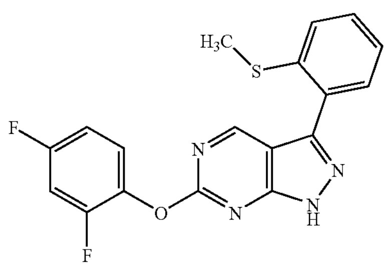 | 6-(2,4-Difluoro-phenoxy)-3-(2-methylsulfanyl-phenyl)-1H-pyrazolo[3,4-d]pyrimidine | 371 | 12 |
| 71 | 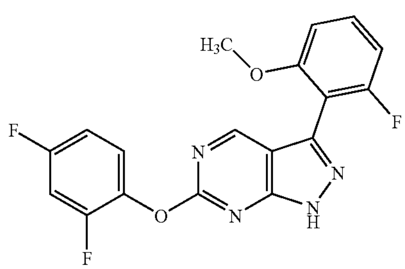 | 6-(2,4-Difluoro-phenoxy)-3-(2-fluoro-6-methoxy-phenyl)-1H-pyrazolo[3,4-d]pyrimidine | 373 | 12 |
| 72 | 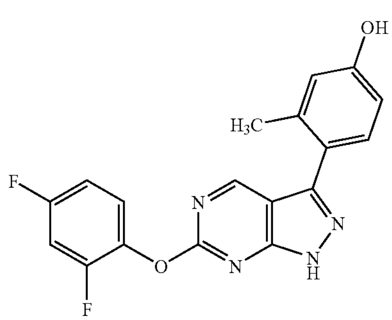 | 4-[6-(2,4-Difluoro-phenoxy)-1H-pyrazolo[3,4-d]pyrimidin-3-yl]-3-methyl-phenol | 355 | 12 |

TABLE 1-continued

| # | Structure | Name (Autonom ™) | MP ° C. or M + H | Example |
|---|---|---|---|---|
| 73 | 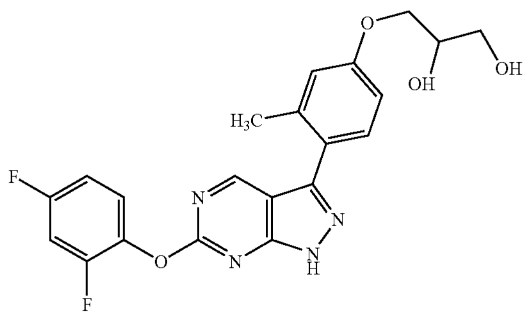 | 3-{4-[6-(2,4-Difluoro-phenoxy)-1H-pyrazolo[3,4-d]pyrimidin-3-yl]-3-methyl-phenoxy}-propane-1,2-diol | 428 | 13 |
| 74 | 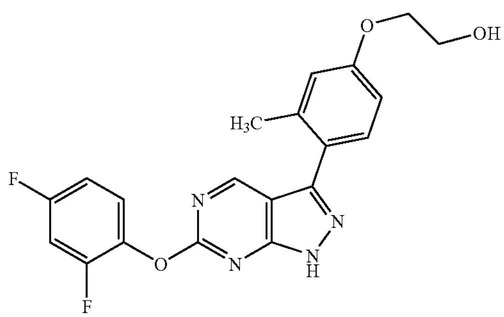 | 2-{4-[6-(2,4-Difluoro-phenoxy)-1H-pyrazolo[3,4-d]pyrimidin-3-yl]-3-methyl-phenoxy}-ethanol | 399 | 13 |
| 75 | 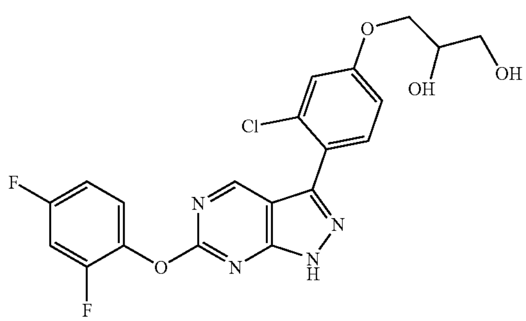 | 3-{3-Chloro-4-[6-(2,4-difluoro-phenoxy)-1H-pyrazolo[3,4-d]pyrimidin-3-yl]-phenoxy}-propane-1,2-diol | 450 | 13 |
| 76 | 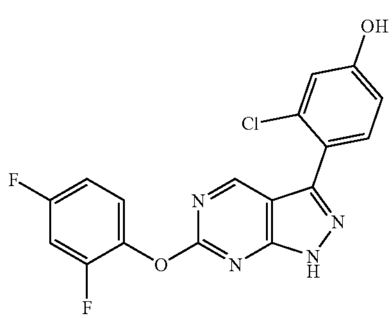 | 3-Chloro-4-[6-(2,4-difluoro-phenoxy)-1H-pyrazolo[3,4-d]pyrimidin-3-yl]-phenol | 376 | 12 |

TABLE 1-continued
| # | Structure | Name (Autonom ™) | MP ° C. or M + H | Example |
|---|---|---|---|---|
| 77 | 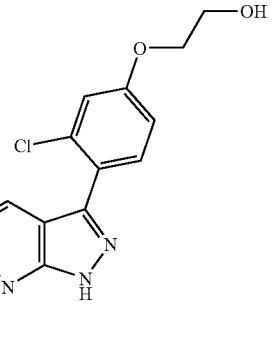 | 2-{3-Chloro-4-[6-(2,4-difluoro-phenoxy)-1H-pyrazolo[3,4-d]pyrimidin-3-yl]-phenoxy}-ethanol | 420 | 13 |
| 78 | 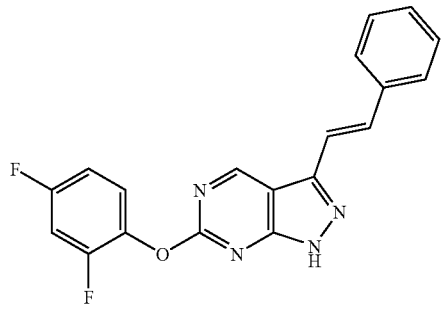 | 6-(2,4-Difluoro-phenoxy)-3-styryl-1H-pyrazolo[3,4-d]pyrimidine | 351 | 14 |
| 79 | 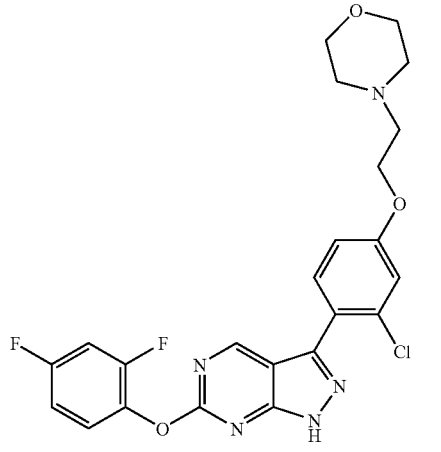 | 3-[2-Chloro-4-(2-morpholin-4-yl-ethoxy)-phenyl]-6-(2,4-difluoro-phenoxy)-1H-pyrazolo[3,4-d]pyrimidine | 489 | 13 |
| 80 | 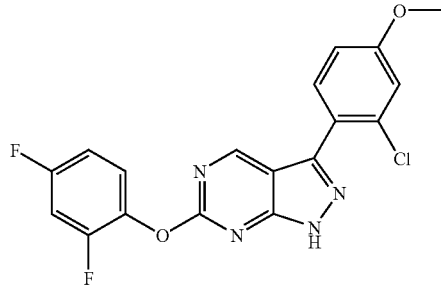 | (2-{3-Chloro-4-[6-(2,4-difluoro-phenoxy)-1H-pyrazolo[3,4-d]pyrimidin-3-yl]-phenoxy}-ethyl)-dimethyl-amine | 447 | 13 |

TABLE 1-continued

| # | Structure | Name (Autonom™) | MP °C. or M + H | Example |
|---|---|---|---|---|
| 81 | 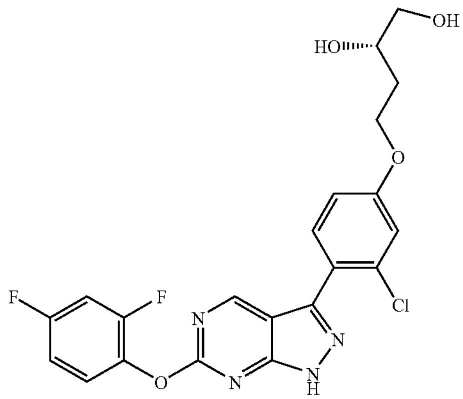 | 4-{3-Chloro-4-[6-(2,4-difluoro-phenoxy)-1H-pyrazolo[3,4-d]pyrimidin-3-yl]-phenoxy}-butane-1,2-diol | 464 | 13 |
| 82 | 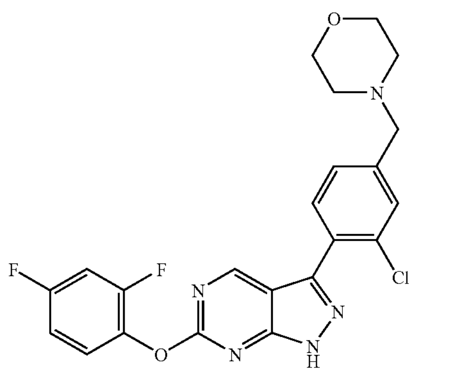 | 3-(2-Chloro-4-morpholin-4-ylmethyl-phenyl)-6-(2,4-difluoro-phenoxy)-1H-pyrazolo[3,4-d]pyrimidine | 459 | 13 |
| 83 | 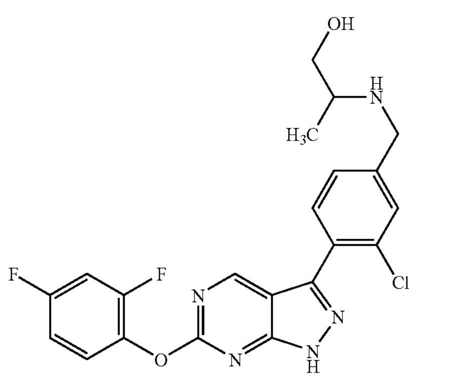 | 2-{3-Chloro-4-[6-(2,4-difluoro-phenoxy)-1H-pyrazolo[3,4-d]pyrimidin-3-yl]-benzylamino}-propan-1-ol | 447 | 12 |
| 84 | 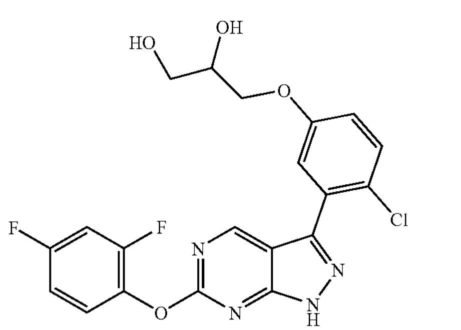 | 3-{4-Chloro-3-[6-(2,4-difluoro-phenoxy)-1H-pyrazolo[3,4-d]pyrimidin-3-yl]-phenoxy}-propane-1,2-diol | 450 | 12 |

TABLE 1-continued

| # | Structure | Name (Autonom ™) | MP ° C. or M + H | Example |
|---|---|---|---|---|
| 85 | 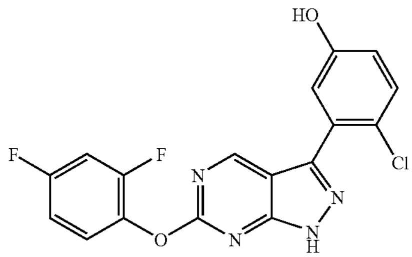 | 4-Chloro-3-[6-(2,4-difluoro-phenoxy)-1H-pyrazolo[3,4-d]pyrimidin-3-yl]-phenol | 376 | 12 |
| 86 | 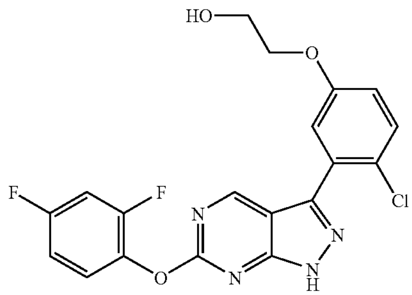 | 2-{4-Chloro-3-[6-(2,4-difluoro-phenoxy)-1H-pyrazolo[3,4-d]pyrimidin-3-yl]-phenoxy}-ethanol | 420 | 12 |
| 87 | 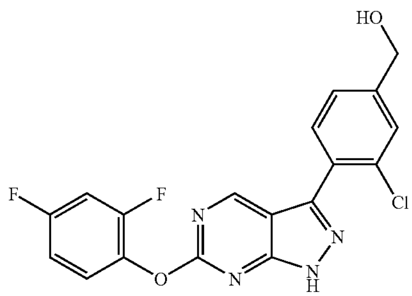 | {3-Chloro-4-[6-(2,4-difluoro-phenoxy)-1H-pyrazolo[3,4-d]pyrimidin-3-yl]-phenyl}-methanol | 390 | 12 |
| 88 | 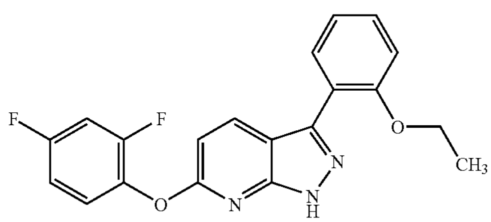 | 6-(2,4-Difluoro-phenoxy)-3-(2-ethoxy-phenyl)-1H-pyrazolo[3,4-b]pyridine | 368 | 7 |
| 89 | 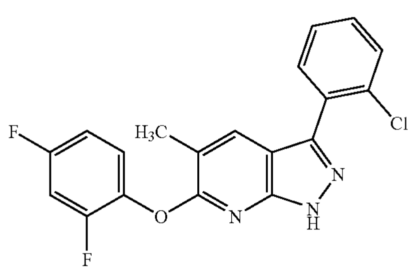 | 3-(2-Chloro-phenyl)-6-(2,4-difluoro-phenoxy)-5-methyl-1H-pyrazolo[3,4-b]pyridin | 373 | 7 |
| 90 | 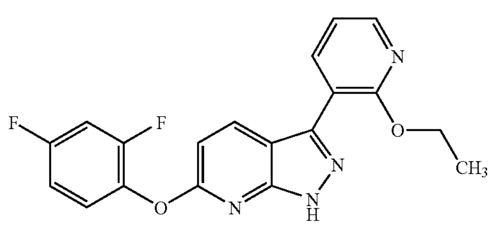 | 6-(2,4-Difluoro-phenoxy)-3-(2-ethoxy-pyridin-3-yl)-1H-pyrazolo[3,4-b]pyridine | 369 | 7 |

TABLE 1-continued

| # | Structure | Name (Autonom ™) | MP ° C. or M + H | Example |
|---|---|---|---|---|
| 91 | 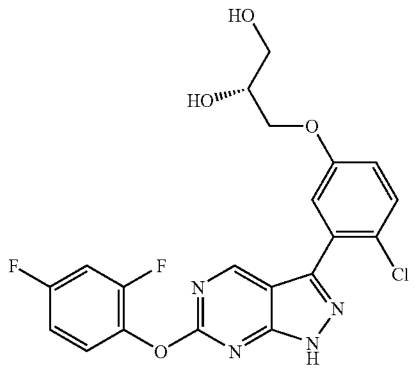 | 3-{4-Chloro-3-[6-(2,4-difluoro-phenoxy)-1H-pyrazolo[3,4-d]pyrimidin-3-yl]-phenoxy}-propane-1,2-diol | 450 | 13 |
| 92 | 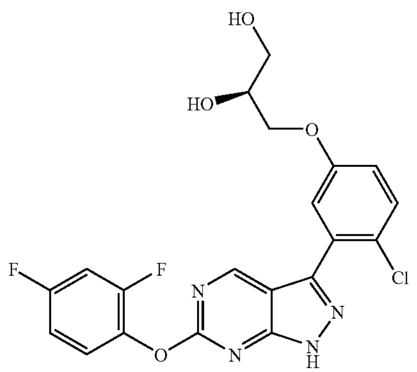 | 3-{4-Chloro-3-[6-(2,4-difluoro-phenoxy)-1H-pyrazolo[3,4-d]pyrimidin-3-yl]-phenoxy}-propane-1,2-diol | 450 | 13 |
| 93 | 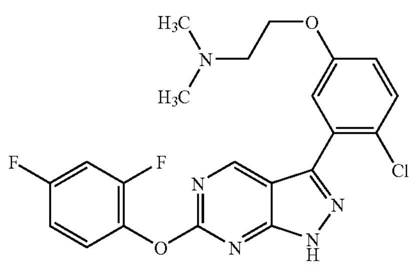 | (2-{4-Chloro-3-[6-(2,4-difluoro-phenoxy)-1H-pyrazolo[3,4-d]pyrimidin-3-yl]-phenoxy}-ethyl)-dimethyl-amine | 447 | 13 |
| 94 | 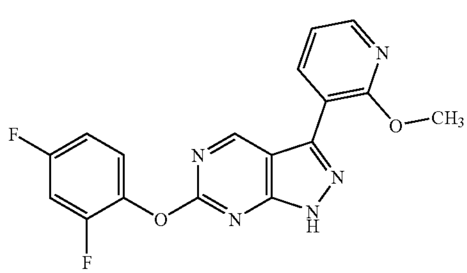 | 6-(2,4-Difluoro-phenoxy)-3-(2-methoxy-pyridin-3-yl)-1H-pyrazolo[3,4-d]pyrimidine | 356 | 12 |
| 95 | 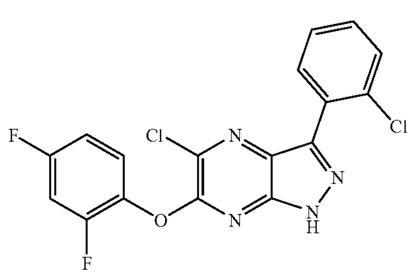 | 5-Chloro-3-(2-chloro-phenyl)-6-(2,4-difluoro-phenoxy)-1H-pyrazolo[3,4-b]pyrazine | 394 | 5 |

TABLE 1-continued

| # | Structure | Name (Autonom ™) | MP ° C. or M + H | Example |
|---|---|---|---|---|
| 96 | 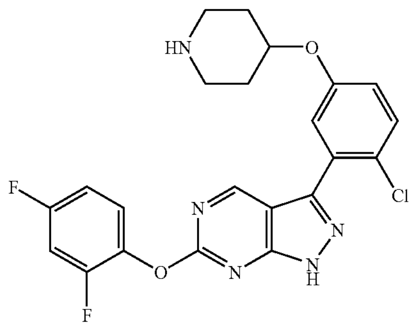 | 3-[2-Chloro-5-(piperidin-4-yloxy)-phenyl]-6-(2,4-difluoro-phenoxy)-1H-pyrazolo[3,4-d]pyrimidine | 459 | 13 |
| 97 | 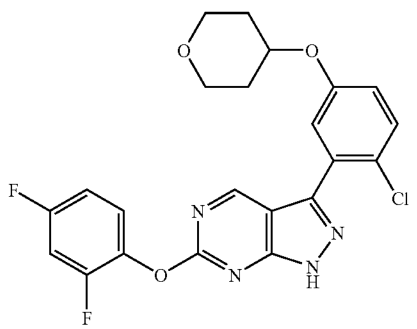 | 3-[2-Chloro-5-(tetrahydro-pyran-4-yloxy)-phenyl]-6-(2,4-difluoro-phenoxy)-1H-pyrazolo[3,4-d]pyrimidine | 460 | 13 |
| 98 | 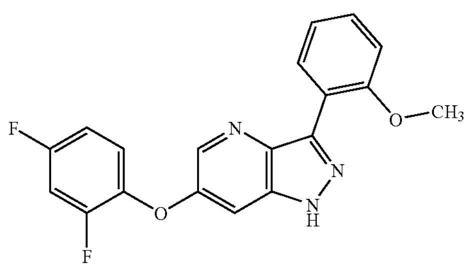 | 6-(2,4-Difluoro-phenoxy)-3-(2-methoxy-phenyl)-1H-pyrazolo[4,3-b]pyridine | 354 | 8 |
| 99 | 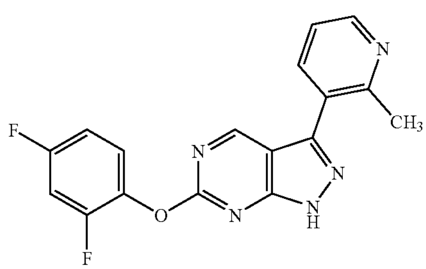 | 6-(2,4-Difluoro-phenoxy)-3-(2-methyl-pyridin-3-yl)-1H-pyrazolo[3,4-d]pyrimidine | 340 | 12 |
| 100 | 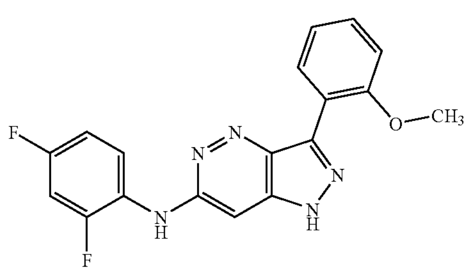 | (2,4-Difluoro-phenyl)-[3-(2-methoxy-phenyl)-1H-pyrazolo[4,3-c]pyridazin-6-yl]-amine | 354 | 9 |

TABLE 1-continued

| # | Structure | Name (Autonom ™) | MP ° C. or M + H | Example |
|---|---|---|---|---|
| 101 | 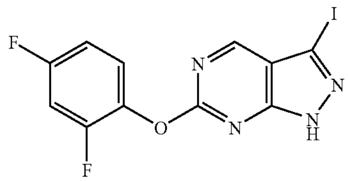 | 6-(2,4-Difluoro-phenoxy)-3-iodo-1H-pyrazolo[3,4-d]pyrimidine | 375 | 11 |
| 102 | 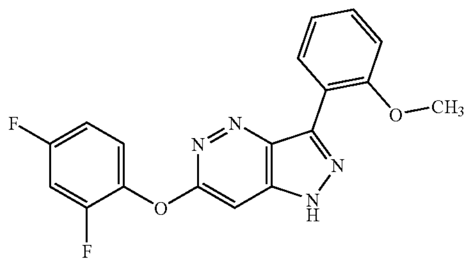 | 6-(2,4-Difluoro-phenoxy)-3-(2-methoxy-phenyl)-1H-pyrazolo[4,3-c]pyridazine | 355 | 9 |
| 103 | 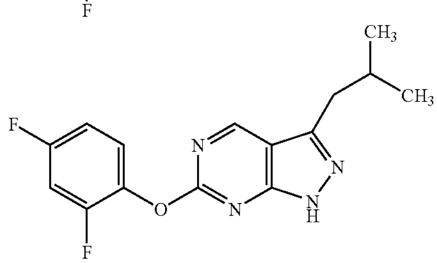 | 6-(2,4-Difluoro-phenoxy)-3-isobutyl-1H-pyrazolo[3,4-d]pyrimidine | 305 | 10 |
| 104 | 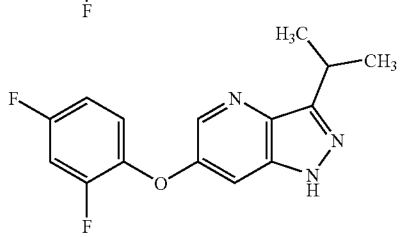 | 6-(2,4-Difluoro-phenoxy)-3-isopropyl-1H-pyrazolo[4,3-b]pyridine | 291 | 8 |
| 105 | 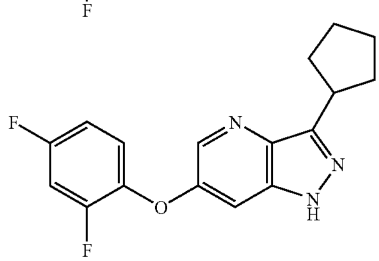 | 3-Cyclopentyl-6-(2,4-difluoro-phenoxy)-1H-pyrazolo[4,3-b]pyridine | 317 | 8 |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

One of the specific methods for preparing some of the Compounds of Formula I is shown in Scheme I below.

Scheme I

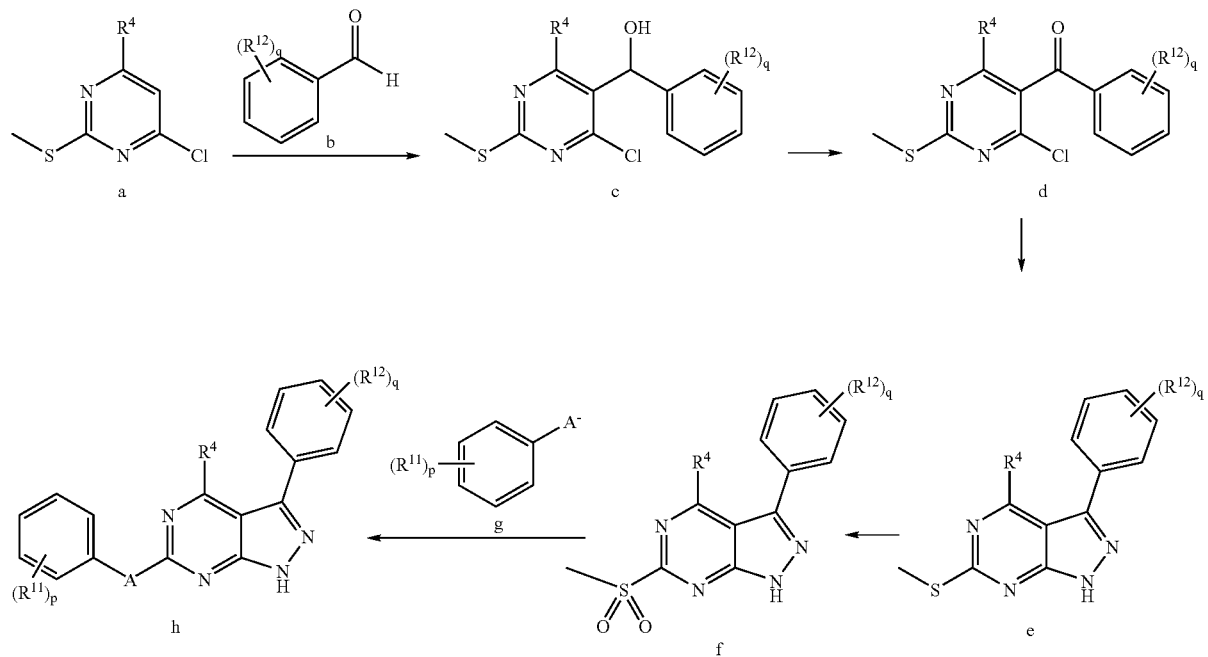

In Scheme I, a chlorothiopyrimidine a is deprotonated using a base, such as lithium diisopropylamide (LDA) or other suitable bases that are well known to one skilled in the art. The deprotonated pyrimidine a is reacted with a benzaldehyde b or its derivative to produce an alcohol c. This alcohol c is oxidized, e.g., by manganese oxide, to produce a pyrimidine phenyl ketone d. Reacting the ketone d with hydrazine affords a ring closure product in the form of a pyrazolopyrimidine e. The thio group on pyrazolopyrimidine e is oxidized, e.g., with Oxone, meta-chloroperbenzoic acid, or other oxidizing agents known to one skilled in the art, to produce a sulfonyl pyrazolopyrimidine derivative f. The sulfonyl group on pyrazolopyrimidine derivative f is then displaced with a nucleophilic aryl group g, such as an optionally substituted phenoxide or an optionally substituted thiophenoxide, to produce a variety of compounds of formula I.

Another method for producing a compound of formula I is shown in Scheme II below. In this method, the starting material is an acetophenone i, e.g., such as chloroacetophenone, or its derivative. In Scheme II, acetophenone i is deprotonated using a base, such as sodium hydride or other suitable base known to one skilled in the art. Deprotonated acetophenone i is reacted with with a dialkyl carbonate (not shown), e.g., dimethyl carbonate, to provides a condensation product such as a β-ketoester compound i. The β-ketoester compound j is then reacted with an orthoester (not shown), e.g., triethylorthoformate, in the presence of an anhydride (not shown), e.g., acetic anhydride, to yield an acrylate derivative k. To form a pyrimidine ring, the acrylate derivative k is reacted with a thiourea (not shown) in the presence of a base, such as an alkoxide, followed by alkylation with methyl iodide, to form thiopyrimidine 1. The thiopyrimidine 1 is then treated with phosphorous oxychloride to provide an (alkylsulfanyl hydroxy)pyrimidine chlorophenyl ketone d. This ketone d is then converted to a compound h using the procedure shown in Scheme I above.

Scheme II

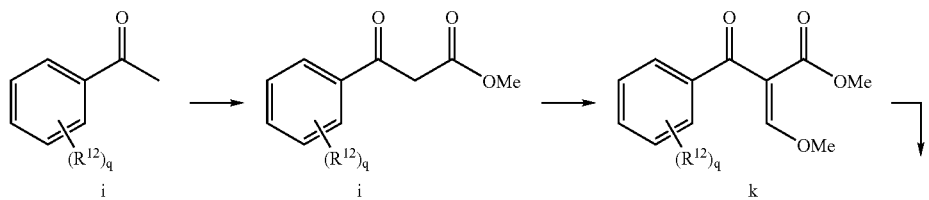

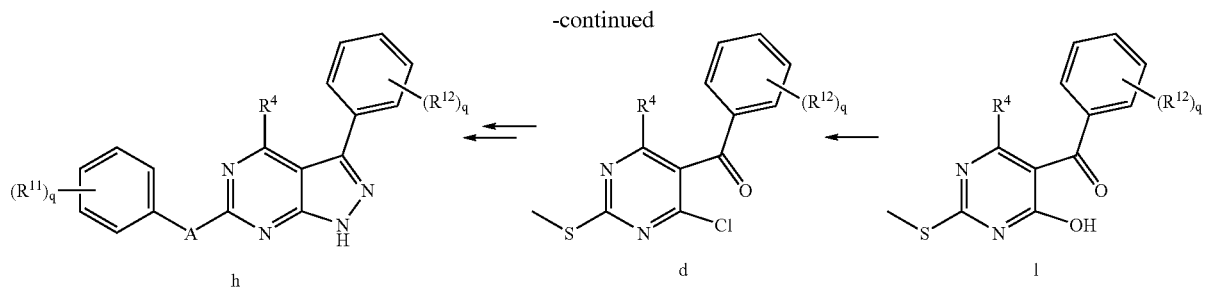

Pyrazolopyrazine derivatives of formula I may be prepared as shown in Scheme III. A pyrazine derivative o, such as a dihalopyrazine compound like 2,6-dichloropyrazine, may be deprotonated using a strong base. Suitable bases for deprotonation of pyrazine include bases that are suitable in deprotonation of pyrimidine, which are discussed above. Typically, a metal amide compound, such as a lithium amide compound, preferably a sterically hindered base, e.g., LiTMP, is used in the deprotonation reaction. Lithium amide bases, such as lithium 2,2,6,6-tetramethylpiperidine (LiTMP) or LDA, are generated by reacting the corresponding amine compound with an alkyllithium compound. Suitable reaction conditions for generating lithium amide bases are well known to one skilled in the art.

The deprotonated pyrazine (not shown) may then be reacted with a benzaldehyde p or its derivative, depending on the desired substituents on the phenyl ring moiety, to afford a pyrazine phenylmethyl alcohol g. This secondary alcohol q is oxidized to a pyrazine phenyl ketone compound r. Suitable oxidizing agents for converting an alcohol to a carbonyl moiety are well known to one skilled in the art. Exemplary oxidizing agents include manganese (IV) oxide and chromium based compounds (such as PCC, PDC, and chromium trioxide). In addition, other oxidation conditions, such as Swern oxidation conditions, can be used to generate the ketone from the alcohol.

After the oxidation reaction, the ketone r is reacted with a suitable nucleophilic compound, such as a thiophenoxide or a phenoxide compound s, to displace one of the chloro group on the pyrazine ring moiety and for phenoxy pyrazolo ketone t. Formation of the pyrazoline ring moiety to afford compound u is achieved by reacting the ketone u with hydrazine in a manner similar to that described above in Scheme I above.

Scheme III

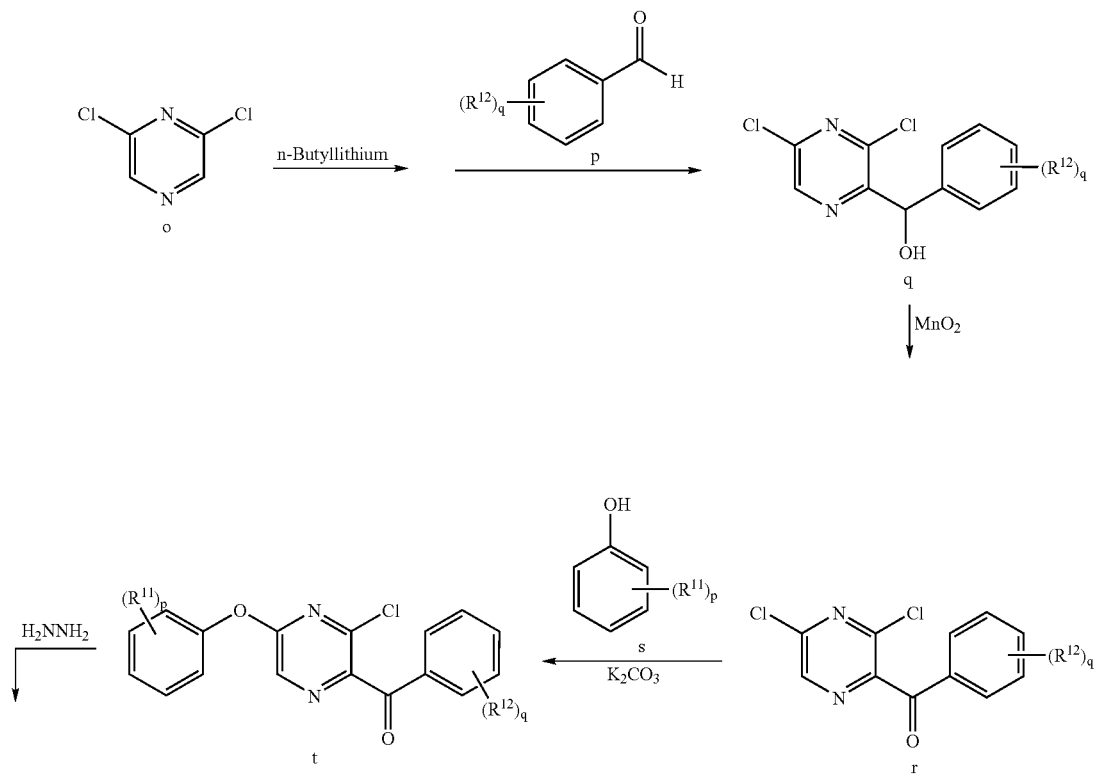

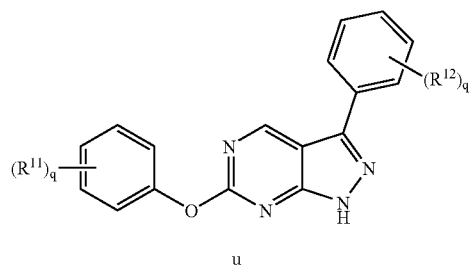
u

Pyrazolopyridine derivatives of formula I may be prepared according to Scheme IV shown below. In this strategy, the nitrogen atom of pyridine compound v is oxidized using any one of the suitable oxidizing agents known to one skilled in the art, e.g., hydrogen peroxide in acetic acid, to form pyridine-N-oxide w. Nitration of the pyridine oxide compound w under typical nitration reaction conditions affords a 4-nitropyridine oxide compound x. Substitution reaction of this nitropyridine oxide compound x with an aryl or heteroaryl nucleophile, e.g., a phenoxide derivative y (or other aryl- or heteroaryloxide, aryl- or heteroarylamine, or aryl- or heteroarylthiophenoxide), affords a nitrophenoxy substituted pyridine oxide compound z.

Reduction of the nitro group of compound z via hydrogenation affords an aminopyridine N-oxide aa, the N-oxide moiety of which may be reduced with phosphorous trichloride to give an aminopyridine compound bb. Protection of the amino group, e.g., with an acetyl group gives a protected aminopyridine cc, which may then be treated with acetic anhydride under mild basic conditions to achieve formation of pyrazoline ring system and afford a pyrazolopyridine compound dd. Suitable reagents and reaction conditions for formation of pyrazoline ring moiety are well known to one skilled in the art. Only one particular set of reagents and reaction conditions is provided in Scheme IV.

The pyrazolopyridine compound dd can be further modified by removing the acetyl group from the pyrazoline nitrogen atom to yield an unprotected pyrazolopyridine ee. Iodination pyrazolopyridine ee yields iodopyrazolopyridine ff, which may then be protected, e.g., with a BOC group to yield protected iodopyrazolopyridine gg. Iodopyrazolopyridine gg may then be cross-coupled with an aryl- or heteroaryl group hh to yield protected pyrazolopyridine ii, which in turn may be deprotected to yield pyrazolopyridine compound jj.

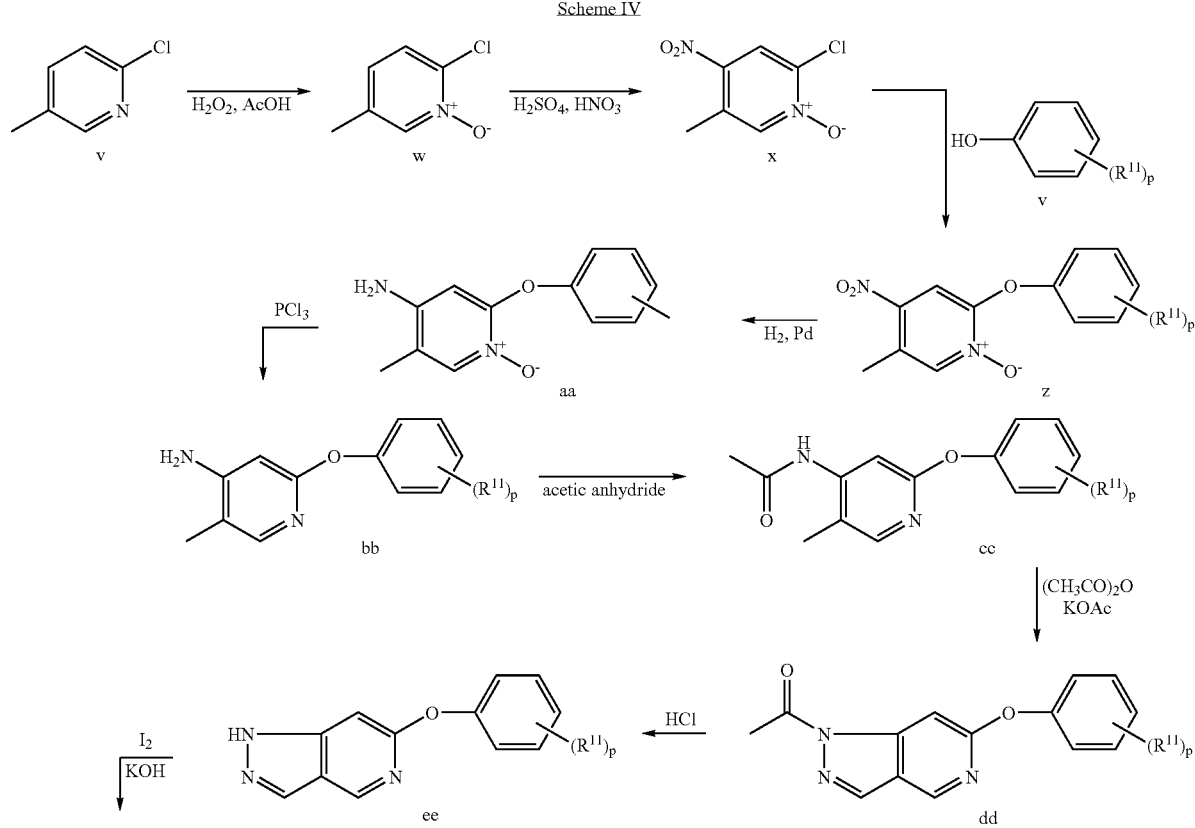

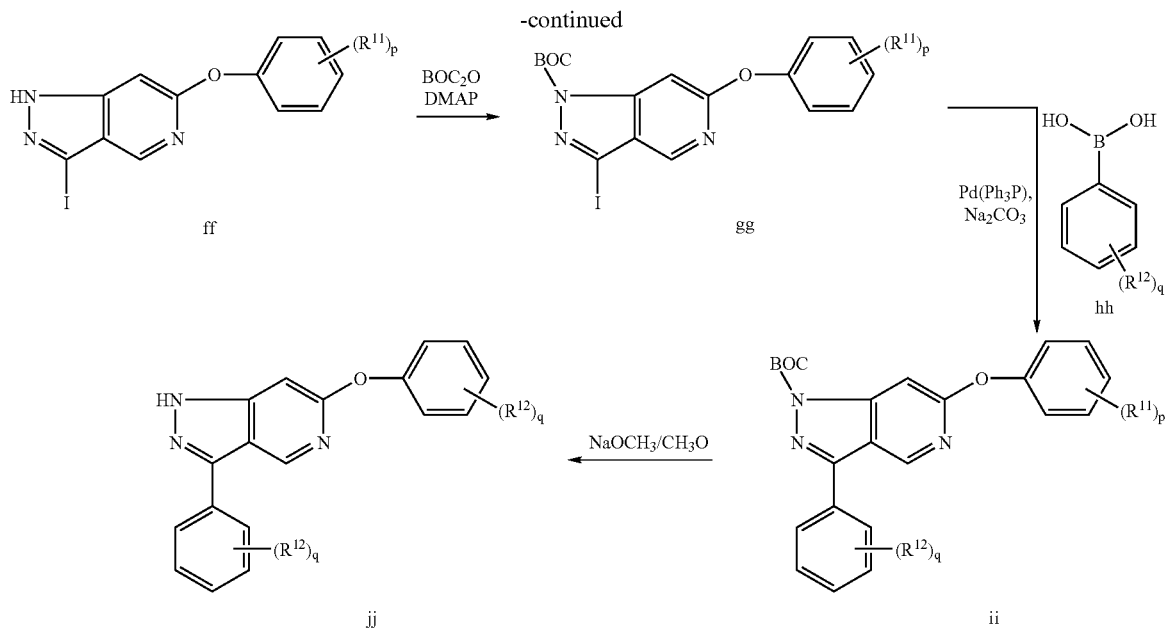

One of skill in the art will understand that certain modifications to the above schemes are contemplated and within the scope of the present invention. For example, certain steps will involve the use of protecting groups for functional groups that are not compatible with particular reaction conditions.

Scheme V below illustrates yet another procedure for preparing specific compounds of the invention, wherein Ha is halo and may be the same or different in each occurrence, and q, X, Y, Z, $R^2$ and $R^{11}$ are as defined herein.

SCHEME V

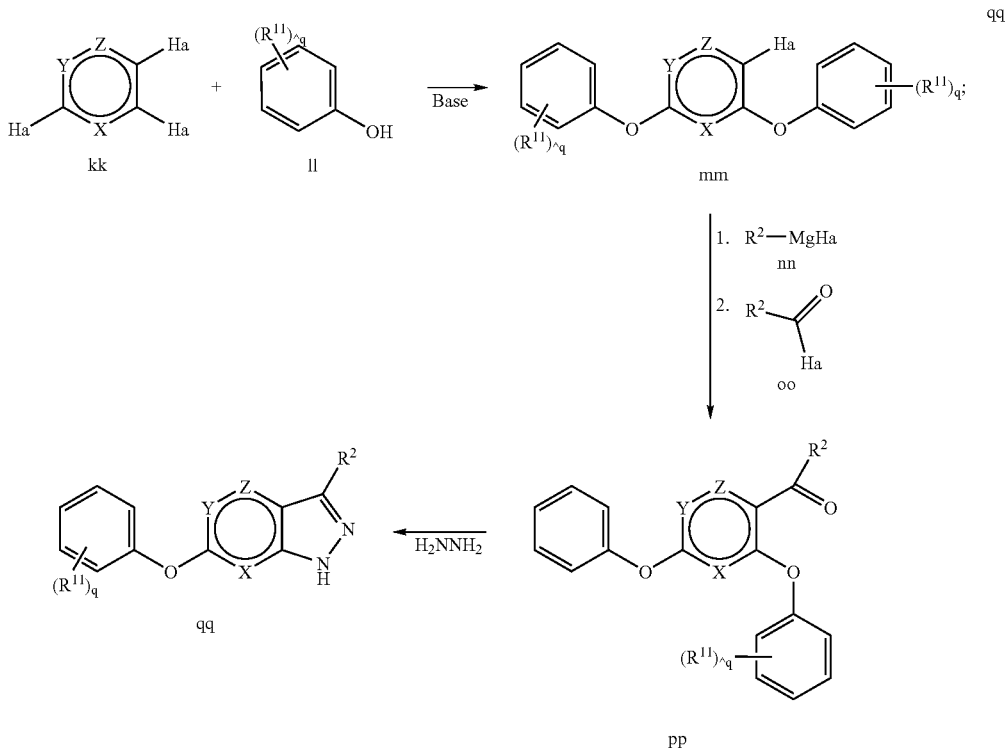

In Scheme V, compound kk is treated with phenol ll in the presence of base to yield phenoxy compound mm. The halo substituents of compound kk may be selected as desired according to different aza substitutions. Phenoxy compound mm is then reacted first with Grignard reagent nn, followed by acyl halide oo, to afford acylated phenoxy compound pp. Compound pp may then be reacted with hydrazine to form compound qq, which is a compound of formula I (where $R^1$ is optionally substituted phenyl, k is 0, and A is O) in accordance wtih the invention.

More specific details for producing compounds of formula (I) are described in the Examples section below.

Pharmaceutical Compositions and Administration

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in the Examples below.

Utility

Compounds of the invention are useful for, but not limited to, the treatment of any disorder or disease state in a human, or other mammal, which is exacerbated or caused by excessive or unregulated TNF or p38 kinase production by such mammal. Accordingly, the present invention provides a method of treating a p38-mediated disease which comprises administering an effective amount of a compound of the invention, or a pharmaceutically acceptable salt, solvate or prodrug thereof, to a subject or patient in need thereof.

Compounds of the invention are useful for, but not limited to, the treatment of inflammation in a subject, and for use as antipyretics for the treatment of fever. Compounds of the invention would be useful to treat arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions. Such compounds would be useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. The compounds are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds are also useful for the treatment of Alzheimer's disease, influenza, multiple sclerosis, cancer, diabetes, systemic lupus erthrematosis (SLE), skin-related conditions such as psoriasis, eczema, burns, dermatitis, keloid formation, and scar tissue formation. In addition, compounds of the invention are useful in treating gastrointestinal conditions such as inflammatory bowel disease, Crohn's disease, gastritis, irritable bowel syndrome and ulcerative colitis. The compounds are also useful in the treatment of ophthalmic diseases, such as retinitis, retinopathies, uveitis, ocular photophobia, and of acute injury to the eye tissue. The compounds can also be used in treating angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma, ulcerative diseases such as gastric ulcer, pathological, but non-malignant, conditions such as hemangiomas, including infantile hemangiomas, angiofibroma of the nasopharynx and avascular necrosis of bone, diabetic nephropathy and cardiomyopathy, and disorders of the female reproductive system such as endometriosis. The compounds can further be used for preventing the production of cyclooxygenase-2 and have analgesic properties. Therefore, Compounds of Formula I are useful for treatment of pain.

Other uses for Compounds of Formula I include treatment of HCV, severe asthma, psoriasis, chronic obstructive pulmonary disease (COPD), and other diseases that can be treated with an anti-TNF compound.

Besides being useful for human treatment, these compounds are also useful for veterinary treatment of companion animals, exotic animals and farm animals, including mammals, rodents, and the like. More preferred animals include horses, dogs, and cats.

The present compounds can also be used in co-therapies, partially or completely, in place of other conventional antiinflammatories, such as together with steroids, cyclooxygenase-2 inhibitors, NSAIDs, DMARDS, immunosuppressive agents, 5-lipoxygenase inhibitors, $LTB_4$ antagonists and $LTA_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Examples.

ABBREVIATIONS

DCM dichloromethane
DMF N,N-dimethylformamide
DMAP 4-dimethylaminopyridine
gc gas chromatography
HMPA hexamethylphosphoramide
hplc high performance liquid chromatography
mCPBA m-chloroperbenzoic acid
MeCN acetonitrile
TEA triethylamine
THF tetrahydrofuran
LDA lithium diisopropylamine
TLC thin layer chromatography Example 1

This example illustrates a synthesis of 3-(2-chlorophenyl)-6-(2,4-difluoro-phenoxy)-1H-pyrazolo[3,4-d]pyrimidine following the procedure of Scheme I above.

Step 1. Preparation of (4-chloro-2-methylsulanyl-pyrimidin-5-yl)-(2-chloropheny)-methanol.

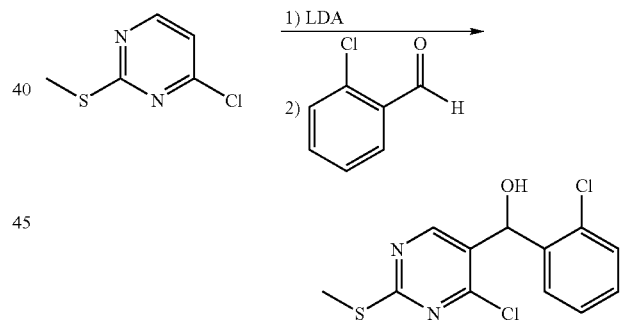

To a solution of 4-chloro-2-(methylthio)pyrimidine (Aldrich) (20 g, 124.51 mmol) in dry THF (300 mL) at −78° C. under argon was slowly added a solution of 2.0 M lithium diisopropyl amide, i.e., LDA, (109 mL, 1.75 eq) in THF via a cannula. After addition was complete, the resulting mixture was stirred at −78° C. for an additional 15 minutes, after which 2-chlorobenzaldehyde (Aldrich) (29.5 mL, 2.1 eq) was added dropwise via syringe. The reaction mixture was stirred for an additional 30 minutes at −78° C. and then quenched with saturated ammonium chloride solution. Ethyl acetate was added, the mixture was allowed to warm to room temperature, and the layers were partitioned and separated. The aqueous layer was extracted with ethyl acetate, and the combined organic layers were washed with brine solution. The ethyl acetate layers were combined, dried over magnesium sulfate, filtered and concentrated to give the crude product as an oil. Purification using Flash Column Chromatography on Silica Gel, eluting with a gradient of 5%-20% ethyl acetate in hexanes gave the title compound (10.8 g, (M+H)⁺=301) as an orange-yellow semi-solid.

Step 2. Preparation of (4-chloro-2-methylsulfanylpyrimidin-5-yl)-(2-chlorophenyl)-methanone.

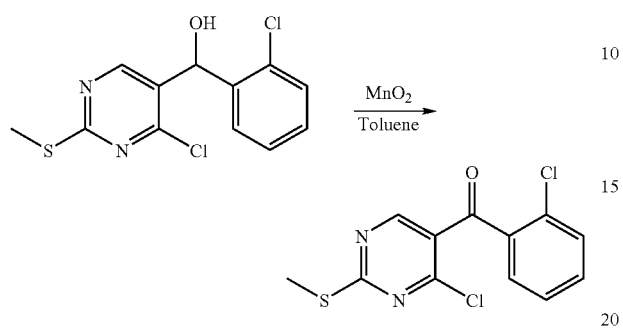

To a solution of (2-chlorophenyl)-(4-chloro-2-methylsulfanylpyrimidin-5-yl)methanol (10.8 g, 35.75 mol) in toluene (150 mL) was added manganese (IV) oxide (Aldrich) (31.2 g, 10 eq). The resulting mixture was heated to reflux with stirring for a total of 2.5 hours. The reaction was then filtered hot through a 3.5 cm pad of Celite. The pad of Celite was rinsed with hot ethyl acetate, and the filtrate was concentrated to give a crude oil. Purification by Flash Column Chromatography on Silica Gel eluting with a gradient of 2%-10% ethyl acetate in hexanes gave the title compound as a yellow viscous semi-solid (5.3 g, (M+H)⁺=299.

Step 3. Preparation of 3-(2-chlorophenyl)-6-methylsulfanyl-1H-pyrazolo[3,4-d]pyrimidine

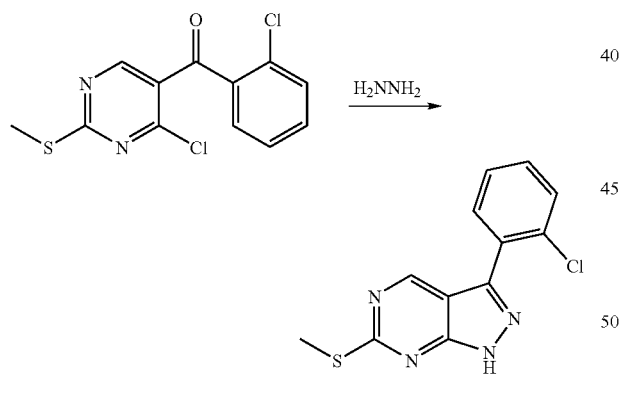

To a solution of (2-chlorophenyl)-(4-chloro-2-methylsulfanylpyrimidin-5-yl)-methanone (5.3 g, 17.72 mmol) in ethanol (25 mL) was added anhydrous hydrazine (1.12 ml, 2 eq) dropwise with stirring. The reaction was then stirred for 20 minutes, after which it was cooled in an ice bath and the precipitated solid was removed by filtration. The solid was rinsed with cold ethanol. The filtrate was concentrated to provide a crude oil, which was diluted with ethyl acetate (80 mL), tetrahydrofuran (10 mL), methanol (5 mL), and water (80 mL). This mixture was partitioned and the layers separated. The organic layer was collected and dried over magnesium sulfate, filtered and concentrated to give the title compound as a yellow powder (2.81 g, (M+H)⁺=277).

Step 4 Preparation of 3-(2-chloro-phenyl)-6-methanesulfonyl-1H-pyrazolo[3,4d]pyrimidine

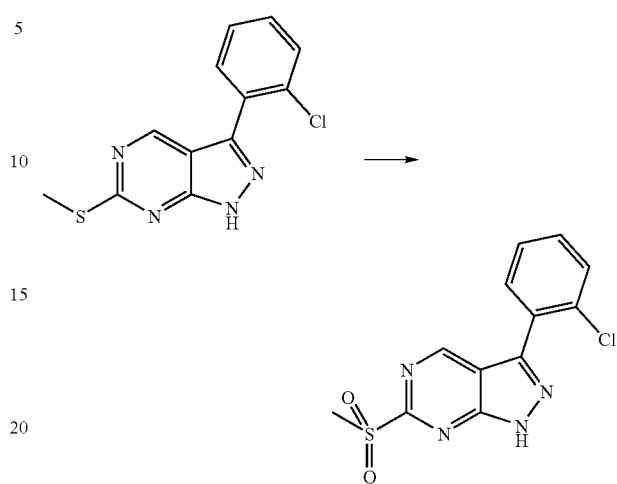

To a cooled (ice bath) solution of 3-(2-chlorophenyl)-6-methylsulfanyl-1H-pyrazolo[3,4-d]pyrimidine (2.8 g, 10.37 mmol) in THF (46 mL) and methanol (28 mL) was added a solution of Oxone (Aldrich) (10.9 g) in water (38 mL) dropwise. The mixture was stirred for 40 hours at room temperature. The reaction was monitored using a TLC analysis. The volume of the mixture was reduced about 80% via rotary evaporator after which ethyl acetate (80 mL), water (40 mL) and saturated sodium bicarbonate (15 mL) were added and the layers were partitioned and separated. The organic layer was further washed with brine (50 mL) and back extracted with ethyl acetate (80 mL). The ethyl acetate phase was dried over magnesium sulfate, filtered and concentrated to give the title compound as a red-brown powder (2.90 g, (M−H)⁻=307).

Step 5. Preparation of 3-(2-chlorophenyl)-6-(2,4-difluorophenoxy)-1H-pyrazolo[3,4-d]pyrimidine

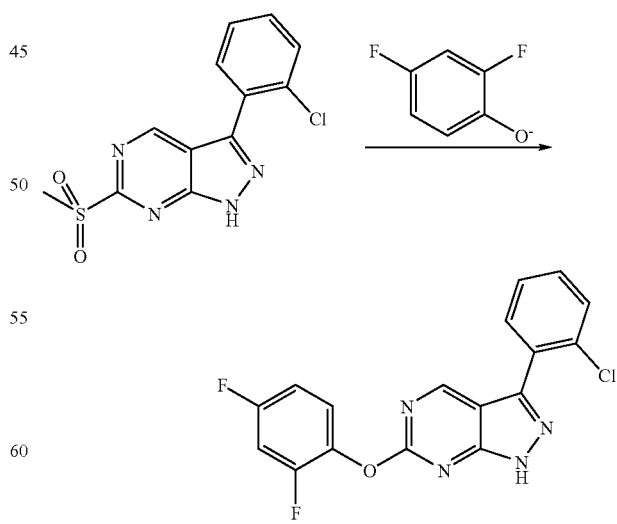

To a neat sample of 2,4-difluorophenol (Aldrich) (379 mg, 3 eq) in a Microwave Reactor Vessel, at 0° C. was added dropwise a 1.0 M potassium tert-butoxide solution in THF (2.9 mL, 3.05 eq). The mixture was stirred 5 minutes and then warmed to room temperature. Solid 3-(2-chlorophenyl)-6-methylsulfonyl-1H-pyrazolo[3,4-d]pyrimidine (300 mg, 0.971 mmol) was added and the reaction mixture was placed in a Microwave Reactor and heated at 120° C. for 15 minutes. The reaction mixture was diluted with ethyl acetate (50 mL), saturated aqueous ammonium chloride (10 mL) and water (40 mL). The mixture was partitioned and the organic layer was collected. The aqueous layer was extract with ethyl acetate (40 mL). The organic layers were combined, dried over magnesium sulfate, filtered and concentrated to provide the crude compound. Purification by Preparative Thin Layer Chromatography eluting with 1.8% methanol in dichloromethane, followed by crystallization from methylene chloride/hexanes gave the title compound as a white powder (553 mg, (M+H)$^+$= 359, M.P.=173.4-176.4° C.).

Additional compounds prepared by the procedure of Example 1 are shown in Table 1 above.

Example 2

This example illustrates a synthesis of [3-(2-chlorophenyl)-1H-pyrazolo[3,4-d]pyrimidin-6-yl]-(2-fluorophenyl) amine in the manner shown in Scheme I above.

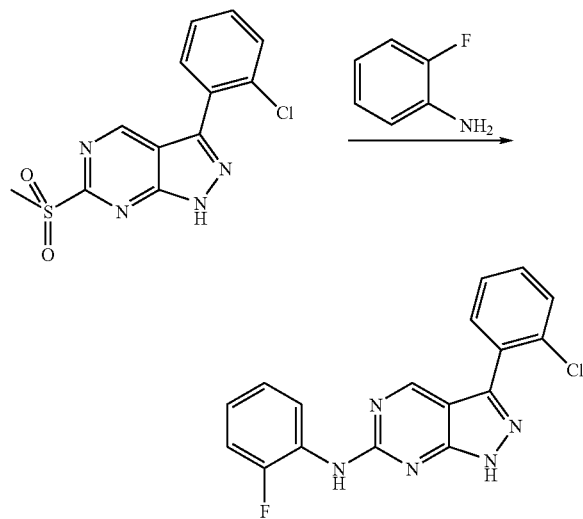

A mixture of 3-(2-chlorophenyl)-6-methylsulfonyl-1H-pyrazolo[3,4-d]pyrimidine (280 mg, 0.91 mmol, from step 4 of Example 1) and 2-fluoroaniline (Aldrich) (1.0 g, 10 eq) was heated at 140 ° C. in an oil bath under argon atmosphere. After two hours, the mixture was cooled to ambient temperature and purified by Preparative Thin Layer Chromatography eluting with 35% ethyl acetate in hexanes, followed by trituration from hot methylene chloride/hexanes gave the title compound as a white powder (35 mg, (M+H)$^+$=340, M.P.=230.2-232.4° C.).

Additional compounds prepared by this Example are shown in Table 1 above.

Example 3

This example illustrates a synthesis of 3-(2-chlorophenyl)-6-(2,4-difluorophenylsulfanyl)-1H-pyrazolo[3,4-d]pyrimidine.

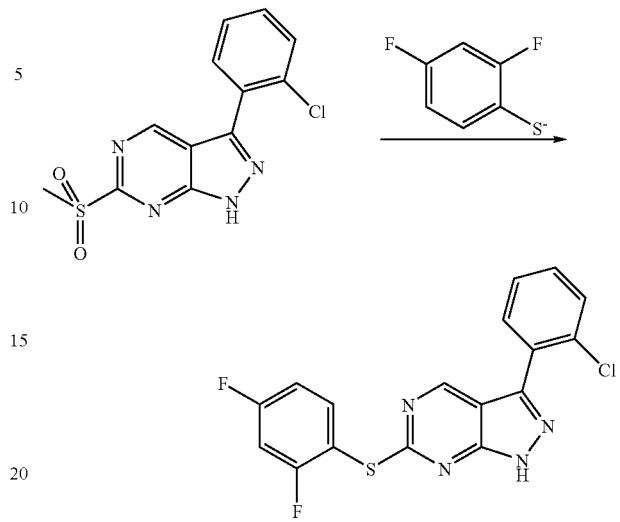

To a 0° C. solution of 2,4-difluorothiophenol (Aldrich) (116 μL, 0.972 mmol) was added potassium tert-butoxide (Aldrich) (1.0M solution in tetrahydrofuran, 988 μL, 0.988 mmol), and the resulting yellow suspension was diluted with 5 mL tetrahydrofuran and stirred for 5 minutes at 0° C. The cooling bath was removed and the suspension was stirred for another 15 minutes at room temperature, and 3-(2-chlorophenyl)-6-methanesulfonyl-1H-pyrazolo[3,4-d]pyrimidine (100 mg, 0.324 mmol) was then added as a powder. The resulting brown suspension was refluxed for 17 hours. The reaction mixture was cooled to ambient temperature and then concentrated. The yellow solid residue was diluted with 20 mL ethyl acetate and 20 mL of saturated aqueous ammonium chloride. The aqueous phase was extracted with ethyl acetate (2×20 mL). The combined organic phases were dried over magnesium sulfate, filtered, and concentrated to give the crude product as a yellow solid. Purification using preparative thin layer chromatography with 20% ethyl acetate in hexanes gave the title compound (64 mg, (M+H)$^+$=375, M.P.=177.6-183.2° C.).

Additional compounds prepared by this Example are shown in Table 1 above. Oxidation of the sulfur atom yielded correspoding sulfonyl and sulfinyl compounds.

Example 4

This example illustrates a synthesis of 3-(2-chlorophenyl)-6-(2,4-difluoro-phenoxy)-1H-pyrazolo[3,4-d]pyrimidine following the procedure of Scheme II.

Step 1. Preparation of 3-(2-chlorophenyl)-3-oxo-propionic acid, methyl ester.

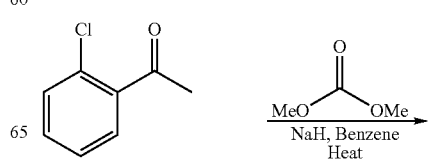

-continued

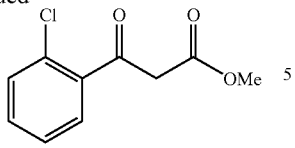

To a suspension of sodium hydride (30.8 g, 770 mmol, 60% in oil) in benzene (275 mL) and dimethyl carbonate (50 mL) was slowly added a solution of 2-chloro-acetophenone (Aldrich) (40 mL, 308 mmol) in dimethyl carbonate (28 mL) via an addition funnel. The reaction mixture was then slowly and cautiously heated to 60° C. [Note: reaction is exothermic: ice bath cooling may be necessary to control the reaction]. After stirring for 15 minutes, the reaction mixture was stirred at 111° C. for one hour. The mixture was next cooled to ambient temperature and methanol was added to destroy excess sodium hydride. The material was poured onto a cold solution of aqueous hydrochloric acid (10%, 308 mL) in ice (300 mL). The resulting mixture was diluted with ether (250 mL). The organic layer was separated and washed with water (350 mL). The aqueous layer was extracted with ether (250 mL). The ether layers were combined, dried (magnesium sulfate), filtered and concentrated to give a crude oil. Purification via distillation under vacuum provided the product as a pale, clear oil (53.6 g; B.P.=120-121° C., $(M+H)^+$=213).

Step 2. Preparation of 2-(2-chlorobenzoyl)-3-ethoxyacrylic acid, ethyl ester.

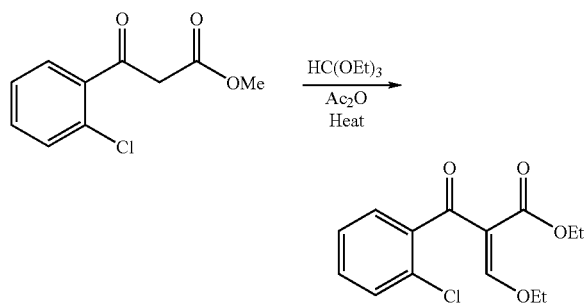

To a flask containing 3-(2-chlorophenyl)-3-oxo-propionic acid, methyl ester (20 g, 94 mmol) was added triethylorthoformate (37.5 mL, 225.6 mmol) and acetic anhydride (63 mL, 667 mmol). The resulting mixture was heated to 130° C. with stirring for a total of 2 hours, then stirred over night at room temperature. The reaction mixture was concentrated under reduced pressure to provide a crude oil, which was used directly in the next step.

Step 3. Preparation of (2-chloro-phenyl)-(4-hydroxy-2-methylsulfanylpyrimidin-5-yl)-methanone.

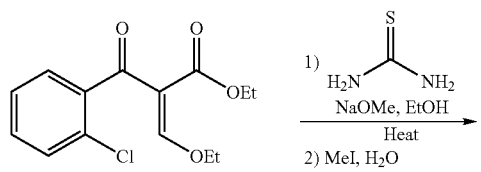

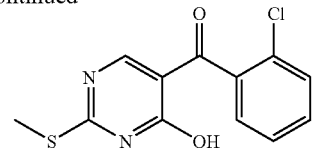

To a solution of 2-(2-chlorobenzoyl)-3-ethoxyacrylic acid, ethyl ester (23.9 g, 23.9 mmol) in absolute ethanol (80 mL) was added thiourea (7.14 g, 23.9 mmol), followed by a solution of 25% sodium methoxide in methanol (20.4 mL, 89.3 mmol). The reaction mixture was heated to reflux for four hours, and then stirred at room temperature over night. The resulting mixture was diluted with water (50 mL) and then treated with iodomethane (11.99 mL, 21.5 mmol). The material was warmed to 40° C. and stirred for three hours. Water (10 mL) was added and the material allowed to cool to room temperature over 10 minutes. Another 50 mL of water was added and the product slowly crystallized out of the resulting solution. The product was collected by filtration (18.72 g, $(M+H)^+$=281).

Step 4 Preparation of (4-chloro-2-methylsulfanylpyrimidin-5-yl)-(2-chlorophenyl)-methanone.

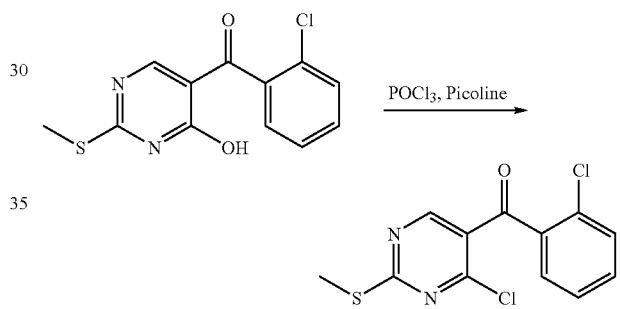

To a cooled (ice bath) mixture of (2-chlorophenyl)-(4-hydroxy-2-methylsulfanylpyrimidin-5-yl)methanone (18.72 g, 66 mmol) and picoline (3.95 mL, 39.6 mmol) was added dropwise phosphoryl chloride (37.3 mL, 396 mmol) via an addition funnel. The resulting mixture was removed from the ice bath and heated to 80° C. for 2 hours. The reaction was cooled to ambient temperature and poured onto ice (250 mL). Ethyl acetate was added and the layers were partitioned and separated. The organic layer was further washed with two consecutive solutions of saturated sodium bicarbonate (150 mL) followed by brine (150 mL). The aqueous layers were back extracted with ethyl acetate (2×150 mL). The combined ethyl acetate layers were dried over magnesium sulfate, filtered and concentrated to give the product as a yellow solid (17.36 g, $(M+H)^+$=299.

Step 5. Preparation of 3-(2-chlorophenyl)-6-(2,4-difluorophenoxy)-1H-pyrazolo[3,4-d]pyrimidine.

(4-Chloro-2-methylsulfanylpyrimidin-5-yl)-(2-chlorophenyl)methanone was converted to the desired pyrazolopyrimidine targets using the procedures similar to those described in Example 1, steps 3, 4 and 5 above.

Example 5

This example illustrates a synthesis of 3-(2-chlorophenyl)-6-(2,4-difluorophenoxy)-1H-pyrazolo[3,4-b]pyrazine following the procedure of Scheme III above.

Step 1. Preparation of (2-chlorophenyl)-(3,5-dichloropyrazin-2-yl)-methanol.

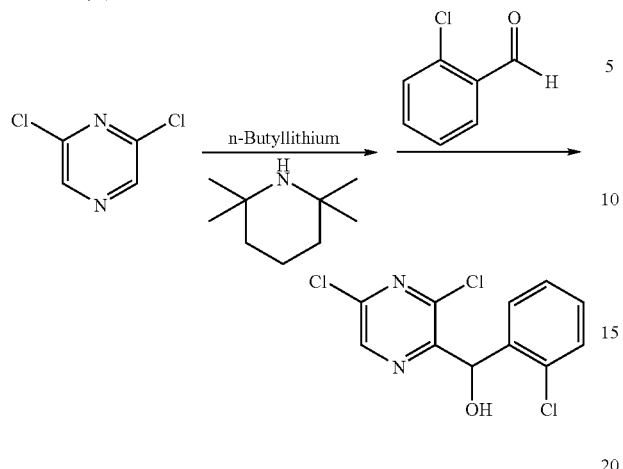

To a −20° C. solution of n-butyllithium (2.5 M in hexane, Aldrich, 26.5 mmol) in dry tetrahydrofuran (200 mL) under argon was added 2,2,6,6-tetramethylpiperidine (Aldrich, 11.5 mL, 66.5 mmol, 1.22 eq). The resulting solution was warmed to 0° C. over 0.5 hour period. The solution was then cooled to −78° C., and a solution of 2,6-dichloropyrazine (Aldrich, 8.24 g, 55.3 mmol, 1.0 eq) in tetrahydrofuran was slowly added via a syringe. After addition was complete, the resulting mixture was stirred at −78° C. for an additional 1 hour after which 2-chlorobenzaldehyde (Aldrich, 9.3 mL, 83 mmole, 1.5 eq) was added drop wise via a syringe. The reaction mixture was stirred for an additional 1 hour, quenched with hydrochloric acid (18 mL, 220 mmol, 4 eq)/ethanol (75 mL)/tetrahydrofuran (90 mL) mixture, and then warmed to room temperature. The reaction mixture was diluted with aqueous saturated sodium bicarbonate solution and extracted with ether. The organic layer was separated and washed with brine, dried over sodium sulfate, filtered, and concentrated to give a crude oil which was purified via chromatography using dichloromethane/hexanes (1:1) as the eluent to give (2-chlorophenyl)-(3,5-dichloropyrazin-2-yl)methanol (12.8 g, 44 mmol, 80% yield). Mass spec, M+1=290.

Step 2. Preparation of (2-chlorophenyl)-(3,5-dichloropyrazin-2-yl)methanone.

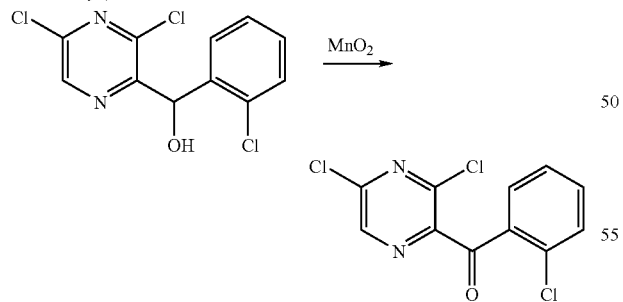

To a dichloromethane solution of (2-chlorophenyl)-(3,5-dichloropyrazin-2-yl)methanol (7.1 g, 24.5 mmol) was added portion wise solid manganese (IV) oxide (25 g, 245 mmol) and the resulting mixture was stirred at room temperature overnight. The reaction mixture was filtered and the filtrate was concentrated to give (2-chlorophenyl)-(3,5-dichloropyrazin-2-yl)methanone (6.02 g, 21 mmol, 85% yield). Mass spec., M+1=288.

Step 3. Preparation of [3-chloro-5-(2,4-difluorophenoxyl)pyrazin-2-yl]-(2-chlorophenyl)-methanone.

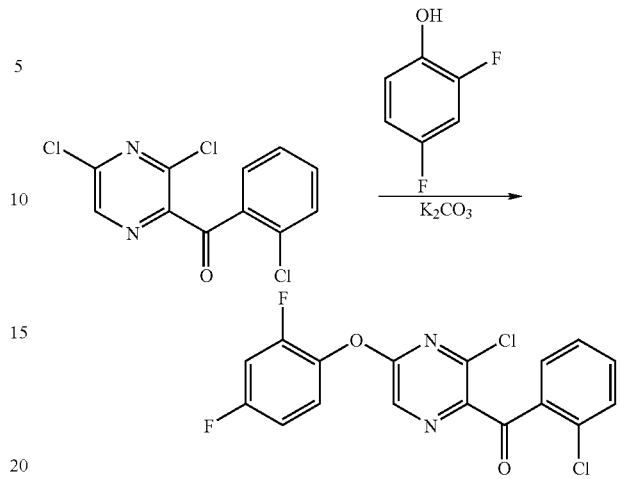

To a dimethylformamide, i.e., DMF, (25 mL) solution of (2-chlorophenyl)-(3,5-dichloropyrazin-2-yl)methanone (2.1 g, 7.3 mmol, 1.0 eq) under nitrogen was added 2,4-difluorophenol (0.7 mL, 7.3 mmol, 1.0 eq) and potassium carbonate (1.21 g, 8.76 mmol, 1.2 eq). The resulting mixture was stirred overnight at room temperature and then concentrated. The residue was dissolved in dichloromethane and washed with water and brine. The organic layer was dried over sodium sulfate, filtered and concentrated to give a crude oil which was purified via a chromatography using dichloromethane/hexanes (1:1) as the eluent to give [3-chloro-5-(2,4-difluorophenoxyl)pyrazin-2-yl]-(2-chlorophenyl)methanone (2.46 g, 6.45 mmol, 88% yield). Mass spec., M+1=382.

Step 4. Preparation of 3-(2-chlorophenyl)-6-(2,4-difluorophenoxy)-1H-pyrazolo[3,4-b]pyrazine.

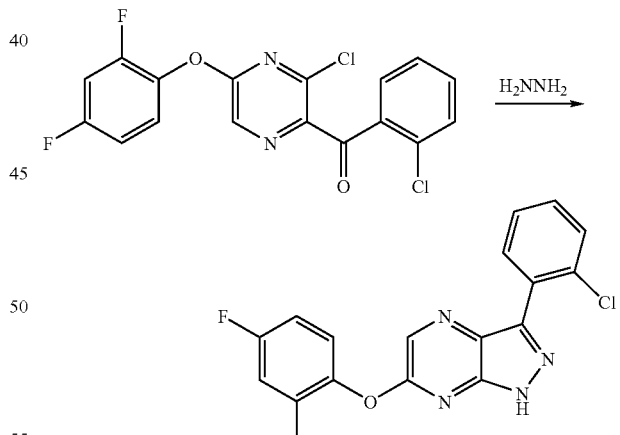

To a solution of [3-chloro-5-(2,4-difluorophenoxyl)pyrazin-2-yl]-(2-chlorophenyl)methanone (0.73 g, 1.9 mmol, 1.0 eq) in ethanol was added hydrazine hydrate (0.19 mL, 3.8 mmol, 2.0 eq). The resulting mixture was refluxed under nitrogen for 0.5 hours. The reaction mixture was cooled and filtered to give 3-(2-chlorophenyl)-6-(2,4-difluorophenoxy)-1H-pyrazolo[3,4-b]pyrazine (0.285 g, 0.8 mmol, 42% yield) as a solid. MP=240.5-241.5° C. Mass spec., M+1=359.

Additional compounds prepared by this Example are shown in Table 1 above.

Example 6

This example illustrates a synthesis of 3-(2-chlorophenyl)-6-(2,4-difluoro-phenoxy)-1H-pyrazolo[4,3-c]pyridine following the procedure of Scheme IV.

Step 1. Preparation of 2-chloro-5-methylpyridine-1-oxide.

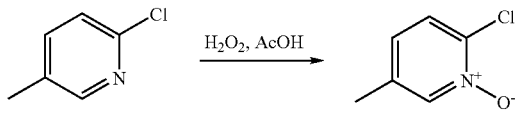

To a solution of 2-chloro-5-methylpyridine (10 mL) in 155 mL of glacial acetic acid was added 19 mL of 30% aqueous hydrogen peroxide. The mixture was stirred at 80° C. for 8 hours. The mixture was diluted with 100 mL of water and then concentrated in a vacuum. The residue was made strongly alkaline with anhydrous sodium carbonate and shaken with 200 mL of chloroform. The solids were removed via filtration, and the filtrate was dried over sodium sulfate, filtered and concentrated to give 10.8 g of the 2-chloro-5-methylpyridine-N-oxide (82%). Mass Spec. M+H=144.

Step 2. Preparation of 2-chloro-5-methyl-4-nitropyridine-1-oxide.

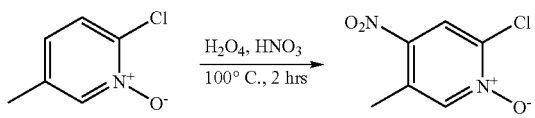

To a mixture of 165 mL of nitric acid and 209 mL of sulfuric acid was slowly added 56.4 g of 2-chloro-5-methylpyridine-1-oxide. The reaction mixture was stirred at 100° C. for two hours, cooled to room temperature, and added to ice. Sodium carbonate was added to adjust the pH to about pH 2 to pH 3. The resulting yellow solid was separated by filtration and washed with ice-water. The combined filtrates were extracted with hot chloroform. The extracts were combined, dried over sodium sulfate, and concentrated to give 59.1 g of 2-chloro-5-methyl-4-nitropyridine-1-oxide (80%). Mass Spec. M+H=189.

Step 3. Preparation of 2-(2,4-difluorophenoxy)-5-methyl-4-nitropyridine-1-oxide.

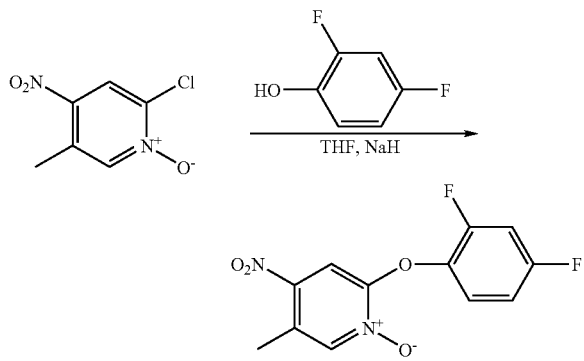

To a suspension of sodium hydride (0.47 g, 60% in oil) in 50 mL of THF was added dropwise a solution of 1 mL of 2,4-difluorophenol in 10 mL of THF. The reaction mixture was stirred for one hour, and 2-chloro-5-methyl-4-nitropyridine-1-oxide (2.0 g) was added slowly. The resulting mixture was stirred at reflux for 8 hours and at room temperature overnight. The solvent was removed and the light yellow solid isolated by extraction with methylene chloride. Purification via chromatography (silica gel, ethyl acetate/hexane, 1:1) gave 1.65 g of 2-(2,4-difluorophenoxy)-5-methyl-4-nitropyridine-1-oxide (55% yield). Mass Spec. M+H=283.

Step 4. Preparation of 2-(2,4-difluoro-phenoxy)-5-methyl-1-oxy-pyridin-4-ylamine.

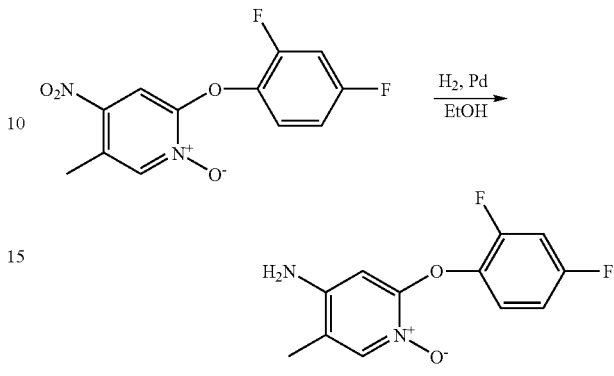

To a solution of 2-(2,4-difluorophenoxy)-5-methyl-4-nitropyridine-1-oxide (12.0 g) in 250 mL of anhydrous ethanol was added 2.0 g of 10% Pd on carbon catalyst. The hydrogenation was performed on a Parr hydrogenator at 40 psi for 30 minutes. The solution was filtered through a pad of Celite, dried and concentrated to give 10.1 g of 2-(2,4-difluorophenoxy)-5-methyl-1-oxy-pyridin-4-ylamine (94% yield). Mass Spec. M+H=254.

Step 5. Preparation of 2-(2,4-difluorophenoxy)-5-methylpyridin-4ylamine.

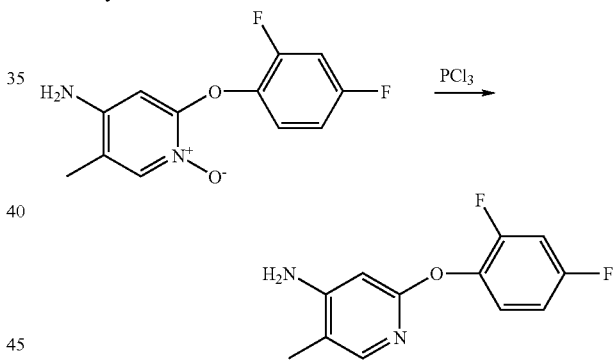

To a solution of 2-(2,4-difluoro-phenoxy)-5-methyl-1-oxy-pyridin-4-ylamine (4.0 g) in 75 mL of anhydrous chloroform, a solution of phosphorus trichloride (4.1 mL) in 20 mL of chloroform was added dropwise at 0-5° C. with stirring. The mixture was stirred for 12 hours at room temperature and then heated to reflux for three hours, cooled, poured into water, basified (NaOH), extracted (CHCl₃), dried over Na₂SO₄ to give 3.5 g of 2-(2,4-difluorophenoxy)-5-methylpyridin-4ylamine (94% yield). Mass Spec. M+H=238.

Step 6 Preparation of N-[2-(2,4-difluorophenoxy)-5-methylpyridin-4-yl]acetamide.

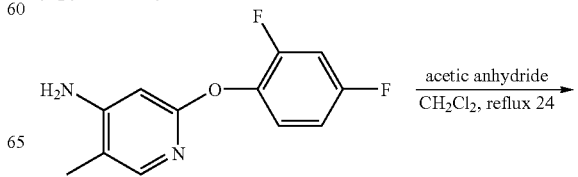

-continued

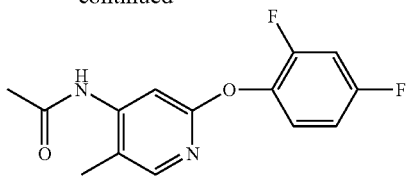

To a solution of 2-(2,4-difluorophenoxy)-5-methylpyridin-4ylamine (3.6 g) in 80 mL of methylene chloride was added 4.7 g of acetic anhydride. The mixture was heated for 24 hours on a steam bath and then poured onto 200 mL of 5% aqueous sodium carbonate. The aqueous solution was extracted with methylene chloride. The organic layers were combined, dried and concentrated to give 4.2 g of N-[2-(2,4-difluorophenoxy)-5-methylpyridin-4-yl]acetamide (99% yield). Mass. Spec. M+H=279.

Step 7. Preparation of 1-[6-(2,4-difluorophenoxy)pyrazolo[4,3-c]pyridine-1-yl]ethanone.

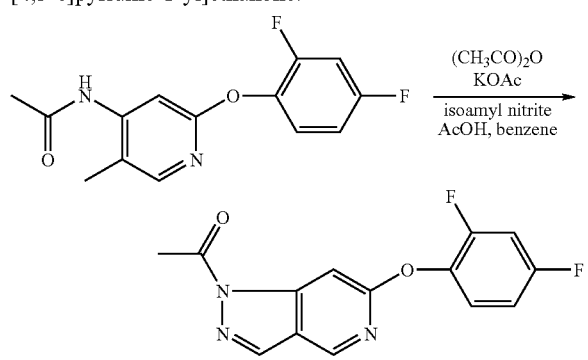

A mixture of N-[2-(2,4-difluorophenoxy)-5-methylpyridin-4-yl]acetamide (2.3 g), acetic anhydride (2.6 g), acetic acid (2.7 mL) and potassium acetate (1.7 g) in 40 mL of benzene was brought to reflux. A solution of isoamyl nitrite (1.5 mL) in 10 mL of benzene was added to the refluxing solution over a period of two hours and refluxing was continued for an additional 18 hours. The reaction mixture was cooled and stirred with 50 mL of a 5% aqueous sodium carbonate solution for 3 hours. The organic layer was separated, dried, concentrated and purified via chromatography (silica gel, 8% ethyl acetate/hexane) to give 0.27 g of 1-[6-(2,4-difluorophenoxy)pyrazolo[4,3-c]pyridine-1-yl]ethanone (11% yield). Mass Spec. M+H=290.

Step 8. Preparation of 6-(2,4-difluorophenoxy)-1H-pyrazolo[4,3-c]pyridine.

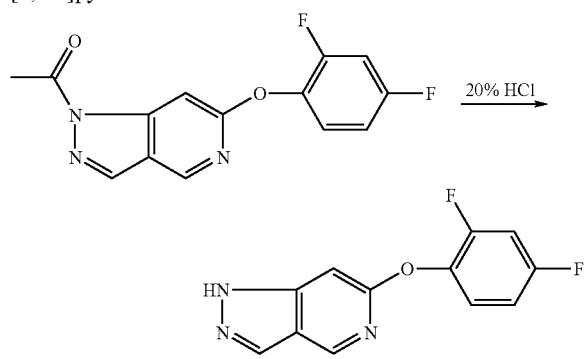

A mixture of 1-[6-(2,4-difluorophenoxy)pyrazolo[4,3-c]pyridine-1-yl]ethanone (0.26 g) in 15 mL of 20% aqueous hydrochloric acid was heated for 3 hours on a steam bath, cooled, neutralized with NaHCO$_3$, and extracted with CH$_2$Cl$_2$ to give 0.21 g of 6-(2,4-difluorophenoxy)-1H-pyrazolo[4,3-c]pyridine (95% yield). Mass Spec. M+H=248.

Step 9. Preparation of 6-(2,4-difluorophenoxy)-3-iodo-1H-pyrazolo[4,3-c]pyridine.

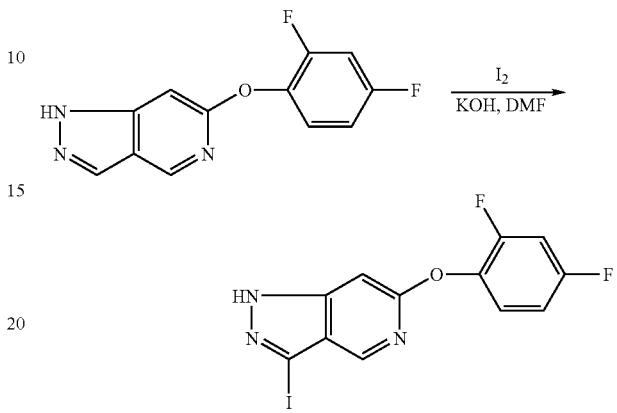

To a room temperature solution of 6-(2,4-difluorophenoxy)-1H-pyrazolo[4,3-c]pyridine (0.10 g) in DMF was added 0.11 g of iodine and 0.049 g of potassium hydroxide. After 5 hours, additional 10% of iodine was added and a reaction mixture was stirred for an additional one hour. The mixture was quenched with 1 M sodium bisulfite (50 mL) solution and extracted with ethyl acetate (3×30 mL). The organic layers were combined, dried over MgSO$_4$, and concentrated to give 0.11 g of 6-(2,4-difluorophenoxy)-3-iodo-1H-pyrazolo[4,3-c]pyridine (71% yield). Mass Spec. M+H=374.

Step 10. Formation of N-t-Boc Derivative.

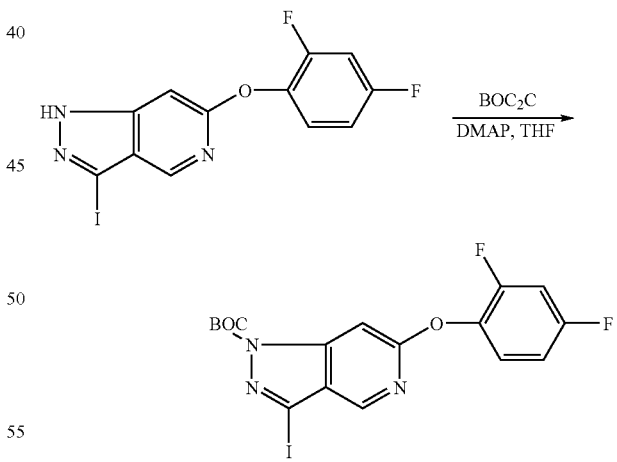

To a solution of 6-(2,4-difluorophenoxy)-3-iodo-1H-pyrazolo[4,3-c]pyridine (0.10 g) in THF was added 0.15 g of di-tert-butyl dicarbonate and 1.6 mg of 4-(dimethylamino)pyridine. The resulting solution was refluxed for one hour under a nitrogen atmosphere, cooled, concentrated, and the residue was purified by chromatography on silica gel. Elution with ethyl acetate/hexane (1/9) afforded 0.11 g of the N-BOC derivative of 6-(2,4-difluorophenoxy)-3-iodo-1H-pyrazolo[4,3-c]pyridine (86% yield). Mass Spec. M+H=474.

Step 11. Preparation of 3-(2-chlorophenyl)-6-(2,4-difluorophenoxy)-pyrazolo[4,3-c]pyridine-1-carboxylic acid, tert-butyl ester.

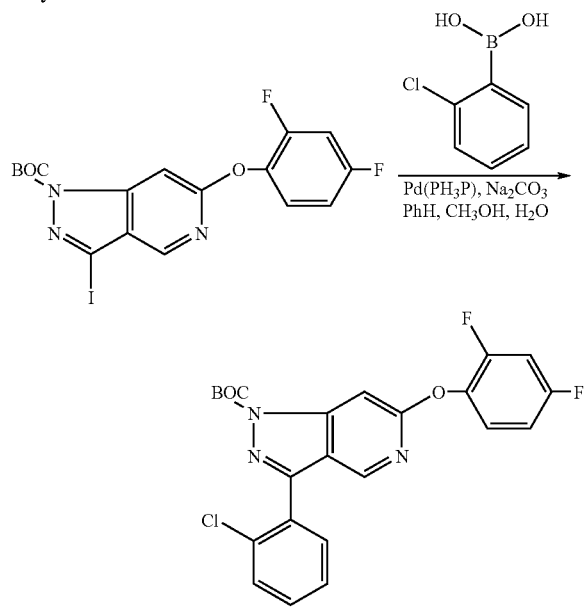

A solution of 1-BOC-6-(2,4-difluorophenoxy)-3-iodo-1H-pyrazolo[4,3-c]pyridine (0.071 g) and 2-chlorophenylboronic acid in 5 mL of benzene and 1 mL of methanol was stirred at room temperature for 15 minutes. To this solution was added tetrakis(triphenylphosphine)palladium catalyst (52 mg) and 0.3 mL of 1 M sodium carbonate. The resulting mixture was heated to reflux for five hours, cooled, filtered and the organic layer was separated. The organic layer was washed, dried and concentrated. The residue was purified via chromatography using 5% ethyl acetate in hexane as the eluent to afford 45 mg of 3-(2-chlorophenyl)-6-(2,4-difluorophenoxy)-pyrazolo[4,3-c]pyridine-1-carboxylic acid, tert-butyl ester (66% yield). Mass. Spec. M+H=458.

Step 12. Preparation of 3-(2-chlorophenyl)-6-(2,4-difluorophenoxy)-1H-pyrazolo[4,3-c]pyridine.

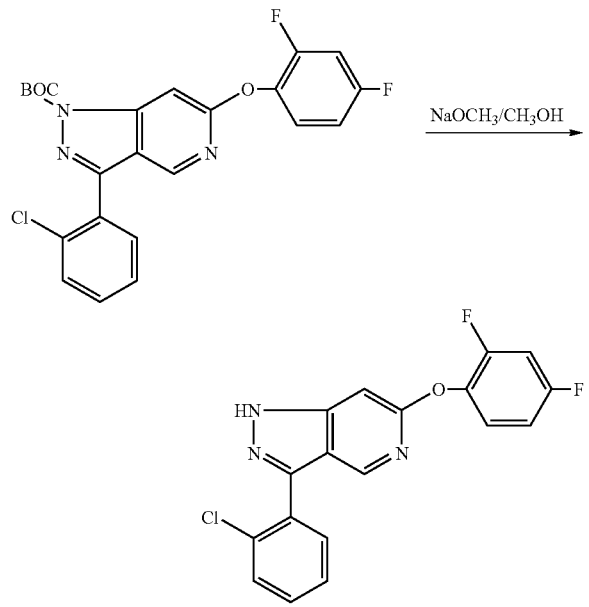

A mixture of 3-(2-chlorophenyl)-6-(2,4-difluorophenoxy)-pyrazolo[4,3-c]pyridine-1-carboxylic acid, tert-butyl ester (14.0 mg) in 3 mL of 0.5 M sodium methoxide solution in methanol was stirred for 30 minutes at room temperature. The resulting solution was concentrated and the residue was extracted with ethyl acetate, washed, dried and concentrated to give 10.0 mg of 3-(2-chlorophenyl)-6-(2,4-difluorophenoxy)-1H-pyrazolo[4,3-c]pyridine (91% yield). Mass Spec. M+H=356.

Example 7

This example illustrates a synthesis of 3-(2-Chloro-phenyl)-6-(2,4-difluoro-phenoxy)-1H-pyrazolo[3,4-b]pyridine.

Step 1. Preparation of (2-Chloro-phenyl)-(2,6-dichloro-pyridin-3-yl)-methanol

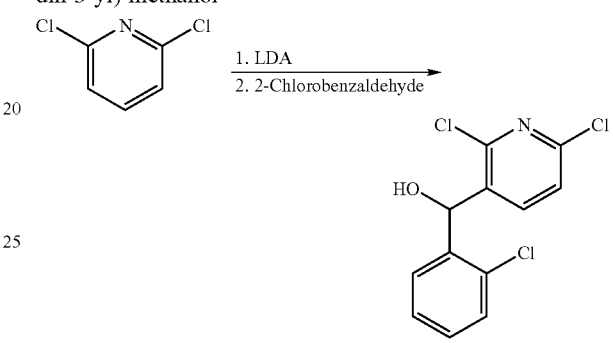

2,6-dichloropyridine (10.0 g, 67.6 mmol) was dissolved in 220 mL of dry THF and the reaction mixture was cooled to −78° C. under argon. Lithium diisopropylamine (60 mL, 118 mmol, 2M in heptanes) was added to the reaction mixture over 12 minutes via cannula, and the reaction mixture was stirred for 15 minutes at −78° C. 2-Chlorobenzaldehyde (16 mL, 141.96 mmol) was added dropwise, and the reaction mixture was stirred for 30 minutes at −78° C. The reaction was quenched by addition of 80 mL saturated ammonium chloride and 200 mL of water, and the aqueous mixture was extracted once with 300 mL of EtOAc and a second time with 250 mL of EtOAc. The comnbined organic phase was washed with saturated brine and water and was dried over MgSO₄. Solvent was removed under reduced pressure and the residue was purified by FLASH column chromatography using 5%-20% EtOAc/Hexanes to yield 12.2 g of (2-chloro-phenyl)-(2,6-dichloro-pyridin-3-yl)-methanol as a yellow oil. Mass Spec. M+H=290.

Step 2. Preparation of (2-Chloro-phenyl)-(2,6-dichloro-pyridin-3-yl)-methanone

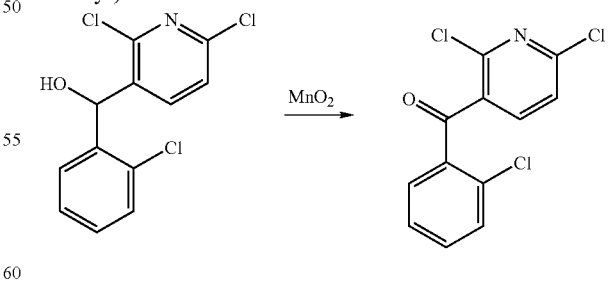

(2-Chloro-phenyl)-(2,6-dichloro-pyridin-3-yl)-methanol (12.2 g, 42.3 mmol) was dissolved in 200 mL of dry toluene, and 87 g of manganese dioxide was added. The reaction mixture was refluxed for 2.5 hours, and was then hot filtered through Celite. The Celite plug was washed with 80 mL of hot EtOAc (in several portions), and the organic solvents were combined. Removal of solvent under reduced pressure yielded 14.05 g of (2-chloro-phenyl)-(2,6-dichloro-pyridin-3-yl)-methanone as a viscous yellow oil. Mass Spec. M+H=288.

Step 3. Preparation of 6-Chloro-3-(2-chloro-phenyl)-1H-pyrazolo[3,4-b]pyridine

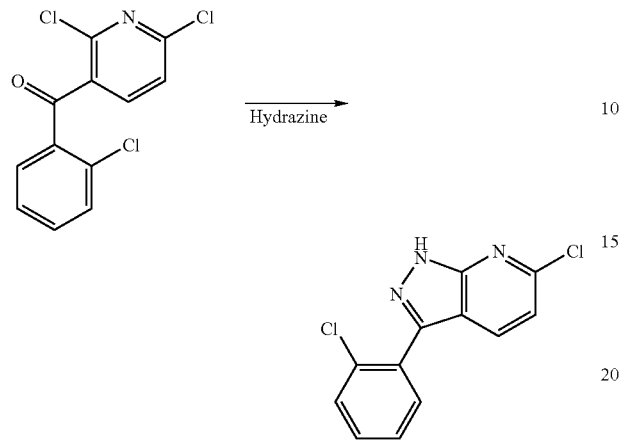

(2-Chloro-phenyl)-(2,6-dichloro-pyridin-3-yl)-methanone (3.0 g, 10.47 mmol) was dissolved in 25 mL of ethanol/THF (4:1) and cooled in an ice bath. Hunig's base (N,N-diisopropylethylamine, 1.8 mL, 10.47 mmol) was added to the reaction mixture, followed by dropwise addition of 0.36 mL (11.52 mmol) of hydrazine. The reaction mixture was stirred at 0° C. for five minutes, then heated to 70° C. for 1.5 hours. Volatiles were removed under reduced pressure, and the residue was taken up in 150 mL of EtOAc, 10 mL of THF and 10 mL of MeOH. To this mixture was added 20 mL of saturated ammonium chloride and 110 mL of water. The organic phase was collected, and the aqueous phase was wahsed with an additional 100 mL of EtOAc. The combined organic layers wer washed with brine, dried (MgSO$_4$), and solvent was removed to to yield 1.18 g of 6-chloro-3-(2-chloro-phenyl)-1H-pyrazolo[3,4-b]pyridine as a yellow solid. Mass Spec. M-H=262.

Step 4. Preparation of 3-(2-Chloro-phenyl)-6-(2,4-difluoro-phenoxy)-1H-pyrazolo[3,4-b]pyridine.

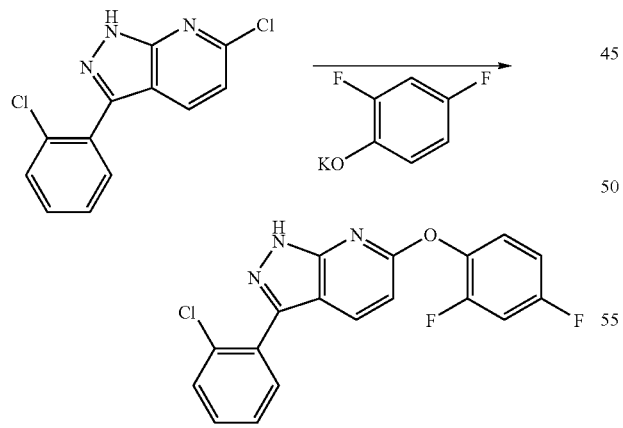

2,4-Difluorophenol (517 mg, 4 mmol) was placed in a 10 mL microwave reactor tube under nitrogen and cooled in an ice bath. Potassium t-butoxide (4 mL of 1.0 M solution in THF) was added dropwise, and the solution was stirred for five minutes at 0° C. The reaction mixture was warmed to room temperature, and 6-chloro-3-(2-chloro-phenyl)-1H-pyrazolo[3,4-b]pyridine (350 mg, 1.33 mmol) was added in one portion. The reaction was then heated to 160° C. via microwave for nine hours. The reaction mixture was cooled and partitioned between water and ethyl acetate. The organic phase was washed with brine, followed by water, and then dried over MgSO$_4$. The solvent was removed under reduced pressure, and the residue was eluted through a FLASH column using 0.5% MeOH in methylene chloride. Solvent was removed, and the residue was recrystallized from methylene chloride/hexanes to afford 78 mg of 3-(2-Chloro-phenyl)-6-(2,4-difluoro-phenoxy)-1H-pyrazolo[3,4-b]pyridine as a white solid. Mass Spec. M+H=358.

Additional compounds prepared by the above example are shown in Table 1 above.

Example 8

This example illustrates a synthesis of 6-(2,4-Difluoro-phenoxy)-3-(2-methoxy-phenyl)-1H-pyrazolo[4,3-b]pyridine.

Step 1. Preparation of (3,5-Difluoro-pyridin-2-yl)-(2-methoxy-phenyl)-methanone

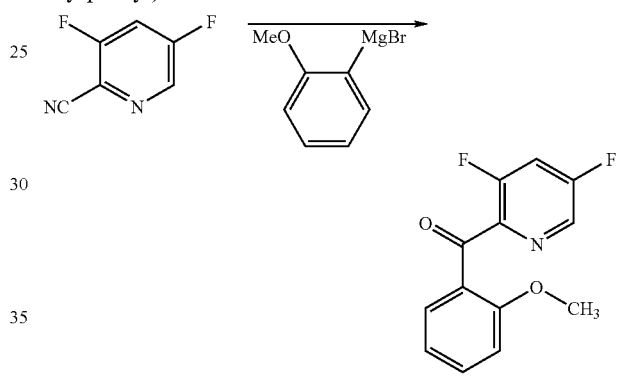

2-Methoxyphenyl magnesium bromide (53.3 mL of 1.75 M solution in THF was cooled to 0° C. 3,5-Difluoronicotinonitrile (5.0 g, 35.6 mmol) was added over 20 minutes to the reaction mixture at 0° C. The reaction was quenched by addition of of 60 mL of 2M H$_2$SO$_4$, and the mixture was allowed to warm to room temperature. The reaction mixture was extracted with 40 mL 50 mL EtOAc, and the aqueous phase was basified by addition 12 mL of 5M NaOH. Tee aqueous phase was then extracted twice with 70 mL of EtOAc, and the combined organic layers were washed with water, and dried (MgSO$_4$). The MgSO$_4$ was removed by filtration and solvent was removed under reduced pressure. The residue was purified by flash chromatography (40 mm×15 cm) with hexanes/EtOAc (0:1 to 4:1) to yield 7.9 g of (3,5-difluoro-pyridin-2-yl)-(2-methoxy-phenyl)-methanone. Mass Spec. M+H=250.

Step 1. Preparation of [5-(2,4-Difluoro-phenoxy)-3-fluoro-pyridin-2-yl]-(2-methoxy-phenyl)-methanone

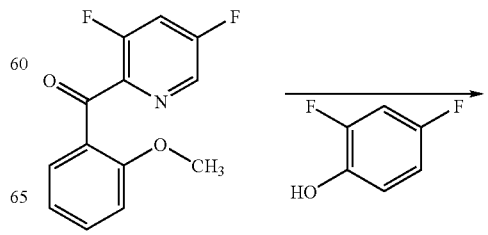

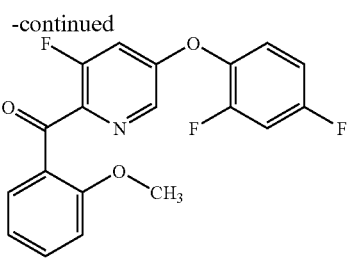

Powdered cesium carbonate (1.8 g, 5.7 mmol) was suspended in 8 mL of DMF, and 2,4-difluorophenol (0.45 mL, 4.8 mmol) was added to the reaction mixture. (3,5-Difluoro-pyridin-2-yl)-(2-methoxy-phenyl)-methanone (1.2 g, 4.8 mmol) dissoved in 7 mL of DMF was then added, and the reaction mixture was stirred for two hours at room temperature, and was then diluted with 60 mL of EtOAc, washed twice with 30 mL of water and once with 30 mL of saturated brine. The organic layer was dried over MgSO$_4$, filtered, and evaporated under reduced pressure. The resulting residue was purified by flash chromatography (40 mm×7.5 cm) with 20:1 to 4:1 hexanes/EtOAc to yield 0.37 g of [5-(2,4-fifluoro-phenoxy)-3-fluoro-pyridin-2-yl]-(2-methoxy-phenyl)-methanone as an oil. Mass Spec. M+H=360.

Step 4. Preparation of 6-(2,4-Difluoro-phenoxy)-3-(2-methoxy-phenyl)-1H-pyrazolo[4,3-b]pyridine.

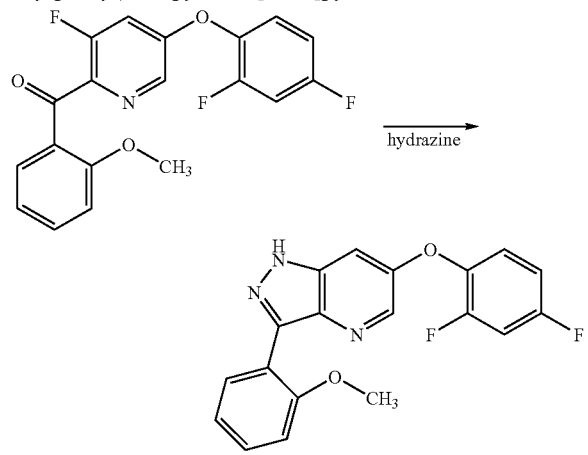

[5-(2,4-Difluoro-phenoxy)-3-fluoro-pyridin-2-yl]-(2-methoxy-phenyl)-methanone (560 mg, 1.5 mmol) was added to 17 mL of EtOH and the reaction mixture was heated until all solid had dissolved. The reaction mixture was cooled, and (N,N-diisopropyl)ethylamine (0.21 mL, 2.3 mmol) and hydrazine (0.1 mL, 3.1 mmol) were added. The reaction mixture was stirred for four hours at room temperature, and then was taken up in 60 mL of EtOAc, washed four times with 20 mL of water, dried (MgSO$_4$). The organic solvent was filtered and concentrated under reduced pressure. The residue was purified by flash chromatography 40 mm×7.5 cm) with 4: to 1:1 hexanes/EtOAc to yield 0.03 g of 6-(2,4-difluoro-phenoxy)-3-(2-methoxy-phenyl)-1H-pyrazolo[4,3-b]pyridine. Mass Spec. M+H=354.

Mp: 143.2-144.9° C.

Additional compounds prepared by the above example are shown in Table 1 above.

Example 9

This example illustrates a synthesis of 6-(2,4-Difluoro-phenoxy)-3-(2-methoxy-phenyl)-1H-pyrazolo[4,3-c]pyridazine.

Step 1. Preparation of (4,6-Dichloro-pyridazin-3-yl)-(2-methoxy-phenyl)-methanone

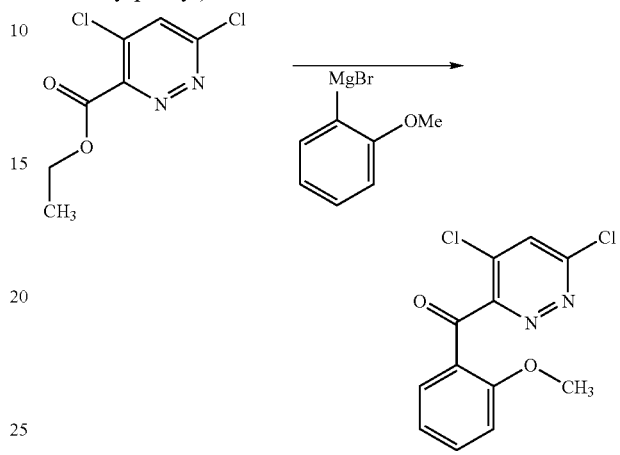

4,6-Dichloro-pyridazine-3-carboxylic acid ethyl ester (1.032 g, 4.67 mmol, prepared as described by Xie et al., WO 2004031174) was dissolved in 25 ml dry THF, and the reaction mixture was cooled in a dry ice/acetone bath for 15 minutes. 2-Methoxyphenyl magnesium bromide (7 mL of 1M solution in THF, 7.00 mmol) was added, and the reaction mixture was stirred for 8 hours under nitrogen at −78° C. Silica gel (11.0 g) was added, and the reaction mixture was allowed to warm to room temperature. Solvent was removed under reduced pressure, and the residue was purified by flash chromatography (0% to 20% EtOAc/Hexanes) to yield 1.029 g (3.65 mmol, 78%) of (4,6-dichloro-pyridazin-3-yl)-(2-methoxy-phenyl)-methanone as a yellow solid. Mass Spec. M+H=283.

Step 2. Preparation of (6-Chloro-4-methylsulfanyl-pyridazin-3-yl)-(2-methoxy-phenyl)-methanone

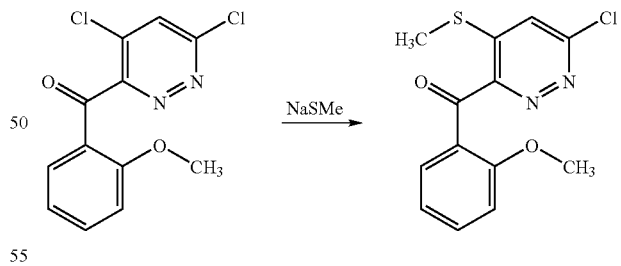

(4,6-Dichloro-pyridazin-3-yl)-(2-methoxy-phenyl)-methanone (0.75 g, 2.66 mmol), 25 mL dry THF, and NaSCH$_3$ (0.207 g, 2.81 mmol) were stirred under nitrogen at room temperature for 17 hours at room temperature. Diethyl ether (25 mL) was then added, and the reaction mixture was filtered through Celite. The filtrate was concentrated under reduced pressure, and the residue was purified via flash chromatography (0% to 33% EtOAc/Hexanes) to give 0.510 g (65%) of (6-Chloro-4-methylsulfanyl-pyridazin-3-yl)-(2-methoxy-phenyl)-methanone as a yellow solid. Mass Spec M+H=296.

Step 3. Preparation of [6-(2,4-Difluoro-phenoxy)-4-methyl-sulfanyl-pyridazin-3-yl]-(2-methoxy-phenyl)-methanone

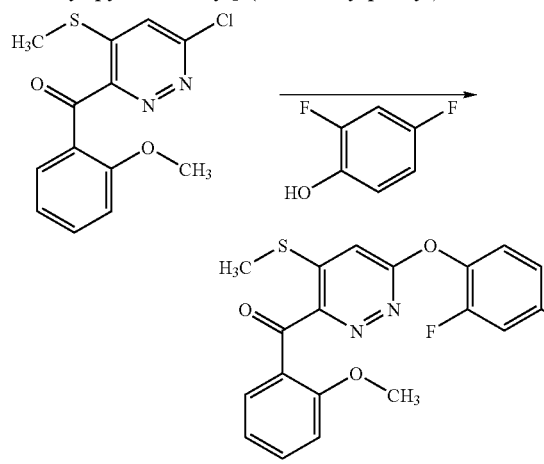

(6-Chloro-4-methylsulfanyl-pyridazin-3-yl)-(2-methoxy-phenyl)-methanone (0.101 g, 0.342 mmol, DMF (2 mL), 2,4-dinitrophenol (0.040 mL, 0.42 mmol) and sodium hydride ((0.017 g, 0.42 mmol of mineral oil suspension) were stirred under nitrogen for three hours at room temperature. The reaction mixture was then stirred for two hours at 68° C. The reaction mixture was cooled and 20 mL of diethyl ether was added. The organic mixture was washed twice with 20 mL water, once with 20 mL of saturated brine, and the organic layer was dried over MgSO$_4$. The MgSO$_4$ was removed by filtration, and the filtrate was concentrated under reduced pressure. The residue was purified by flash chromatography (0% to 33% EtOAc/Hexanes) to yield 0.107 g (81%) of [6-(2,4-difluoro-phenoxy)4-methylsulfanyl-pyridazin-3-yl]-(2-methoxy-phenyl)-methanone as a white solid. M+H=389.

Step 4. Preparation of 6-(2,4-Difluoro-phenoxy)-3-(2-methoxy-phenyl)-1H-pyrazolo[4,3-c]pyridazine.

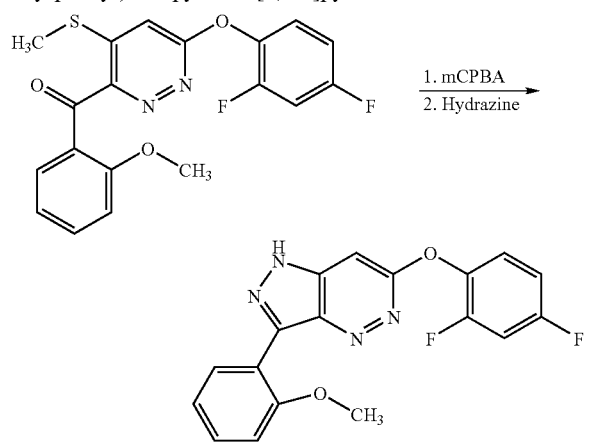

[6-(2,4-Difluoro-phenoxy)-4-methylsulfanyl-pyridazin-3-yl]-(2-methoxy-phenyl)-methanone (0.076 g, 0.196 mmol), dichloromethane (2 mL), and meta-chloro perbenzoic acid (0.055 g of 77% mCPBA, 0.25 mmol) were stirred together at room temperature for one hour. The reaction mixture was diluted with 5 mL of dichloromethane and washed three times with 5 mL of saturated aqueous sodium bicarbonate solution. The organic phase was dried over MgSO$_4$, filtered, and the filtrate was concentrated under reduced pressure. The resulting residue was dissolved in a mixture of 2 mL THF and 2 mL methanol, and hydrazine (0.0075 mL, 0.24 mmol) and diisopropylethylamine (0.045 mmol, 0.26 mmol) were added. The reaction mixture was stirred for 18 hours at room temperature, then partitioned between 10 mL EtOAc and 10 mL water. The organic layer was washed with 10 mL of saturated aqueous NaCl solution and dried over MgSO$_4$. The solution was filtered and the filtrate was concentrated under reduced pressure. The residue was purified by flash chromatography (0% to 33% EtOAc/Hexanes) to yield 0.030 g of a mixture of 6-(2,4-difluoro-phenoxy)-3-(2-methoxy-phenyl)-1H-pyrazolo[4,3-c]pyridazine and [6-(2,4-difluoro-phenoxy)$_4$-methylsulfonyl-pyridazin-3-yl]-(2-methoxy-phenyl)-methanone. This mixture was again treated with excess hydrazine for 18 hours together with heating to 65° C. to drive the reaction to completion, followed by workup and chromatography as described above, to yield 6 mg of 6-(2,4-difluoro-phenoxy)-3-(2-methoxy-phenyl)-1H-pyrazolo[4,3-c]pyridazine as a pale yellow solid. Mass Spec. M+H=355.

Similarly prepared, but replacing 2,4-difluorophenol in step 3 with 2,4-difluoroaniline, omitting the sodium hydride and adding conc. HCl instead, was (2,4-Difluoro-phenyl)-[3-(2-methoxy-phenyl)-1H-pyrazolo[4,3-c]pyridazin-6-yl]-amine.

Example 10

This example illustrates a synthesis of 6-(2,4-Difluoro-phenoxy)-3-isobutyl-1H-pyrazolo[3,4-d]pyrimidine following the procedure of Scheme V.

Step 1. Preparation of 5-Bromo-2,4-bis-(2,4-difluoro-phenoxy)-pyrimidine

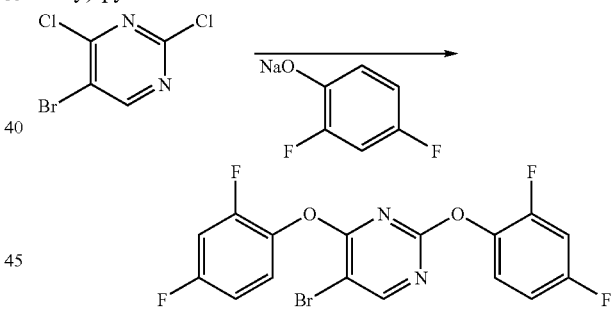

2,4-Difluorophenol (22 mL, 241.34 mmol) was dissolved in 140 mL of dry THF and cooled to 0° C. Sodium hydride (9.43 g, 235.85 mmol, 60% suspension in oil) was added in portions, and the reaction mixture was stirred for 30 minutes at 0° C. 5-Bromo-2,4-dichloro-pyrimidine (25.0 g, 109.7 mmol) was added in portions over 10 minutes, and the reaction mixture was allowed to warm to room temperature and was stirred overnight at room temperature. The reaction was quenched by addition of 30 mL saturated aqueous ammonium chloride and 100 mL of water. The aqueous mixture was extracted three times with 100 mL EtOAc, and the combined organic layers were dried (MgSO$_4$), filtered, and the filtrate was evaporated under reduced pressure. The residue was purified by FLASH chromatography (2% to 6% EtOAc/Hexanes. The resulting solid was recrystallized from diethyl ether/hexanes to afford 12.6 g of 5-bromo-2,4-bis-(2,4-difluoro-phenoxy)-pyrimidine as a white solid. Mass Spec. M+H=416.

Step 2. Preparation of 1-[2,4-Bis-(2,4-difluoro-phenoxy)-pyrimidin-5-yl]-3-methyl-butan-1-one

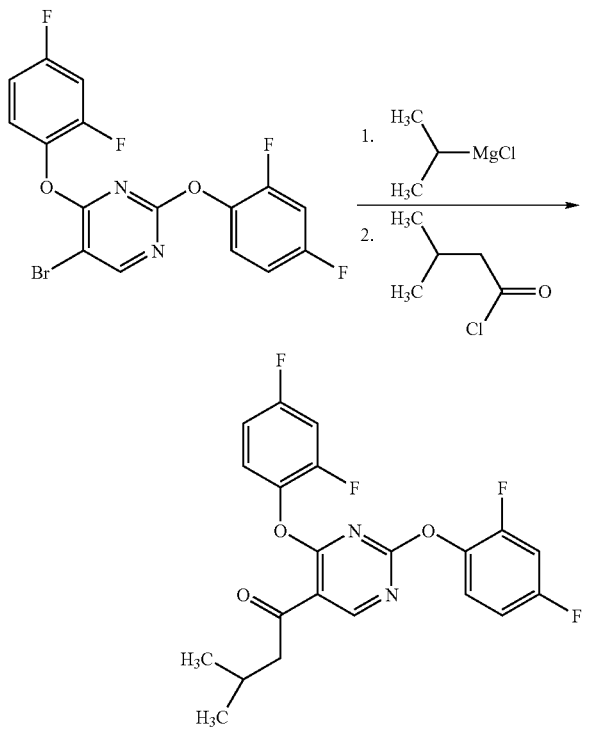

5-Bromo-2,4-bis-(2,4-difluoro-phenoxy)-pyrimidine (0.5 g, 1.2 mmol) was dissolved in 25 mL THF and cooled to 0° C. Isopropyl magnesium chloride (0.8 mL, 1.44 mmol) was added, and the reaction mixture was stirred for an hour at 0° C. Isovaleryl chloride (1.47 mL, 12.0 mmol) was then added, and the reaction mixture was stirred for another hour at 0° C. The reaction was quenched with 35 mL of saturated aqueous sodium bicarbonate and 25 mL water. The aqueous mixture was extracted three times with 25 mL EtOAc, and the combined organic layers were washed with saturated aqueous brine, dried ($Na_2SO_4$), filtered, and evaporated under reduced pressure. The residue was eluted through silica gel using 20% EtOAc in hexanes to yield 0.429 g (85%) of 1-[2,4-bis-(2,4-difluoro-phenoxy)-pyrimidin-5-yl]-3-methyl-butan-1-one. Mass Spec. M+H=421.

Step 3. Preparation of 6-(2,4-Difluoro-phenoxy)-3-isobutyl-1H-pyrazolo[3,4-d]pyrimidine.

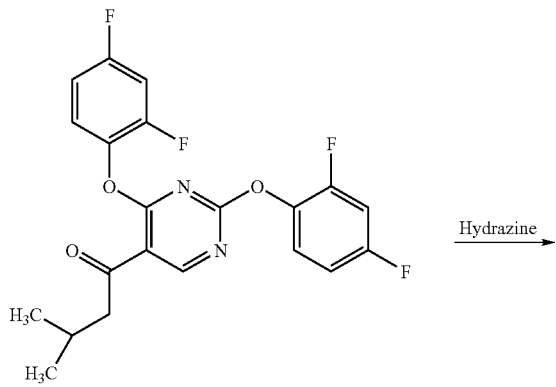

-continued

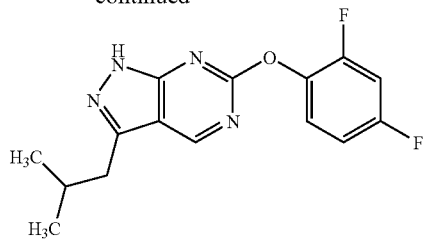

1-[2,4-Bis-(2,4-difluoro-phenoxy)-pyrimidin-5-yl]-3-methyl-butan-1-one (0.427 g, 1.0 mmol) was dilloved in 10 mL of 10:1 dioxane:EtOH, and hydrazine (0.032 mL) was added. The reaction mixture was heated to 90° C. for four hours, then cooled and quenched by addition of 25 mL saturated aqueous ammonium chloride and 25 mL water. The aqueous mixture was extracted three times with 25 mL EtOAc, and the combined organic layers were washed with saturated aqueous brine, dried ($Na_2SO_4$), filtered, and evaporated under reduced pressure. The residue was eluted through silica gel using 20% EtOAc in hexanes to yield 65 mg of 6-(2,4-difluoro-phenoxy)-3-isobutyl-1H-pyrazolo[3,4-d]pyrimidine as an oil. Mass Spec. M+H=305.

Example 11

This example illustrates a synthesis of 6-(2,4-Difluoro-phenoxy)-3-iodo-1H-pyrazolo[3,4-d]pyrimidine Step 1. Preparation of 4,6-Dichloro-2-methylsulfanyl-pyrimidine-5-carbaldehyde

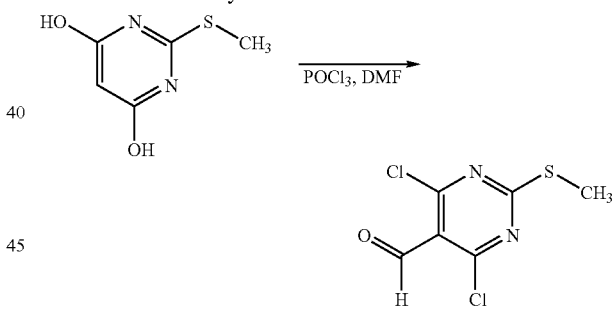

Phosphorous oxychloride (213 mL, 2.3 mol) was cooled in a sodium chloride-water ice bath to 1.8° C. under nitrogen. Dimethyl formamide (71.4 mL, 0.92 mol) was added dropwise over 45 minutes with stirring. The reaction mixture was allowed to warm up to room temperature and was stirred at room temperature for 30 minutes, and followed by stirring at 40° C. for 20 minutes. The reaction mixture was then heated to 57° C., and 2-Methylsulfanyl-pyrimidine-4,6-diol (50.0 g, 0.307 mol) was added in 5.0 g portions over 90 minutes. The reaction mixture was stirred for one hour at 55° C., and then heated to 110° C. with stirring for 17.5 hours. The reaction mixture was cooled and volatiles were removed under reduced pressure. The residue was poured into one litre of ice water. The resulting precipitate was isolated by filtration, washed with water, then with heptanes, and was dried to provide 25.2 g of crude 4,6-Dichloro-2-methylsulfanyl-pyrimidine-5-carbaldehyde. Mass Spec. M+H=224.

Step 2. Preparation of 4-Chloro-6-methylsulfanyl-1H-pyrazolo[3,4-d]pyrimidine

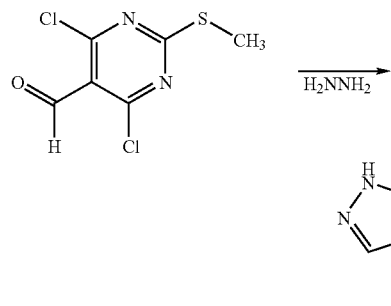

4,6-Dichloro-2-methylsulfanyl-pyrimidine-5-carbaldehyde (7.54 g, 0.0338 mol) was added to 80 mL of dioxane and stirred for 10 minutes at room temperature. Diisopropyl ethylamine (6.03 mL, 0.0340 mol) was added and the mixture was cooled in an ice bath with stirring for 10 minutes. Anhydrous hydrazine (1.08 mL, 0.0338 mmol) was added dropwise over three minutes, and stirring was continued for an additional five minutes. The ice bath was removed, and the reaction ixture was heated to reflux with stirring for two hours. The reaction mixture was then stirred at room temperature for 16 hours. The reaction mixture was concentrated under reduced pressure, and the residue was added to 20 mL of 2 N HCl and 100 mL EtOAc. The resulting suspension was stirred and filtered, ad the solid was washed with water followed by EtOAc. The organic phase of the filtrate was collected, and the aqueous phase was extracted three times with 150 mL EtOAc. The combined organic phases were dried (MgSO$_4$), filtered, and the filtrate was evaporated under reduced pressure. The resulting solid was washed with diethyl ether/hexanes (1:1) and the solid was dried to provide 3.13 g of crude 4-Chloro-6-methylsulfanyl-1H-pyrazolo[3,4-d]pyrimidine. Mass Spec. M+H=201.

Step 3. Preparation of 6-Methylsulfanyl-1H-pyrazolo[3,4-d]pyrimidine

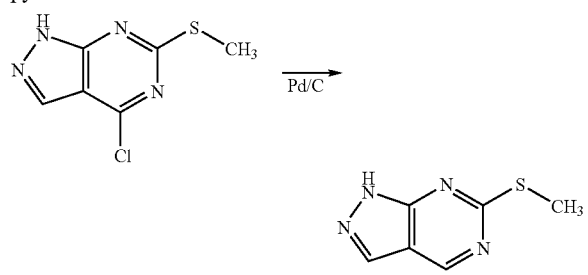

4-Chloro-6-methylsulfanyl-1H-indazole (11.02 g, 0.0549 mol) was disolved in a mixture of 160 mL THF and 350 mL MeOH, and triethylamine (7.66 mL, 0.055 mol) was added. While the reaction mixture was stirred at room temperature under argon, palladium on activated carbon (2.0 g of 10% Pd, 0.001 mol) was added. The reaction mixture was stirred under H$_2$ atmosphere for two hours, after which the reaction flask was flushed with argon, and another 2.0 g of palladium on activated carbon was added to the reaction mixture. The reaction mixture was again stirred for two hours under H$_2$, after which the flask was purged with argon, another 2.0 g of palladium on activated carbon was added, and the reaction mixture was stirred for 64 hours under hydrogen. The reaction mixture was filtered through Celite, and the Celite pad was washed twice with 200 mL of warm MeOH and twice with 200 mL of warm methylene chloride. The combined organic phases were evaporated under reduced pressure. The residue was suspended in water, filtered, and the filter cake was suspended in heptane, filtered, and dried to yield 5.36 g of 6-Methylsulfanyl-1H-pyrazolo[3,4-d]pyrimidine. Mass Spec. M+H=167.

Step 4. Preparation of 3-Iodo-6-methylsulfanyl-1H-pyrazolo[3,4-d]pyrimidine

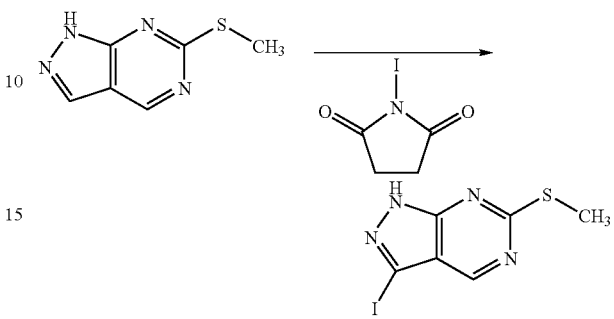

6-Methylsulfanyl-1H-indazole (5.36 g, 0.0322 mol) was dissolved in 210 mL of dry DMF, and the resulting reaction mixture was placed under nitrogen with stirring. Ni-iodosuccinimide (9.16 g, 0.0387 mol) was added, and the reaction mixture was heated to 80° C. with stirring for 16 hours under nitrogen. The reaction was quenched by addition of 100 mL of 10% aqueous NaHCO$_3$, 350 mL EtOAc and 150 mL water. The organic phase was removed and the remaining aqueous phase was extracted three times with 250 mL EtOAc. The combined organic phases were washed with saturated aqueous brine, dried over MgSO$_4$, filtered, and evaporated under reduced pressure. The resulting solid was stirred in 20 mL of heptanes, filtered, washed with heptanes, and dried to yield 6.66 g of 3-Iodo-6-methylsulfanyl-1H-pyrazolo[3,4-d]pyrimidine. Mass Spec. M+H=293.

Step 5. Preparation of 3-Iodo-6-methylsulfanyl-1-(2-trimethylsilanyl-ethoxymethyl)-1H-pyrazolo[3,4-d]pyrimidine

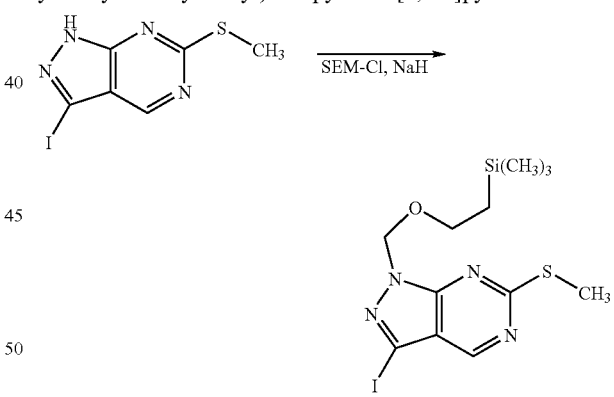

Sodium hydride (1.364 g of 60% dispersion in mineral oil, 0.0341 mol) was added to 50 mL dry DMF under nitrogen, and the reaction mixture was cooled to 5° C. A solution of 3-iodo-6-methylsulfanyl-1H-indazole (6.64 g, 0.0227 mol) in 100 mL of dry DMF was added, the ice cooling bath was removed, and the reaction mixture was stirred for 15 minutes under nitrogen. (2-Chloromethoxy-ethyl)-trimethyl-silane (4.21 mL, 0.024 mol) was added, and the reaction mixture was stirred for 16 hours under nitrogen at room temperature. Volatiles were removed from the reaction mixture under reduced pressure, and the resulting residue was added to 70 mL aqueous saturated ammonium chloride, 50 mL water, and 250 mL EtOAc. The oganic phase was removed and the aqueous phase was washed once with 250 mL of EtOAc. The combined organic phases were washed with saturated aqueous brine, dried over MgSO$_4$, filtered, and evaporated under reduced pressure. The resulting residue was purified by elution through a silica gel column with heptanes/EtOAc (4:1) to yield 6.43 g of 3-Iodo-6-methylsulfanyl-1-(2-trimethylsilanyl-ethoxymethyl)-1H-pyrazolo[3,4-d]pyrimidine.

Step 6 Preparation of 3-Iodo-6-methanesulfonyl-1-(2-trimethylsilanyl-ethoxymethyl)-1H-pyrazolo[3,4-d]pyrimidine

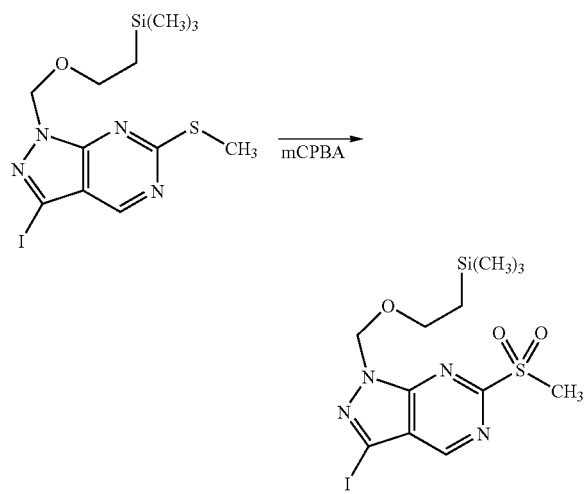

3-Iodo-6-methylsulfanyl-1-(2-trimethylsilanyl-ethoxymethyl)-1H-pyrazolo[3,4-d]pyrimidine (11.63 g, 0.0275 mol) was dissolved in 250 dry THF and stirred. 3-Chloroperbenzoic acid (12.96 g of 77% MCPBA, 0.578 mol) was added, and the reaction mixture was stirred overnight at room temperature. The reaction mixture was concentrated under reduced pressure and the residue was added to 85 mL of 10% aqueous NaHCO$_3$, 100 mL water, and 220 mL EtOAc. The aqueous phase was partitioned off and extracted once with 220 mL EtOAc. The combined organic phases were washed with saturated aqueous brine, dried over MgSO$_4$, filtered, and evaporated under reduced pressure to yield 15.0 g of 3-Iodo-6-methanesulfonyl-1-(2-trimethylsilanyl-ethoxymethyl)-1H-pyrazolo[3,4-d]pyrimidine.

Step 7. Preparation of 6-(2,4-Difluoro-phenoxy)-3-iodo-1-(2-trimethylsilanyl-ethoxymethyl)-1H-pyrazolo[3,4-d]pyrimidine

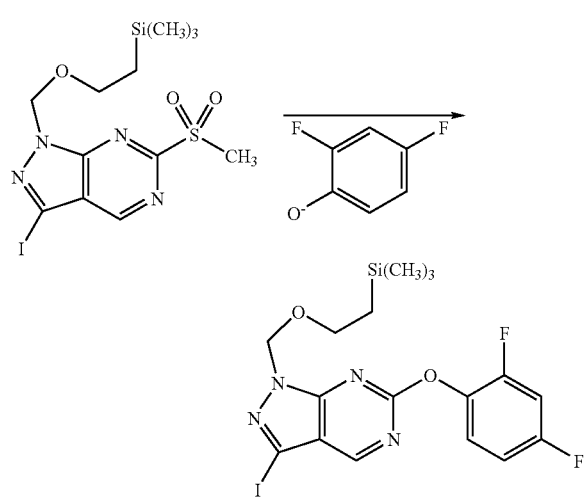

Sodium hydride (3.88 g of 60% dispersion in mineral oil, 0.097 mol) was added to 150 mL of dry DMF under nitrogen, and the reaction mixture was cooled in an ice bath. 2,4-Difluorophenol (8.85 mL, 0.092 mol) was added dropwise over 10 minutes (maintaining temperature between 5 and 10° C.), after which the reaction mixture was stirred for 15 minutes at 0° C., followed by 15 minutes of stirring at room temperature. A solution of 3-Iodo-6-methanesulfonyl-1-(2-trimethylsilanyl-ethoxymethyl)-1H-pyrazolo[3,4-d]pyrimidine (11.91 g, 0.026 mol) in 100 mL dry DMF was added, and the reaction mixture was heated to 140° C. for four hours while stirring under nitrogen. The reaction mixture was cooled to room temperature, and volatiles were removed under reduced pressure. The was added to 200 mL of 10% aqueous ammonium chloride, 50 mL water, and 250 mL EtOAc. The aqueous phase was partitioned off and extracted once with 250 mL EtOAc. The combined organic phases were washed with saturated aqueous brine, dried over MgSO$_4$, filtered, and evaporated under reduced pressure to yield an oil. The oil was eluted through silica gel with hexanes EtOAc (20:1 to 10:1) to afford 6.23 g of 6-(2,4-Difluoro-phenoxy)-3-iodo-1-(2-trimethylsilanyl-ethoxymethyl)-1H-pyrazolo[3,4-d]pyrimidine.

Step 8. Preparation of 6-(2,4-Difluoro-phenoxy)-3-iodo-1H-pyrazolo[3,4-d]pyrimidine

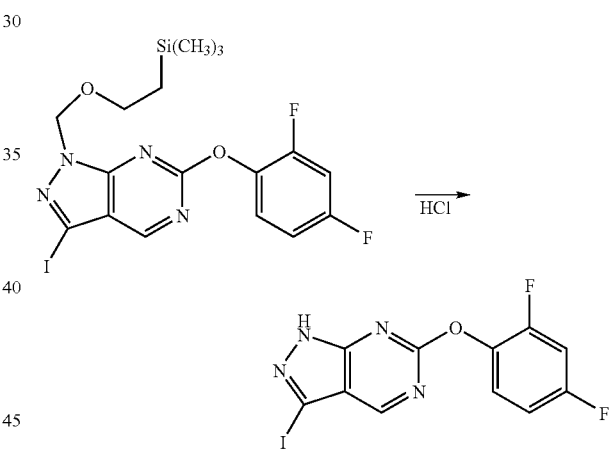

6-(2,4-Difluoro-phenoxy)-3-iodo-1-(2-trimethylsilanyl-ethoxymethyl)-1H-pyrazolo[3,4-d]pyrimidine (89 mg) was dissolved in 3 mL of MeOH. Aqueous HCl (2 mL, 18.5%) was added, and the mixture was heated to reflux for four hours. The reaction mixture was cooled to room temperature, transferred to a stoppered flask, and heated to 90° C. for w hours. The reaction mixture was evaporated under reduced pressure and the residue was taken up in 12 mL of EtOAc, made basic with 25 mL of 5 N NaOH, wahsed with water, saturated brine, dried over MgSO$_4$, filtered, and evaporated under reduced pressure to yield 26 mg of 6-(2,4-Difluoro-phenoxy)-3-iodo-1H-pyrazolo[3,4-d]pyrimidine. Mass Spec. M+H=373.

Example 12

This example illustrates a synthesis of 4-[6-(2,4-Difluoro-phenoxy)-1H-pyrazolo[3,4-d]pyrimidin-3-yl]-3-methyl-phenol.-

Step 1. Preparation of 4-[6-(2,4-Difluoro-phenoxy)-1-(2-trimethylsilanyl-ethoxymethyl)-1H-pyrazolo[3,4-d]pyrimidin-3-yl]-3-methyl-phenol

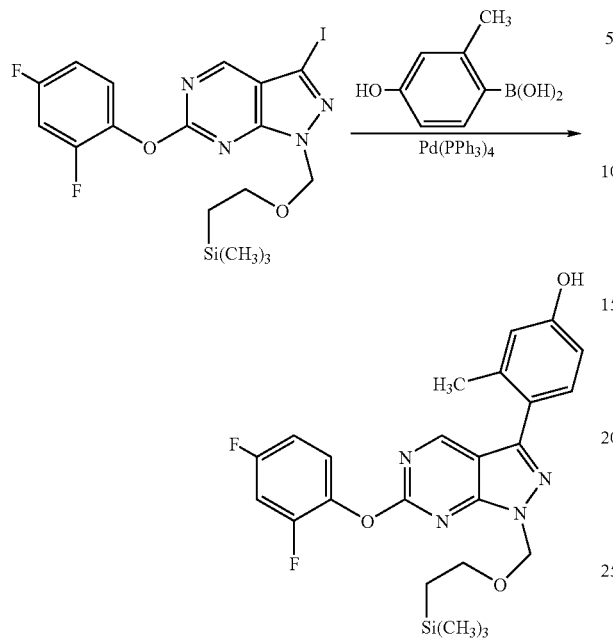

6-(2,4-Difluoro-phenoxy)-3-iodo-1-(2-trimethylsilanyl-ethoxymethyl)-1H-pyrazolo[3,4-d]pyrimidine from Example 11 (0.5 g, 0.99 mmol) was dissolved in 10 mL of dry dioxane, and the reaction mixture was degassed by treatment with vacuum and flushed with argon. Tetrakis(triphenylphosphine)palladium(0) (0.115 g, 0.1 mmol) was added, and the reaction mixture was stirred for 10 minutes. A solution of 4-hydroxy-2-methylphenyl boronic acid (0.311 g, 2.0 mmol) in 3 mL EtOH was added, and the reaction mixture was degassed, purged with argon, and stirred for 10 minutes. A A solution of potassium carbonate (0.411 g, 3.0 mmol) in 1 mL water was then added, and the reaction mixture was again degassed and flushed with argon. The reaction mixture was heated to 90° C. with stirring for 16 hours under argon. The reaction mixture was cooled, filtered, and the filtrate was partitioned between water and ethyl acetate. The organic phase was separated, and the aqueous phase was extracted three times with EtOAc. The combined organic layers were dried over MgSO₄, filtered, and evaporated under reduced pressure. The resulting residue was subject to flash chromatography (hexanes/EtOAc 1:0 to 2:1) to yield 0.308 g (0.64 mmol, 64%) of 4-[6-(2,4-difluoro-phenoxy)-1-(2-trimethylsilanyl-ethoxymethyl)-1H-pyrazolo[3,4-d]pyrimidin-3-yl]-3-methyl-phenol.

Step 2. Preparation of 4-[6-(2,4-Difluoro-phenoxy)-1H-pyrazolo[3,4-d]pyrimidin-3-yl]-3-methyl-phenol.

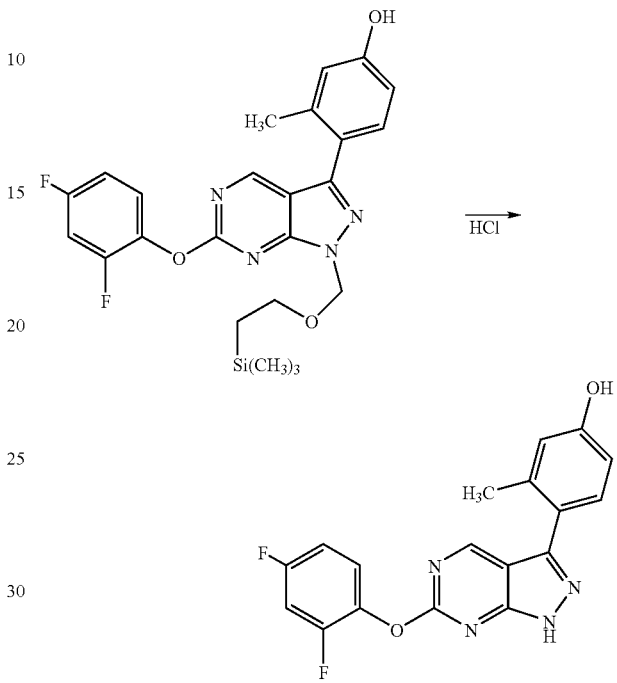

4-[6-(2,4-Difluoro-phenoxy)-1-(2-trimethylsilanyl-ethoxymethyl)-1H-pyrazolo[3,4-d]pyrimidin-3-yl]-3-methyl-phenol was treated with HCl using the procedure described in step 8 of Example 11 to afford 0.20 g of 4-[6-(2,4-difluoro-phenoxy)-1H-pyrazolo[3,4-d]pyrimidin-3-yl]-3-methyl-phenol. Mass Spec. M+H=355.

Additional compounds prepared by the above example are shown in Table 1.

Example 13

This example illustrates a synthesis of 3-{4-[6-(2,4-Difluoro-phenoxy)-1H-pyrazolo[3,4-d]pyrimidin-3-yl]-3-methyl-phenoxy}-propane-1,2-diol.

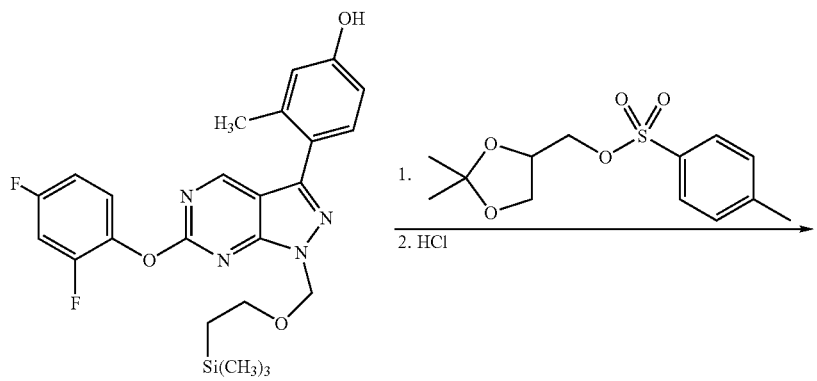

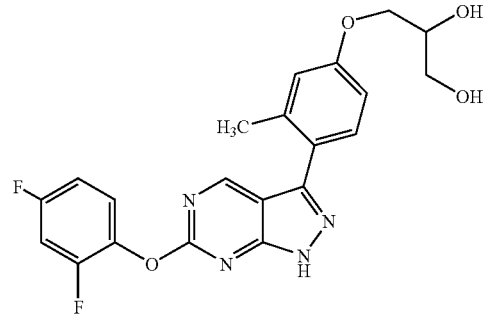

4-[6-(2,4-Difluoro-phenoxy)-1-(2-trimethylsilanyl-ethoxymethyl)-1H-pyrazolo[3,4-d]pyrimidin-3-yl]-3-methyl-phenol (0.125 g, 0.26 mmol) from Example 12 was placed in a microwave tube together with dry DMF (3.0 mL) and sodium hydride (0.021 g of 60% suspension in mineral oil, 0.31 mmol). 2,2-Dimethyl-1,3-dioxolan-4-ylmethyl p-toluene sulfonate (0.91 g, 0.31 mmol) was added, and the tube was sealed and heated to 85° C. for five minutes via microwave. The reaction mixture was cooled and partitioned between water and ethyl acetate. The organic phase was separated, and the aqueous phase was washed twice with ethyl acetate. The combined organic layers were dried over MgSO₄, filtered, and evaporated under reduced pressure. The resulting residue was dissloved in 3 mL of 4 N HCl in dioxane, transferred to a sealed tube, and heated to 90° C. for 90 minutes. The reaction mixture was cooled, partitioned between water and ethyl acetate, and made basic by addition of aqueous sodium bicarbonate (to pH 9). The organic phase was separated, and the aqueous phase was extracted three times with ethyl acetate. The combined organic layers were washed with saturated brine, dried over MgSO₄, filtered, and evaporated under reduced pressure. The residue was purified by preparative TLC plate using methylene chloride/MeOH 93:7 to yield 0.016 g (0.04 mmol, 14.5%) of 3-{4-[6-(2,4-difluorophenoxy)-1H-pyrazolo[3,4-d]pyrimidin-3-yl]-3-methyl-phenoxy}-propane-1,2-diol. Mass Spec. M+H=429.

Example 14

This example illustrates a synthesis of 6-(2,4-Difluoro-phenoxy)-3-styryl-1H-pyrazolo[3,4-d]pyrimidine.

Step 1. Preparation of 6-(2,4-Difluoro-phenoxy)-3-styryl-1-(2-trimethylsilanyl-ethoxymethyl)-1H-pyrazolo[3,4-d]pyrimidine

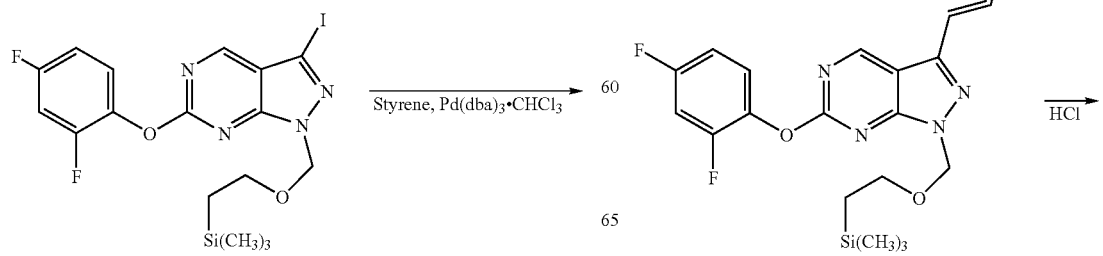

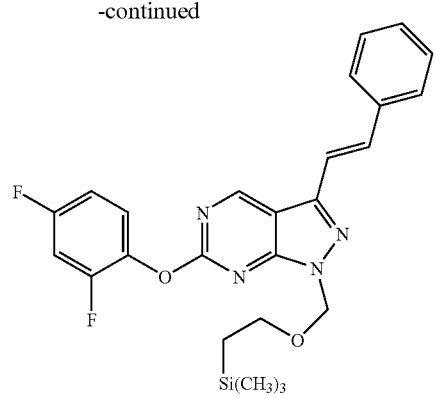

Tris(dibenzylidine acetone)dipalladium CHCl₃ (5.0 mg, 0.004 mmol), and potassium carbonate (26 mg, 0.19 mmol) were suspended in 1 mL of toluene under argon. A solution of 6-(2,4-Difluoro-phenoxy)-3-iodo-1-(2-trimethylsilanyl-ethoxymethyl)-1H-pyrazolo[3,4-d]pyrimidine (48 mg, 0.09 mmol) in 2 mL toluene was added, and the reaction mixture was stirred at 65° C. for 16 hours, then stirred at 110° C. for four hours. The reaction mixture was cooled, filtered through Celite, and the filtrate was concentrated under reduced pressure. The residue was purified by flash chromatography (23 mm×14 cm silica with hexanes/EtOAc 20:1 to 4:1) to yield 42 mg of 6-(2,4-Difluoro-phenoxy)-3-styryl-1-(2-trimethylsilanyl-ethoxymethyl)-1H-pyrazolo[3,4-d]pyrimidine.

Step 2. Preparation of 6-(2,4-Difluoro-phenoxy)-3-styryl-1H-pyrazolo[3,4-d]pyrimidine

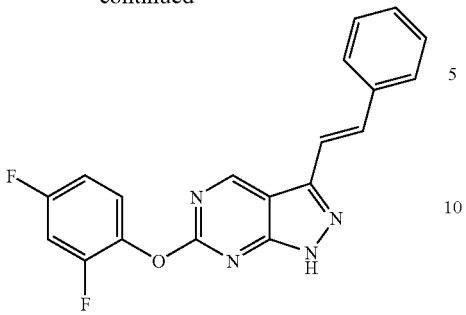

6-(2,4-Difluoro-phenoxy)-3-styryl-1-(2-trimethylsilanyl-ethoxymethyl)-1H-pyrazolo[3,4-d]pyrimidine (42 mg, 0.08 mmol) was dissolved in 1 mL MeOH and treated with 1.1 mL of 10% HCl in Et$_2$O. The reaction mixture was stirred overnight at room temperature, and then concentrated under reduced pressure. The residue was purified by preparative TLC (4:1 hexanes/EtOAc) to yield 0.037 g of 6-(2,4-difluoro-phenoxy)-3-styryl-1H-pyrazolo[3,4-d]pyrimidine. Mass Spec. M+H=351.

Example 15

This example illustrates a synthesis of 6-(2-Chloro-phenoxy)-3-thiophen-2-yl-1H-pyrazolo[3,4-d]pyrimidine.

Step 1. Preparation of 4-Chloro-2-methanesulfonyl-pyrimidine

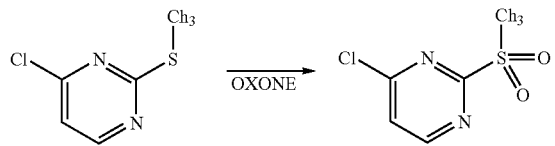

4-Chloro-2-methanesulfanyl-pyrimidine (15.0 g, 98.38 mmol) was dissolved in 220 mL MeOH and cooled to 0° C. OXONE (potassium peroxymonosulfate, 97 g) dissolved in 350 mL was added, and the reaction mixture was stirred at 0° C. for two hours. Approximately ⅔ of the volume of the reaction mixture was then removed under reduced pressure, and 10% aqueous sodium bicarbonate was carefully added. The mixture was partitioned with 300 mL EtOAc and the organic phase was separated. The aqueous phase was washed twice with 200 mL of EtOAc, and the combined organic layers were washed with brine, dried over MgSO$_4$, filtered, and evaporated under reduced pressure to yield 15.23 g of crude 4-chloro-2-methanesulfonyl-pyrimidine. Mass Spec. M+H=193.

Step 2. Preparation of 4-Chloro-2-(2-chloro-phenoxy)-pyrimidine

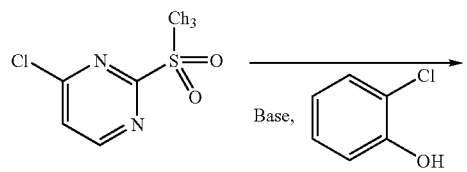

To a solution of 2-chlorophenol (10.5 g) in 150 mL dry THF) at 0° C. under argon was added 88 mL of a 1.0 M solution of potassium t-butoxide in THF. The reaction mixture was stirred for 15 minutes and then cooled to −78° C. A solution of 4-Chloro-2-methanesulfonyl-pyrimidine (14.2 g, 2.6 mmol) in 160 mL of dry THF was slowly added over 25 minutes. The reaction mixture was stirred for an additional 30 minutes at −78° C., and then quenched by addition of 60 mL saturated aqueous ammonium chloride, and evaporated under reduced pressure to remove THF. 200 mL water, and 200 mL EtOAc were added, the organic phase was collected, and the aqueous phase was washed twice with 150 mL EtOAc. The combined organic layers were washed with brine, dried over MgSO$_4$, filtered, and evaporated under reduced pressure. The residue was purified by flash chromatography (5% to 10% EtOAc/Hexanes) to 10.2 g of 4-Chloro-2-(2-chloro-phenoxy)-pyrimidine. Mass Spec. M+H=242.

Step 3. Preparation of [4-Chloro-2-(2-chloro-phenoxy)-pyrimidin-5-yl]-thiophen-2-yl-methanol

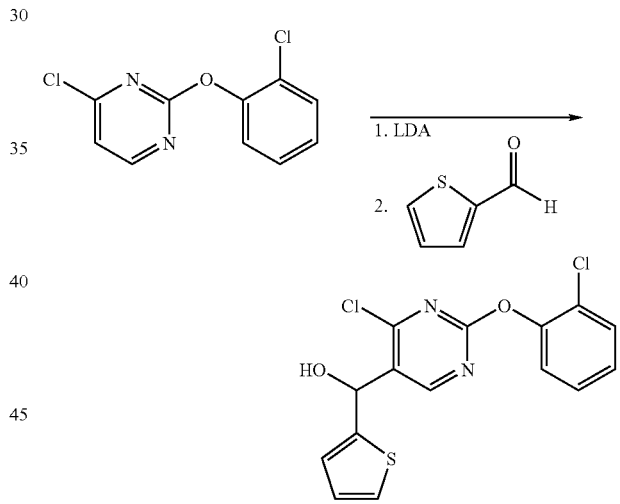

4-Chloro-2-(2-chloro-phenoxy)-pyrimidine (432 mg, 1.79 mmol) was dissolved in 10 mL of dry THF, and the reaction mixture was cooled to −78° C. under nitrogen. Lithium diisopropylamine (1.6 mL of 2M solution in THF) was added and the reaction mixture was stirred for eight minutes. Thiophene-2-carboxaldehyde (0.31 mL) was added, and the reaction mixture was stirred for 30 minutes at −78° C. The reaction was quenched by addition of 10 mL saturated aqueous ammonium chloride, and evaporated under reduced pressure to remove THF. Water (40 mL) and EtOAc (60 mL) were added, the organic phase was collected, and the aqueous phase was washed twice with 40 mL EtOAc. The combined organic layers were washed with brine, dried over MgSO$_4$, filtered, and evaporated under reduced pressure. The residue was purified by preparative TLC using 1.8% MeOH in methylene chloride to yield 98 mg of [4-Chloro-2-(2-chloro-phenoxy)-pyrimidin-5-yl]-thiophen-2-yl-methanol. Mass Spec. M+H=354.

Step 4. Preparation of [4-Chloro-2-(2-chloro-phenoxy)-pyrimidin-5-yl]-thiophen-2-yl-methanone

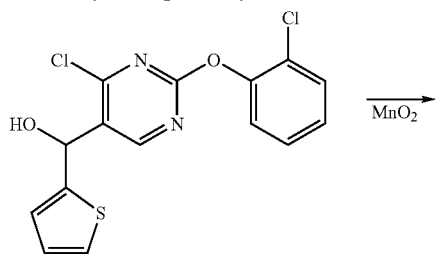

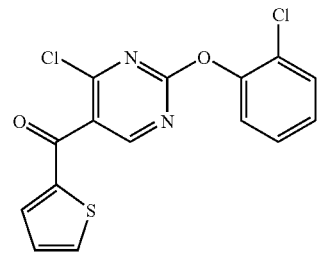

[4-Chloro-2-(2-chloro-phenoxy)-pyrimidin-5-yl]-thiophen-2-yl-methanol (98 mg, 0.28 mmol) was dissolved in 15 mL dry toluene, and 250 mg of MnO₂ was added. The reaction mixture was heated to reflux for 30 minutes, and water was removed using a Dean Stark apparatus. The hot reaction mixture was filtered through Celite, and the Celite was washed five times with 3.5 mL of hot EtOAc. The combined organics were evaporated under reduced pressure to yiled 82 mg of [4-Chloro-2-(2-chloro-phenoxy)-pyrimidin-5-yl]-thiophen-2-yl-methanone as an oil. Mass Spec. M+H=352.

Step 5. Preparation of 6-(2-Chloro-phenoxy)-3-thiophen-2-yl-1H-pyrazolo[3,4-d]pyrimidine.

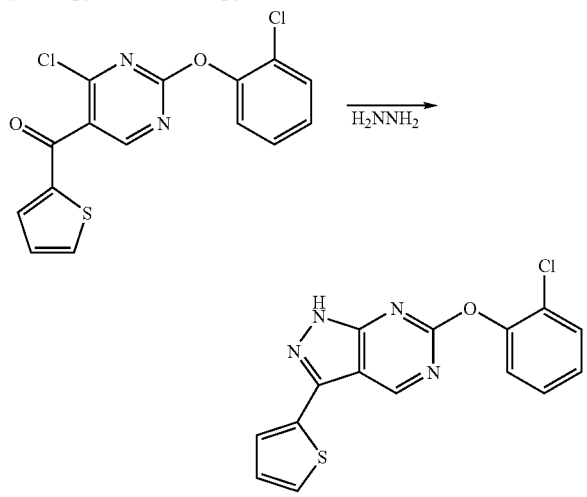

[4-Chloro-2-(2-chloro-phenoxy)-pyrimidin-5-yl]-thiophen-2-yl-methanone (82 mg, 0.23 mmol) was dissolved in a mixture of 10 mL ethanol and 0.5 mL THF, and 15 mg of anhydrous hydrazine was added. The reaction mixture was stirred at room temperature for 10 minutes and then was heated to 80° C. for 20 minutes. Solvent was removed under reduced pressure, and the residue was purified by preparative scale TLC using 1.8% MeOH in methylene chloride to yield 36 mg of 6-(2-Chloro-phenoxy)-3-thiophen-2-yl-1H-pyrazolo[3,4-d]pyrimidine. Mass Spec. M+H=329. Mp=221.3-223.1° C.

Additional compounds made by the above example, but replacing thiophene-2-carbaldehyde with the appropropriate benzaldehyde or pyridine carboxaldehyde, are shown in Table 1.

Example 16

This example illustrates a synthesis of 3-(2-Chloro-phenyl)-6-(2-fluoro-benzyl)-1H-pyrazolo[3,4-b]pyrazine.

Step 1. Preparation of [6-Chloro-5-(2-chloro-benzoyl)-pyrazin-2-yl]-(2-fluoro-phenyl)-acetic acid methyl ester

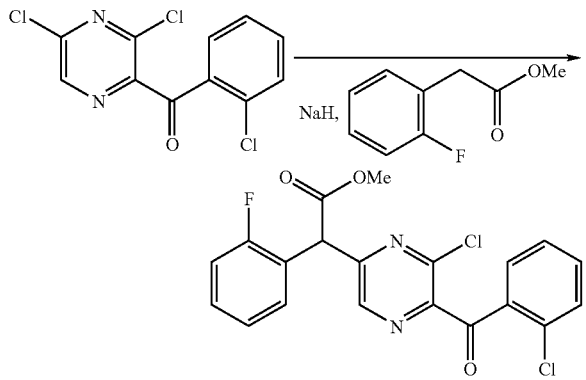

To a solution of sodium hydride (0.175 g, 7 mmol) and (2-Chloro-phenyl)-(3,5-dichloro-pyrazin-2-yl)-methanone (0.86 g, 2.99 mmol) in 5 mL DMF was added (2-Fluoro-phenyl)-acetic acid methyl ester (0.503 g, 2.99 mmol). The reaction mixture was stirred for one hour at room temperature, and then was quenched by addition of water and aqueous HCl. The aqueous mixture was extracted with methylene chloride, and the combined organic phases were dried over MgSO₄, filtered, and evaporated under reduced pressure to give 1.19 g of crude [6-Chloro-5-(2-chloro-benzoyl)-pyrazin-2-yl]-(2-fluoro-phenyl)-acetic acid methyl ester. Mass Spec. M+H=419.

Step 2. Preparation of 3-(2-Chloro-phenyl)-6-(2-fluoro-benzyl)-1H-pyrazolo[3,4-b]pyrazine

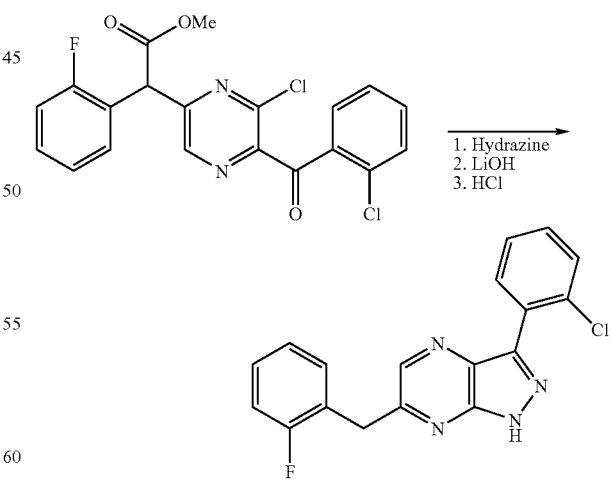

Hydrazine (54 mg, 1.7 mmol) was added to a solution of [6-Chloro-5-(2-chloro-benzoyl)-pyrazin-2-yl]-(2-fluoro-phenyl)-acetic acid methyl ester (0.59 g, 1.4 mmol) in 50 mL THF at 0° C., and the reaction mixture was stirred and allowed to warm to room temperature. Lithium hydroxide (27 mg, 5.0 mmol) was added, and the reaction mixture was stirred for 64 hours at room temperature. Concentrated aqueous HCl (1 ml) was then added, and the reaction mixture was stirred for one hour at room temperature. The reaction mixture was poured into water, extracted with diethyl ether, and the combined organic phases were dried over $MgSO_4$, filtered, and evaporated under reduced pressure. The residue was purified via chromatography using 5% ethyl acetate in hexanes as the eluent to afford 0.151 g of 3-(2-Chloro-phenyl)-6-(2-fluoro-benzyl)-1H-pyrazolo[3,4-b]pyrazine. Mass Spec. M+H=340.

Additional compounds prepared according to the above example are shown in Table 1.

Example 17

This example illustrates a p38 (MAP) kinase in vitro assay useful for evaluating the compounds of the invention.

The p38 MAP kinase inhibitory activity of compounds of this invention in vitro was determined by measuring the transfer of the γ-phosphate from γ-$^{33}$P-ATP by p-38 kinase to Myelin Basic Protein (MBP), using a minor modification of the method described in Ahn, et al., *J. Biol. Chem.* 266:4220-4227 (1991).

The phosphorylated form of the recombinant p38 MAP kinase was co-expressed with SEK-1 and MEKK in *E. Coli* (see, Khokhlatchev, et al., *J. Biol. Chem.* 272:11057-11062 (1997)) and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis (beta-aminoethyl ether)-N,N,N',N'-tetraacetic acid, 1 mM sodium ortho-vanadate, 1 mM dithiothreitol, 40 mM magnesium chloride). Test compound dissolved in DMSO or only DMSO (control) was added and the samples were incubated for 10 min at 30° C. The kinase reaction was initiated by the addition of a substrate cocktail containing MBP and γ-$^{33}$P-ATP. After incubating for an additional 20 min at 30° C., the reaction was terminated by adding 0.75% phosphoric acid. The phosphorylated MBP was then separated from the residual γ-$^{33}$P-ATP using a phosphocellulose membrane (Millipore, Bedfrod, Mass.) and quantitated using a scintillation counter (Packard, Meriden, Conn.).

Using the above procedure, the compounds of the invention were found to be inhibitors of p38 MAP kinase. For example, 3-(2-Chloro-phenyl)-6-(2,4-difluoro-phenoxy)-1H-pyrazolo[3,4-d]pyrimidine exhibits a p38 $IC_{50}$ (uM) of approximately 0.01.

Example 16

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
| --- | --- |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula I:

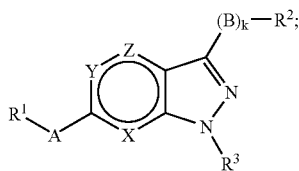

or a pharmaceutically acceptable salt thereof,
wherein:
R$^1$ is 2,4-difluorophenyl, 4-fluorophenyl, 3-fluorophenyl, 2-fluorophenyl, phenyl, 2-chlorophenyl, 3,4-difluorophenyl, 4-trifluoromethylphenyl, 3-trifluoromethylphenyl, 2-trifluoromethylphenyl, 4-methylphenyl, 4-methoxyphenyl, 3,4-dichlorophenyl, or 1,3-benzodioxol-5-yl;

R$^2$ is phenyl optionally substituted with halo, alkyl, amino, alkoxy, haloalkyl, hydroxy, hydroxyalkoxy, alkylsulfanyl, alkoxyamino, heteroaryl, heterocyclyl, heterocyclylalkyl, heterocyclyloxy, heterocyclylalkoxy, aminoalkoxy, hydroxyalkylamino, hydroxyalkylaminoalkyl, aralkyloxy, or pyridylalkyloxy;

R$^3$ is hydrogen or alkyl;
X and Y are N and Z is CR$^4$;
R$^4$ is hydrogen;
A is O;
k is 0 or 1;
B is O, NR$^8$, S(O)$_j$, CH(OR$^9$), CH=CH, or C(=O), wherein
j is 0, 1 or 2; and
R$^8$ is hydrogen, alkyl, —C(=O)—R$^{10}$, or —SO$_2$R$^5$, wherein
R$^{10}$ is alkyl, hydroxy, alkoxy, amino, heteroalkyl, aryl, aralkyl, heteroaryl or heterocyclyl; and
R$^5$ is alkyl; and
R$^9$ is hydrogen or alkyl.

2. The compound of claim 1, wherein k is 0.
3. The compound of claim 2, wherein R$^3$ is hydrogen.
4. The compound of claim 1, wherein said compound is of the formula III:

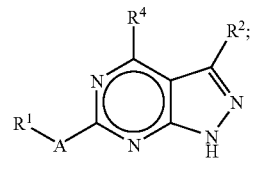

wherein A, R$^1$, R$^2$ and R$^4$ are as defined in claim 1.

5. The compound of claim 1, wherein said A compound is of the formula IX:

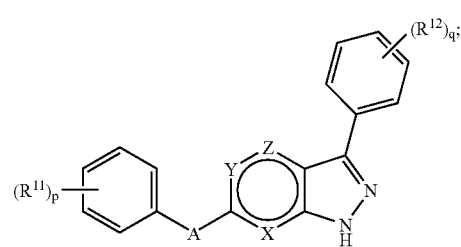

wherein:
each of p and q is independently from 0 to 4;
each R$^{11}$ is independently halo, alkyl, alkoxy, haloalkyl, or cyano;
each R$^{12}$ is independently halo, alkyl, amino, alkoxy, haloalkyl, hydroxy, hydroxyalkoxy, alkylsulfanyl, alkoxyamino, heteroaryl, heterocyclyl, heterocyclylalkyl, heterocyclyloxy, heterocyclylalkoxy, aminoalkoxy, hydroxyalkylamino, hydroxyalkylaminoalkyl, aralkyloxy, or pyridylalkyloxy; and
X and Y are N and Z is CR$^4$;
R$^4$ is hydrogen; and
A is O.

6. The compound of claim 5, wherein said compound is of the formula XI:

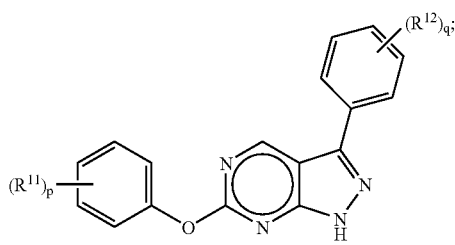

wherein:
p is 1 or 2;
$R^{11}$ is halo;
p is 1 or 2; and
$R^{12}$ is chloro,. fluoro, bromo, methyl, methoxy, trifluoromethyl, pyridyl, morpholino, benzyloxy, 4-methylpiperidinyl, 2-methoxyethyl-methylamino, isopropoxy, pyridin-2-ylethoxy, amino, methylsulfanyl, 2,3-dihydroxypropoxy, 2-hydroxyethoxy, 2-(morpholin-4-yl)-ethoxy, 2-dimethylamino)-ethoxy, 3,4-dihydroxybutyloxy, morpholin-4-ylmethyl, (2-hydroxypropyl)-aminomethyl, hydroxymethyl, ethoxy, piperidin-4-yloxy, or pyran-4-yloxy.

7. A composition comprising:
(a) a pharmaceutically acceptable excipient; and
(b) a compound of claim 1.

8. A method for treating rheumatoid arthritis or osteoarthritis, said method comprising administering to a patient a therapeutically effective amount of a compound of claim 1.

9. A compound is selected from the group consisting of:
6-(2-Chloro-phenoxy)-3-(2-chloro-phenyl)-1H-pyrazolo[3,4-d]pyrimidine;
3-(2-Chloro-phenyl)-6-phenoxy-1H-pyrazolo[3,4-d]pyrimidine;
3-(2-Chloro-phenyl)-6-(2,4-difluoro-phenoxy)-1H-pyrazolo[3,4-d]pyrimidine;
3-(2-Chloro-phenyl)-6-(2-fluoro-phenoxy)-1H-pyrazol[3,4-d]pyrimidine;
3-(2-Chloro-phenyl)-6-p-tolyloxy-1H-pyrazolo[3,4-d]pyrimidine;
3-(2-Chloro-phenyl)-6-(3,4-dichloro-phenoxy)-1H-pyrazolo[3,4-d]pyrimidine;
3-(2-Chloro-phenyl)-6-(3,4-dichloro-phenoxy)-1H-pyrazolo[3,4-d]pyrimidine;
6-(2-Fluoro-phenoxy)-3-(4-fluoro-phenyl)-1H-pyrazolo[3,4-d]pyrimidine;
3-(4-Fluoro-phenyl)-6-(4-methoxy-phenoxy)-1H-pyrazolo[3,4-d]pyrimidine;
3-(2-Chloro-phenyl)-6-(4-fluoro-phenoxy)-1H-pyrazolo[3,4-d]pyrimidine;
3-(2-Chloro-phenyl)-6-(4-methoxy-phenoxy)-1H-pyrazolo[3,4-d]pyrimidine;
3-(2-Chloro-phenyl)-6-(2-trifluoromethyl-phenoxy)-1H-pyrazolo[3,4-d]pyrimidine;
3-(2-Chloro-phenyl)-6-cyclohexyloxy-1H-pyrazolo[3,4-d]pyrimidine;
3-(2-Chloro-phenyl)-6-morpholin-4-yl-1H-pyrazolo[3,4-d]pyrimidine;
6-(2-Chloro-phenoxy)-3-(3-fluoro-phenyl)-1H-pyrazolo[3,4-d]pyrimidine;
6-(2-Chloro-phenoxy)-3-(4-methoxy-phenyl)-1H-pyrazolo[3,4-d]pyrimidine;
6-(2-Chloro-phenoxy)-3-(3-trifluoromethyl-phenyl)-1H-pyrazolo[3,4-d]pyrimidine;
6-(2-Chloro-phenoxy)-3-pyridin-3-yl-1H-pyrazolo[3,4-d]pyrimidine;
3-(2-Chloro-phenyl)-6-(4-trifluoromethyl-phenoxy)-1H-pyrazolo[3,4-d]pyrimidine;
6-(2-Chloro-phenoxy)-3-(4-pyridin-2-yl-phenyl)-1H-pyrazolo[3,4-d]pyrimidine;
6-(2-Chloro-phenoxy)-3-thiophen-2-yl-1H-pyrazolo[3,4-d]pyrimidine;
6-(Benzo[1,3]dioxol-5-yloxy)-3-(2-chloro-phenyl)-1H-pyrazolo[3,4-d]pyrimidine;
3-(2-Chloro-phenyl)-6-(2,4-difluoro-phenylsulfanyl)-1H-pyrazolo[3,4-d]pyrimidine;
3-(2-Chloro-phenyl)-6-(4-fluoro-phenylsulfanyl)-1H-pyrazolo[3,4-d]pyrimidine;
3-(2-Chloro-phenyl)-6-(2-fluoro-phenylsulfanyl)-1H-pyrazolo[3,4-d]pyrimidine;
3-(2-Chloro-phenyl)-6-phenylsulfanyl-1H-pyrazolo[3,4-d]pyrimidine;
6-(2,4-Difluoro-phenoxy)-3-(3-morpholin-4-yl-phenyl)-1H-pyrazolo[3,4-d]pyrimidine;
4-[6-(2,4-Difluoro-phenoxy)-1H-pyrazolo[3,4-d]pyrimidin-3-yl]-phenol;
3-(4-Benzyloxy-phenyl)-6-(2,4-difluoro-phenoxy)-1H-pyrazolo[3,4-d]pyrimidine;
6-(2,4-Difluoro-phenoxy)-3-[3-(4-methyl-piperazin-1-yl)-phenyl]-1H-pyrazolo[3,4-d]pyrimidine;
6-(2,4-Difluoro-phenoxy)-3-(4-morpholin-4-yl-phenyl)-1H-pyrazolo[3,4-d]pyrimidinc;
3-(2-Chloro-phenyl)-6-(2,4-difluoro-benzenesulfonyl)-1H-pyrazolo[3,4-d]pyrimidine;
3-(2-Chloro-phenyl)-6-(2,4-difluoro-benzenesulfinyl)-1H-pyrazolo[3,4-d]pyriniidine;
{3-[6-(2,4-Difluoro-phenoxy)-1H-pyrazolo[3,4-d]pyrimidin-3-yl]-phenyl}-(2-methoxy-ethyl)-methyl-amine;
6-(2,4-Difluoro-phenoxy)-3-(4-isopropoxy-phenyl)-1H-pyrazolo[3,4-d]pyrimidine;
6-(2,4-Difluoro-phenoxy)-3-[3-(2-pyridin-2-yl-ethoxy)-phenyl]-1H-pyrazolo[3,4-d]pyrimidine;
4-[6-(2,4-Difluoro-phenoxy)-1H-pyrazolo[3,4-d]pyrimidin-3-yl]-phenylamine;
6-(2,4-Difluoro-phenoxy)-3-[4-(4-methyl-piperazin-1-yl)-phenyl]-1H-pyrazolo[3,4-d]pyrimidine;
3-(4-Bromo-phenyl)-6-(2,4-difluoro-phenoxy)-1H-pyrazolo[3,4-d]pyrimidine;
6-(2-Chloro-phenoxy)-3-(2-fluoro-phenyl)-1H-pyrazolo[3,4-d]pyrimidine;
3-(2-Chloro-phenyl)-6-(2,4-difluoro-phenoxy)-1-methyl-1H-pyrazolo[3,4-d]pyrimidine;
3-(2-Chloro-phenyl)-6-(2,4-difluoro-benzyloxy)-1H-pyrazolo[3,4-d]pyrimidine;
3(2-Chloro-phenyl)-6-(3-fluoro-phenylsulfanyl)-1H-pyrazolo[3,4-d]pyrimidine;
3-(3-Benzyloxy-phenyl)-6-(2,4-difluoro-phenoxy)-1H-pyrazolo[3,4-d]pyrimidine;
6-(2,4-Difluoro-phenoxy)-3-(2-methylsulfanyl-phenyl)-1H-pyrazolo[3,4-d]pyrimidine;
6-(2,4-Difluoro-phenoxy)-3-o-tolyl-1H-pyrazolo[3,4-d]pyrimidine;
6-(2,4-Difluoro-phenoxy)-3-(4-methoxy-2-methyl-phenyl)-1H-pyrazolo[3,4-d]pyrimidine;
3-{4-[6-(2,4-Difluoro-phenoxy)-1H-pyrazolo[3,4-d]pyrimidin-3-yl]-3-methyl-phenoxy}-propane-1,2-diol;
3-(2-Chloro-4-methoxy-phenyl)-6-(2,4-difluoro-phenoxy)-1H-pyrazolo[3,4-d]pyrimidine;
6-(2,4-Difluoro-phenoxy)-3-(3-methyl-pyridin-2-yl)-1H-pyrazolo[3,4-d]pyrimidine;

6-(2,4-Difluoro-phenoxy)-3-(2-fluoro-phenyl)-1H-pyrazolo[3,4-d]pyrimidine;
6-(2,4-Difluoro-phenoxy)-3-(2-fluoro-5-methoxy-phenyl)-1H-pyrazolo[3,4-d]pyrimidine;
6-(2,4-Difluoro-phenoxy)-3-(4-fluoro-2-methyl-phenyl)-1H-pyrazolo[3,4-d]pyrimidine;
6-(2,4-Difluoro-phenoxy)-3-(2,4-dimethyl-phenyl)-1H-pyrazolo[3,4-d]pyrimidine;
6-(2,4-Difluoro-phenoxy)-3-(2-fluoro-4-morpholin4-phenyl)-1H -pyrazolo[3,4-d]pyrimidine;
3-(4-Bromo-2-fluoro-phenyl)-6-(2,4-difluoro-phenoxy)-1H-pyrazolo[3,4-d]pyrimidine;
3-(2-Chloro-4-methyl-phenyl)-6-(2,4-difluoro-phenoxy)-1H-pyrazolo[3,4-d]pyrimidine;
6-(2,4-Difluoro-phenoxy)-3-(2-methylsulfanyl-phenyl]1H-pyrazolo[3,4-d]pyrimidine;
6-(2,4-Difluoro-phenoxy)-3-(2-fluoro-6-methoxy-phenyl)-1H-pyrazolo[3,4-d]pyrimidine;
4-[6-(2,4-Difluoro-phenoxy)-1H-pyrazolo[3,4-d]pyrimidin-3-yl]3-methyl-phenol;
3-{4-[6-(2,4-Difluoro-phenoxy)-1H-pyrazolo[3,4-d]pyrimidin-3-yl]-3-methyl-phenoxy}-propane-1,2-diol;
2- {4-[6-(2,4-Difluoro-phenoxy)-1H-pyrazolo[3,4-d]pyrimidin-3-yl]-3-methyl-phenoxy}-ethanol;
3-{3-Chloro-4-[6-(2,4-difluoro-phenoxy)-1H-pyrazolo[3,4-d]pyrimidin-3-yl]-phenoxy}-propane-1,2-diol;
3-Chloro-4-(6-(2,4-difluoro-phenoxy)- 1H-pyrazolo[3,4-d]pyrimidin-3-yl]-phenol;
2-{3-Chloro-4-[6-(2,4-difluoro-phenoxy)-1H-pyrazolo[3,4-d]pyrimidin-3-yl]-phenoxy}-ethanol;
6-(2,4-Difluoro-phenoxy)-3-styryl]-1H-pyrazolo[3,4-d]pyrimidine;
3-[2-Chloro-4-(2-morpholin-4-yl-ethoxy)-phenyl]-6-(2,4-difluoro-phenoxy)-1H -pyrazolo[3,4-d]pyrimidine;
(2-{3-Chloro-4-[6-(2,4-difluoro-phenoxy)-1H-pyrazolo[3,4-d]pyrimidin-3-yl]-phenoxy}-ethyl)-dimethyl-armine;
4-{3-Chloro-4-[6-(2,4-difluoro-phenoxy)-1H-pyrazolo[3,4-d]pyrimidin-3-yl]-phenoxy)-butane-1,2-diol;
3-(2-Chloro-4-morpholin-4-ylmethyl-phenyl)-6-(2,4-difluoro-phenoxy)-1H -pyrazolo[3,4-d]pyrimidine;
2-{3-Chloro-4-[6-(2,4-difluoro-phenoxy)-1H-pyrazolo[3,4-d]pyrimidin-3-yl]-benzylamino}-propan-1-ol;
3-{4-Chloro-3-[6-(2,4-difluoro-phenoxy)-1H-pyrazolo[3,4-d]pyrimidin-3-yl]-phenoxy}-propane-1,2-diol;
4-Chloro-3-[6-(2,4-difluoro-phenoxy)-1H-pyrazolo[3,4-d]pyrimidin-3-yl]-phenol;
2-{4-Chloro-3-[6-(2,4-difluoro-phenoxy)-1H-pyrazolo[3,4-d]pyrimidin-3-yl]-phenoxy)-ethanol;
{3-Chloro-4-[6-(2,4-difluoro-phenoxy)-1H-pyrazolo[3,4-d]pyrimidin-3-yl]-phenyl)-methanol;
3-{4-Chloro-3-[6-(2,4-difluoro-phenoxy)-1H-pyrazolo[3,4-d]pyrimidin-3-yl]-phenoxy}-propane-1,2-diol;
3-{4-Chloro-3-[6-(2,4-difluoro-phenoxy)-1H-pyrazolo[3,4-d]pyrimidin-3-yl]-phenoxy)-propane-1,2-diol;
(2-{4-Chloro-3-[6-(2,4-difluoro-phenoxy)-1H-pyrazolo[3,4-d]pyrimidin-3-yl]-phenoxy}-ethyl)-dimethylamine;
6-(2,4-Difluoro-phenoxy)-3-(2-methoxy-pyridin-3-yl)-1H-pyrazolo[3,4-d]pyrimidine;
3-[2-Chloro-5-(piperidin-4-yloxy)-phenyl]-6-(2,4-difluoro-phenoxy)-1H -pyrazolo[3,4-d]pyrimidine;
3-[2-Chloro-5-(tetrahydro-pyran-4-yloxy)-phenyl]-6-(2,4-difluoro-phenoxy)-1H -pyrazolo[3,4-d]pyrimidine; and
6-(2,4-Difluoro-phenoxy)-3-(2-methyl-pyridin-3-yl)-1H-pyrazolo[3,4-d]pyrimidine.

10. The compound of claim 1, wherein $R^1$ is 2,4-difluorophenyl.

11. A compound of the formula II:

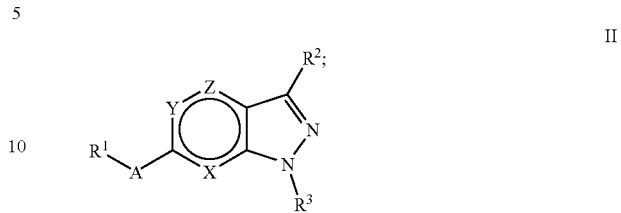

or a pharmaceutically acceptabic salt thereof,
wherein:
$R^1$ is 2,4-difluorophenyl, 4-fluorophenyl, 3-fluorophenyl, 2-fluorophenyl, phenyl, 2-chlorophenyl, 3,4-difluorophenyl, 4-trifluoromethylphenyl, 3-trifluoromethylphenyl, 2-triflurormethylphenyl, 4-methylphenyl, 4-methoxyphenyl, 3,4-dichlorophenyl, or 1,3-benzodioxol-5-yl;
$R^2$ is phenyl optionally substituted with chloro, fluoro, bromo, methyl, methoxy, trifluorormethyl, pyridyl, morpholino, benzyloxy, 4-methylpiperidinyl, 2-methoxyethyl -methylamino, isopropoxy, pyridin-2-ylethoxy, amino, methylsulfanyl, 2,3-dihydroxypropoxy, 2-hydroxyethoxy, 2-(morpholin-4-yl)-ethoxy, 2-(dimethylamino) -ethoxy, 3,4-dihydroxybutyloxy, morpholin-4-ylmethyl, (2-hydroxypropyl)-aminomethyl, hydroxymethyl, ethoxy, piperidin-4-yloxy, or pyran-4-yloxy;
$R^3$ is hydrogen or alkyl;
X and Y are N and Z is $CR^4$;
$R^4$ is hydrogen; and
A is O.

12. A compound of the formula II:

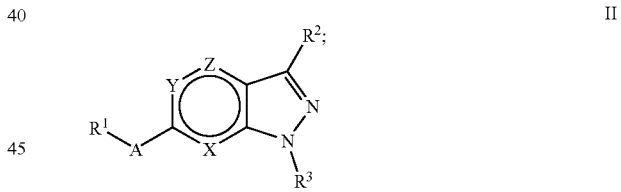

or a pharmaccutically acceptable salt thereof,
wherein:
$R^1$ is 2,4-difluorophenyl, 4-fluorophenyl, 3-fluorophenyl, 2-fluorophenyl, phenyl, 2-chlorophenyl, 3,4-difluorophenyl, 4-trifluoromethylphenyl, 3-trifluoromethylphenyl, 2-trifluoromethylphenyl, 4-methylphenyl, 4-methoxyphenyl, 3,4-dichlorophenyl, or 1,3-benzodioxol-5-yl;
$R^2$ is 2-chlorophenyl, 4-fluorophenyl, 4-methoxyphenyl, 3-trifluormethylphenyl, pyridin-2-yl, pyridin-3-yl, thien-2-yl, 3-(morpholin-4-yl)-phenyl, 4-hydroxyphenyl, 4-benzyloxyphenyl, 3-(4-methyl-piperazin-1-yl)-phenyl, 4-(morpholin-4-yl)-phenyl, 3-(2-methoxyethylmethylamino)-phenyl, 4-isopropoxyphenyl, 3-(2-pyridin-2-yl-ethoxy) -phenyl, 4-aminophenyl, 4-(4-methyl-piperazin-1-yl)-phenyl, 4-bromophenyl, 2-fluorophenyl, 3-benzyloxyphenyl, 2-methylsulfanyl, 4-methoxy-2-methylphenyl, 4(2,3-dihydroxypropoxy)-2-methyl-phenyl, 2-chloro-4-methoxyphenyl, 3-methylpyridin-2-yl, 2-fluoro-5-methoxyphenyl, 4-fluoro-2-methylphenyl, 2,4-dimethylphenyl, 2-fluoro-4-(morpholin-4-yl)-phenyl, 4-bromo-2-fluorophenyl, 2-chloro-4-methylphenyl, 2-fluoro-6-methoxyphenyl, 4-hydroxy-2-methylphenyl, 4-(2-hydroxyethoxy)-2-methylphenyl, 2-chloro-4-(2,3-dihydroxypropoxy)-phenyl, 2-chloro-4-hydroxyphenyl, 2-chloro-4-(2-hydroxyethoxy)-phenyl, 2-chloro-4-(2-[morpholin-4-yl]-ethoxy)-phenyl, 2-chloro-4-(2-dimcehylamino)-ethoxy-phenyl, 2-chloro-4-2,3-dihydroxypropoxyphenyl, 2-chloro-4-(morpholin-4-ylmethyl)-phenyl, 2-chloro-4-(2-hydroxypropyl) aminomethyl-phenyl, 2-chloro-5-2,3-dihydroxypropoxyphenyl, 2-chloro-5-hydroxyphenyl, 2-chloro-5-(2-hydroxyethyoxy)-phenyl, 2-chloro-4-hydroxymethylphenyl, 2-ethoxyphenyl, 2ethoxypyridin-3-yl-phenyl, 2-chloro-5-(2-dimethylaminoethoxy)-phenyl, 2-chloro-5-piperidin-4-yloxy-phenyl, 2-chloro-5-pyran-4-yloxy-phenyl, or 2-methylpyridin-3-yl -phenyl;

$R^3$ is hydrogen or alkyl;

X and Y are N and Z is $CR^4$;

$R^4$ is hydrogen; and

A is O.

* * * * *